United States Patent
Yee et al.

(10) Patent No.: US 9,314,516 B2
(45) Date of Patent: Apr. 19, 2016

(54) CONDITIONAL SUPERAGONIST CTL LIGANDS FOR THE PROMOTION OF TUMOR-SPECIFIC CTL RESPONSES

(75) Inventors: Cassian Yee, Seattle, WA (US); Yongqing Li, Shoreline, WA (US); C. Siddiq Abdul-Alim, Kent, WA (US)

(73) Assignees: Cassian Yee, Seattle, WA (US); Yongqing Li, Shoreline, WA (US); C. Siddiq Abdul-Alim, Kent, WA (US)

( * ) Notice: Subject to any disclaimer, the term of this patent is extended or adjusted under 35 U.S.C. 154(b) by 0 days.

(21) Appl. No.: 13/696,303

(22) PCT Filed: May 4, 2011

(86) PCT No.: PCT/US2011/035272
§ 371 (c)(1),
(2), (4) Date: Jan. 8, 2013

(87) PCT Pub. No.: WO2011/140284
PCT Pub. Date: Nov. 10, 2011

(65) Prior Publication Data
US 2013/0108657 A1    May 2, 2013

Related U.S. Application Data

(60) Provisional application No. 61/331,260, filed on May 4, 2010.

(51) Int. Cl.
*A61K 39/00* (2006.01)
*C07K 7/00* (2006.01)
*C07K 14/47* (2006.01)

(52) U.S. Cl.
CPC ......... *A61K 39/0011* (2013.01); *C07K 14/4748* (2013.01); *A61K 2039/57* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,844,075 A | * | 12/1998 | Kawakami et al. | 530/326 |
| 6,251,603 B1 | * | 6/2001 | Jager et al. | 435/6.11 |
| 7,619,057 B2 | * | 11/2009 | Wang et al. | 530/300 |

FOREIGN PATENT DOCUMENTS

| | | | | |
|---|---|---|---|---|
| WO | WO02/092120 | * | 11/2002 | A61K 38/04 |
| WO | WO 2008/124483 | | 10/2008 | |
| WO | WO 2009/051555 | | 4/2009 | |

OTHER PUBLICATIONS

Fomsgaard et al., "Induction of cytotoxic T-cell responses by gene gun DNA vaccination with minigenes encoding influenza A virus HA and NP CTL-epitopes", Vaccine, Jun. 1999, 18, 681-691.
Gao et al., "HCV-NS3 Thi minigene vaccine based on invariant chain CLIP genetic substitution enhances CD4+ Th1 cell responses in vivo", Vaccine, Apr. 2006, 24, 5491-5497.
Li et al., "IL-21 Influences the Frequency, Phenotype, and Affinity of the Antigen-Specific CD8 T Cell Response", J Immunol, Aug. 2005, 2261-2269.
Toes et al., "Protective anti-tum or immunity induced by vaccination with recombinant adenoviruses encoding multiple tumor-associated cytotoxic T lymphocyte epitopes in a string-of-beads fashion", Proc Natl Acad Sci, 1997, 94, 14660-65.

* cited by examiner

*Primary Examiner* — Elly-Gerald Stoica
(74) *Attorney, Agent, or Firm* — Baker & Hostetler LLP

(57) ABSTRACT

What is described is a novel genetic screen, involving recombinant technology and class I antigen cross-presentation, to search for supraoptimal superagonists of the 27L MART-1 mutant selecting for single amino acid substitution mutants of 27L that activate human antigen-specific CTL clones recognizing the wild-type MART-$1_{26\text{-}35}$ epitope. Three novel mutant epitopes are identified with superagonist properties that are functionally superior to 27L. The ability of a given analog to act as superagonist varies among patients. Also described is the use of methods to establish panels of potential superagonist APLs to individualize tumor peptide vaccines among patients. The methodology is replicated to identify APL to NY-ESO-$1_{157\text{-}165}$ and NY-ESO-$1_{157\text{-}170}$ tumor epitopes. A general method is described that is useful to produce a tumor vaccine to any tumor epitope.

15 Claims, 8 Drawing Sheets

US 9,314,516 B2

CONDITIONAL SUPERAGONIST CTL LIGANDS FOR THE PROMOTION OF TUMOR-SPECIFIC CTL RESPONSES

CROSS-REFERENCE TO RELATED APPLICATIONS

This application is a national phase application under 35 U.S.C. 371 of International Application Number PCT/US2011/035272, filed May 4, 2011, which claims priority to U.S. provisional application No. 61/331,260, filed May 4, 2010, which is hereby incorporated by reference in its entirety.

This invention was made with government support under CA122904 awarded by the National Institutes of Health and National Cancer Institute. The government has certain rights to the invention.

SEQUENCE LISTING

The instant application contains a Sequence Listing which has been submitted electronically in ASCII format and is hereby incorporated by reference in its entirety. Said ASCII copy, created on Apr. 11, 2014, is named 105003.000128_SL.txt and is 69,434 bytes in size.

TECHNICAL FIELD

What is described is a method of identifying antigens for a cancer vaccine, and specific polypeptides and polynucleotides useful in producing vaccines against cells having NY-ESO-$1_{157-165}$, NYE-ESO-$1_{157-170}$, or MART-$1_{26-35}$ tumor epitopes.

BACKGROUND

Cytotoxic T lymphocytes can directly kill malignant cells, which express and display specific antigenic peptides in the context of specific class I MHC molecules. These antigenic peptides, often referred to as CTL epitopes, are peptides of unique amino acid sequence, usually 9-11 amino acids in length. The tumor-associated antigenic peptide that is being targeted can be used as a peptide-based vaccine to promote the anti-tumor CTL response. However, when the target peptide is derived from non-mutated differentiation antigens as is often the case (e.g. melanosomal proteins), it can be insufficient to engender robust and sustained anti-tumor CTL responses. This is a result of immune tolerance mechanisms that generally suppress or eliminate high avidity auto-reactive T cells. As a result of these mechanisms, the vast majority of tumor-specific CTL, specifically those that recognize non-mutated tumor-associated antigens, are eliminated in the thymus and in the periphery. What remains is a low frequency of tumor-specific CTL, and/or CTL that bear low avidity T cell receptors for the cognate tumor antigen.

One way to activate and mobilize these rare and low avidity tumor-specific CTL is with the use of superagonist altered peptide ligands (APLs). These are mutant peptide ligands that deviate from the native peptide sequence by one or more amino acids, and which activate specific CTL clones more effectively than the native epitope. These alterations either allow the peptide to bind better to the restricting class I MHC molecule or interact more favorably with the TCR of a given tumor-specific CTL subset. Superagonist APLs demonstrate favorable responses in clinical studies.

One method to identify superagonist APLs involves comparing the amino acid sequence of the tumor-associated CTL epitope to the so-called consensus binding motif for the restricting class I MHC allotype. Where the tumor-associated epitope deviates from the consensus sequence, the appropriate amino acids can be substituted, allowing the peptide to bind better to the class I MHC molecule. This approach is limited because not all poorly stimulatory CTL epitopes deviate from the consensus motif. Another approach involves substituting one or more specific amino acids into every position of the epitope; e.g., alanine scanning. Another approach includes making every single amino acid substitution at one or two positions—positions either predicted to play a role in class I MHC secondary binding or to be directly involved in engaging the TCR. All of these approaches are severely limited in scope, and potentially overlook a large number of superagonist APLs. Utilization of APLs remains limited due to a lack of comprehensive methods for which to identify them.

SUMMARY

One aspect of the invention is a method of identifying an altered peptide ligand (APL) for eliciting response of regulator or effector CD4 or CD8 T cells against a tumor epitope, consisting of the steps of:
i. preparing saturation mutagenesis oligonucleotides encoding APLs;
ii. cloning said oligonucleotides in an expression vector;
iii. separating APL expressed by a clone from other cellular proteins;
iv. treat the T cells with the APL; and
v. identifying a superagonist APL that maximally stimulates the T cells.

An embodiment of the method, is a further step of screening the APLs for the ability to activate epitope-specific CTL clones. Another embodiment is the method in which the APLs are cross-presented to CTL clones on class I MHC molecules by immature dendritic cells. Another embodiment is the method wherein the oligonucleotides are cloned into bacteria. Another embodiment is wherein the bacteria are grown in 5 ml cultures, preferably less than 1 ml and preferably more than 0.2 ml. Another is the method, wherein the APL stimulates T cells to produce interferon-γ.

Another aspect of the method is wherein the tumor epitope is selected from the group consisting of SEQ ID NOS:1-351. An embodiment of the method is wherein the tumor epitope is NYESO-$1_{157-165}$ (SEQ ID NO:366), NYESO-$1_{157-170}$ (SEQ ID NO:367) or MART-$1_{26-35}$ (SEQ ID NO:361). Another embodiment is the superagonist APL identified by use of these tumor epitopes. Another embodiment is the method, wherein a panel of superagonist APLs are identified.

Another aspect of the invention is the superagonist APL identified according to the method, including SEQ ID NOS: 362-365 and 368-375. One or more APL is useful as a component in an antitumor vaccine. An embodiment is a panel of superagonist APLs, consisting of two or more APLs.

Another aspect of the invention is a method of using the superagonist APL by combining it with cells of a patient. An embodiment is a method by which the superagonist APL is administered to the patient. In this context, the superagonist APL may be used in an anti-tumor vaccine, in adoptive immunotherapy to generate T cell clonotypes, and/or to alter the phenotype of regulatory T cells to more effectively activate anti-tumor T cells. This embodiment of the invention may involve cells of the patient being treated ex vivo.

Another aspect of the invention is the method of stimulating T cells with an APL or APL panel, wherein the CD4 T cells are one or more T cells selected from the group consisting of Th1, Th2, Th9, and Th17 cells.

Another aspect of the invention is a superagonist APL selected from the group consisting of SEQ:362-365 and 368-376. An embodiment of the invention is a panel of superagonist APLs selected from the group consisting of SEQ:362-365 and 368-376.

Another aspect of the invention is an APL minigene, comprising a nucleotide sequence selected from the group consisting of SEQ ID NO:382-391 and 377-381. An embodiment of the invention is a use of the APL minigene to express the minigene in a human cell, preferably a cell of a patient, most preferably, a cell from a patient with a cancer or cancer precursor, a graft versus host disease, or an autoimmune condition.

BRIEF DESCRIPTION OF THE DRAWINGS

FIG. 3B shows the IFN-γ activity elicited by individual clones, relative to the activity elicited by A27L. The clones that were initially assayed together are indicated by shading. A bold number indicates the APL clone which is most responsible for the activation of the screening CTL clone. DNA sequence analysis was used to determine the amino acid encoded.

DETAILED DESCRIPTION OF ILLUSTRATIVE EMBODIMENTS

Figure 1:
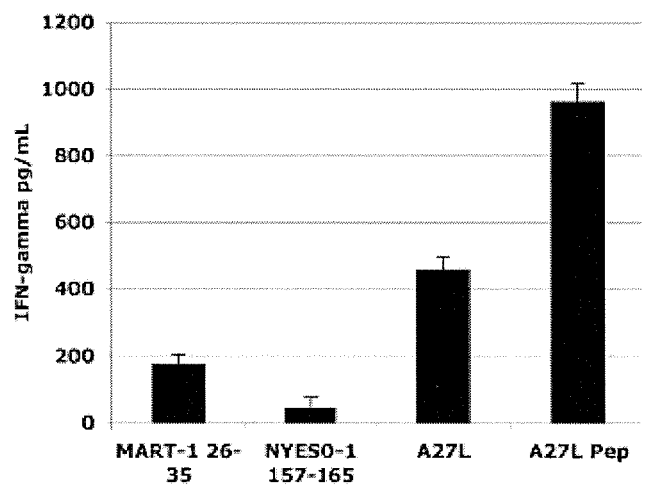
FIG. 1. Native and superagonist CTL determinants can be distinguished in bead-based cross presentation assay. Oligonucleotides encoding MART-1$_{26-35}$, NY-ESO-1$_{157-165}$, or MART-1$_{26-35}$A27L were cloned into and expressed by pQE40 expression vectors in 5 ml bacterial cultures. The mini-gene products were isolated and "fed" to immature dendritic cells as described in the Examples. MART-1$_{26-35}$-specific CTL clones were used to detect the presence of the cross-presented mini-gene products. Induced IFN-γ expression was determined by standard sandwich ELISA. A27L synthetic peptide (SEQ ID NO:362) at 1 μM was used a positive control.

What is described herein is a method to screen for potential superagonist APLs of a clinically relevant tumor-associated antigen, including NY-ESO-1 and MART-1. Rather than screening a limited subset of possible agonists, this technique allows screening of every single amino acid mutant of tumor epitope in a rapid and cost-effective manner. This approach to identifying APLs is effective, given the difference even subtle amino acid substitutions have on specific T cell response. Since superagonist APL structure cannot be predicted, the method described generates candidate APLS by a comprehensive screening technique.

Another aspect of unpredictability is that a given agonist APL may be more or less effective for different patients. While a given agonist APL might have a high stimulatory capacity for one patient it could be relatively ineffective for another patient. Apparently, different clones are being mobilized with different agonist peptides. This heightens the need for panels of superagonist APLs for use in a therapeutic setting.

Tumor-Specific Epitopes

Unique antigens result from point mutations in genes that are expressed ubiquitously. The mutation usually affects the coding region of the gene and is unique to the tumor of an individual patient or restricted to very few patients. Antigens that are strictly tumor-specific may play an important role in the natural anti-tumor immune response of individual patients. These are listed in Table 1.

These epitopes are characteristic of lung carcinoma, melanoma, chronic myeloid leukemia, colorectal carcinoma, gastric carcinoma, endometrial carcinoma, head and neck squamous cell carcinoma, lung squamous cell carcinoma, renal cell carcinoma, bladder tumor, non-small cell lung carcinoma, head and neck squamous cell carcinoma, pancreatic adenocarcinoma, sarcoma, promyelocytic leukemia, myeloid leukemia, acute lymphoblastic leukemia, acute myelogenous leukemia, breast cancer, and prostate carcinoma.

Each epitope is associated with a particular HLA haplotype, either a class I or class II MHC antigen, as shown in Tables 1-4.

TABLE 1

Unique antigens

| Gene/protein | HLA haplotype | Peptide$^c$ | Position | SEQ ID NO |
|---|---|---|---|---|
| alpha-actinin-4 | A2 | FIASNGVKLV | 118-127 | 1 |
| ARTC1 | DR1 | YSVYFNLPADTIYTN | | 2 |
| BCR-ABL fusion protein (b3a2) | A2 | SSKALQRPV | 926-934 | 3 |
| | B8 | GFKQSSKAL | 922-930 | 392 |
| | DR4 | ATGFKQSSKALQRPVAS | 920-936 | 393 |
| | DR9 | ATGFKQSSKALQRPVAS | 920-936 | 394 |
| B-RAF | DR4 | EDLTVKIGDFGLATEKSRWSGSHQFEQLS | 586-614 | 4 |
| CASP-5 | A2 | FLIIWQNTM | 67-75 | 5 |
| CASP-8 | B35 | FPSDSWCYF | 476-484 | 6 |
| beta-catenin | A24 | SYLDSGIHF | 29-37 | 7 |
| Cdc27 | DR4 | FSWAMDLDPKGA | 760-771 | 8 |
| CDK4 | A2 | ACDPHSGHFV | 23-32 | 9 |
| CDKN2A | A11 | AVCPWTWLR | 125-133 (p14ARF-ORF3) 111-119 (p16INK4a-ORF3) | 10 |
| COA-1 | DR4 | TLYQDDTLTLQAAG | 371-384 | 11 |
| | DR13 | TLYQDDTLTLQAAG | 371-384 | 413 |
| dek-can fusion protein | DR53 | TMKQICKKEIRRLHQY | 342-357 | 12 |
| EFTUD2 | A3 | KILDAVVAQK | 668-677 | 13 |
| Elongation factor 2 | A68 | ETVSEQSNV | 581-589 | 14 |
| ETV6-AML1 fusion protein | A2 | RIAECILGM | 334-342 | 15 |
| | DP5 | IGRIAECILGMNPSR | 332-346 | 16 |
| | DP17 | IGRIAECILGMNPSR | 332-346 | 414 |
| FLT3-ITD | A1 | YVDFREYEYY | 591-600 | 17 |
| FN1 | DR2 | MIFEKHGFRRTTPP | 2050-2063 | 18 |
| GPNMB | A3 | TLDWLLQTPK | 179-188 | 19 |
| LDLR-fucosyltransferase AS fusion protein | DR1 | WRRAPAPGA | 315-323 | 20 |
| | DR1 | PVTWRRAPA | 312-320 | 21 |
| hsp70-2 | A2 | SLFEGIDIYT | 286-295 | 22 |
| KIAA0205 | B44 | AEPINIQTW | 262-270 | 23 |
| MART2 | A1 | FLEGNEVGKTY | 446-455 | 24 |
| ME1 | A2 | FLDEFMEGV | 224-232 | 25 |
| MUM-1$^f$ | B44 | EEKLIVVLF | 30-38 | 26 |
| MUM-2 | B44 | SELFRSGLDSY | 123-133 | 27 |
| | Cw6 | FRSGLDSYV | 126-134 | 28 |

TABLE 1-continued

Unique antigens

| Gene/protein | HLA haplotype | Peptide<sup>c</sup> | Position | SEQ ID NO |
|---|---|---|---|---|
| MUM-3 | A68 | EAFIQPITR | 322-330 | 29 |
| neo-PAP | DR7 | RVIKNSIRLTL | 724-734 | 30 |
| Myosin class I | A3 | KINKNPKYK | 911-919 | 31 |
| NFYC | B52 | QQITKTEV | 275-282 | 32 |
| OGT | A2 | SLYKFSPFPL | 28-37 | 33 |
| OS-9 | B44 | KELEGILLL | 438-446 | 34 |
| p53 | A2 | VVPCEPPEV | 217-225 | 35 |
| pml-RAR alpha fusion protein | DR11 | NSNHVASGAGEAAIETQSSSSEEIV | | 36 |
| PRDX5 | A2 | LLLDDLLVSI | 163-172 | 37 |
| PTPRK | DR10 | PYYFAAELPPRNLPEP | 667-682 | 38 |
| K-ras | B35 | VVVGAVGVG | 7-15 | 39 |
| N-ras | A1 | ILDTAGREEY | 55-64 | 40 |
| RBAF600 | B7 | RPHVPESAF | 329-337 | 41 |
| SIRT2 | A3 | KIFSEVTLK | 192-200 | 42 |
| SNRPD1 | B38 | SHETVIIEL | 11-19 | 43 |
| SYT-SSX1 or -SSX2 fusion protein | B7 | QRPYGYDQIM | 402-410 (SYT) 111-112(SSX2) | 44 |
| TGF-betaRII | A2 | RLSSCVPVA | 131-139 | 45 |
| Triosephosphate isomerase | DR1 | GELIGILNAAKVPAD | 23-37 | 46 |

Shared antigens are present on many independent tumors. One group corresponds to peptides encoded by "cancer-germline" genes that are expressed in many tumors but not in normal tissues. Some are listed in Table 2.

TABLE 2

Shared tumor-specific antigens

| Gene | HLA | Peptide | Position | SEQ ID NO: |
|---|---|---|---|---|
| 4BAGE-1 | Cw16 | AARAVFLAL | 2-10 | 47 |
| GAGE-1,2,8 | Cw6 | YRPRPRRY | 9-16 | 48 |
| GAGE-3,4,5,6,7 | A29 | YYWPRPRRY | 10-18 | 49 |
| GnTV<sup>f</sup> | A2 | VLPDVFIRC(V) | intron | 50 |
| HERV-K-MEL | A2 | MLAVISCAV | 1-9 | 51 |
| KK-LC-1 | B15 | RQKRILVNL | 76-84 | 52 |
| KM-HN-1 | A24 | NYNNFYRFL | 196-204 | 53 |
| | A24 | EYSKECLKEF | 499-508 | 54 |
| | A24 | EYLSLSDKI | 770-778 | 55 |
| LAGE-1 | A2 | MLMAQEALAFL | ORF2 (1-11) | 56 |
| | A2 | SLLMWITQC | 157-165 | 57 |
| | A31 | LAAQERRVPR | ORF2 (18-27) | 58 |
| | A68 | ELVRRILSR | 103-111 | 59 |

TABLE 2-continued

Shared tumor-specific antigens

| Gene | HLA | Peptide | Position | SEQ ID NO: |
|---|---|---|---|---|
| | B7 | APRGVRMAV | ORF2 (46-54) | 60 |
| | DP4 | SLLMWITQCFLPVF | 157-170 | 61 |
| | DR3 | QGAMLAAQERRVPRAAEVPR | ORF2 (14-33) | 62 |
| | DR4 | AADHRQLQLSISSCLQQL | 139-156 | 63 |
| | DR11 | CLSRRPWKRSWSAGSCPGMPHL | ORF2 (81-102) | 64 |
| | DR12 | CLSRRPWKRSWSAGSCPGMPHL | ORF2 (81-102) | 65 |
| | DR13 | ILSRDAAPLPRPG | 108-120 | 66 |
| | DR15 | AGATGGRGPRGAGA | 37-50 | 67 |
| MAGE-A1 | A1 | EADPTGHSY | 161-169 | 68 |
| | A2 | KVLEYVIKV | 278-286 | 69 |
| | A3 | SLFRAVITK | 96-104 | 70 |
| | A68 | EVDGREHSA | 222-231 | 71 |
| | B7 | RVRFFFPSL | 289-298 | 72 |
| | B35 | EADPTGHSY | 161-169 | 73 |
| | B37 | REPVTKAEML | 120-129 | 74 |
| | B53 | DPARYEFLW | 258-266 | 75 |
| | B57 | ITKKVADLVGF | 102-112 | 76 |
| | Cw2 | SAFPTTINF | 62-70 | 77 |
| | Cw3 | SAYGEPRKL | 230-238 | 78 |
| | Cw16 | SAYGEPRKL | 230-238 | 79 |
| | DP4 | TSCILESLFRAVITK | 90-104 | 80 |
| | DP4 | PRALAETSYVKVLEY | 268-282 | 81 |
| | DR13 | FLLLKYRAREPVTKAE | 112-127 | 82 |
| | DR15 | EYVIKVSARVRF | 281-292 | 83 |
| MAGE-A2 | A2 | YLQLVFGIEV | 157-166 | 84 |
| | A24 | EYLQLVFGI | 156-164 | 85 |
| | B37 | REPVTKAEML | 127-136 | 86 |
| | Cw7 | EGDCAPEEK | 212-220 | 87 |
| | DR13 | LLKYRAREPVTKAE | 121-134 | 88 |
| MAGE-A3 | A1 | EVDPIGHLY | 168-176 | 89 |
| | A2 | FLWGPRALV | 271-279 | 90 |
| | A2 | KVAELVHFL | 112-120 | 91 |
| | A24 | TFPDLESEF | 97-105 | 92 |
| | A24 | VAELVHFLL | 113-121 | 93 |
| | B18 | MEVDPIGHLY | 167-176 | 94 |
| | B35 | EVDPIGHLY | 168-176 | 95 |
| | B37 | REPVTKAEML | 127-136 | 96 |
| | B40 | AELVHFLLL | 114-122 | 97 |
| | B44 | MEVDPIGHLY | 167-176 | 98 |
| | B52 | WQYFFPVIF | 143-151 | 99 |
| | Cw7 | EGDCAPEEK | 212-220 | 100 |
| | DP4 | KKLLTQHFVQENYLEY | 243-258 | 101 |
| | DQ6 | KKLLTQHFVQENYLEY | 243-258 | 102 |
| | DR1 | ACYEFLWGPRALVETS | 267-282 | 103 |
| | DR4 | VIFSKASSSLQL | 149-160 | 104 |
| | DR7 | VIFSKASSSLQL | 149-160 | 105 |
| | DR11 | GDNQIMPKAGLLIIV | 191-205 | 106 |
| | DR11 | TSYVKVLHHMVKISG | 281-295 | 107 |
| | DR13 | RKVAELVHFLLLKYRA | 111-126 | 108 |
| | DR13 | FLLLKYRAREPVTKAE | 119-134 | 109 |
| MAGE-A4 | A1 | EVDPASNTY | 169-177 | 110 |
| | A2 | GVYDGREHTV | 230-239 | 111 |
| | A24 | NYKRCFPVI | 143-151 | 112 |
| | B37 | SESLKMIF | 156-163 | 113 |
| MAGE-A6 | A34 | MVKISGGPR | 290-298 | 114 |
| | B35 | EVDPIGHVY | 168-176 | 115 |
| | B37 | REPVTKAEML | 127-136 | 116 |
| | Cw7 | EGDCAPEEK | 212-220 | 117 |
| | Cw16 | ISGGPRISY | 293-301 | 118 |
| | DR13 | LLKYRAREPVTKAE | 121-134 | 119 |
| MAGE-A9 | A2 | ALSVMGVYV | 223-231 | 120 |
| MAGE-A10 | A2 | GLYDGMEHL | 254-262 | 121 |
| | B53 | DPARYEFLW | 290-298 | 122 |

TABLE 2-continued

Shared tumor-specific antigens

| Gene | HLA | Peptide | Position | SEQ ID NO: |
|---|---|---|---|---|
| MAGE-A12 | A2[g] | FLWGPRALV | 271-279 | 123 |
| | Cw7 | VRIGHLYIL | 170-178 | 124 |
| | Cw7 | EGDCAPEEK | 212-220 | 125 |
| | DP4 | REPFTKAEMLGSVIR | 127-141 | 126 |
| | DR13 | AELVHFLLLKYRAR | 114-127 | 127 |
| MAGE-C2 | A2 | LLFGLALIEV | 191-200 | 128 |
| | A2 | ALKDVEERV | 336-344 | 129 |
| | B44 | SESIKKKVL | 307-315 | 130 |
| mucin[k] | | PDTRPAPGSTAPPAHGVTSA | | 131 |
| NA88-A | B13 | QGQHFLQKV | | 132 |
| NY-ESO-1/LAGE-2 | A2 | SLLMWITQC | 157-165 | 133 |
| | A2 | MLMAQEALAFL | ORF2 (1-11) | 134 |
| | A31 | ASGPGGGAPR | 53-62 | 135 |
| | A31 | LAAQERRVPR | ORF2 (18-27) | 136 |
| | A68 | TVSGNILTIR | 127-136 | 137 |
| | B7 | APRGPHGGAASGL | 60-72 | 138 |
| | B35 | MPFATPMEA | 94-102 | 139 |
| | B49 | KEFTVSGNILTI | 124-135 | 140 |
| | B51 | MPFATPMEA | 94-102 | 141 |
| | Cw3 | LAMPFATPM | 92-100 | 142 |
| | Cw6 | ARGPESRLL | 80-88 | 143 |
| | DP4 | SLLMWITQCFLPVF | 157-170 | 144 |
| | DP4 | LLEFYLAMPFATPMEAELARRSLAQ | 87-111 | 145 |
| | DR1 | LLEFYLAMPFATPMEAELARRSLAQ | 87-111 | 146 |
| | DR1 | EFYLAMPFATPM | 89-100 | 147 |
| | DR2 | RLLEFYLAMPFA | 86-97 | 148 |
| | DR3 | QGAMLAAQERRVPRAAEVPR | ORF2 (14-33) | 149 |
| | DR4 | PGVLLKEFTVSGNILTIRLT | 119-138 | 150 |
| | DR4 | VLLKEFTVSG | 121-130 | 151 |
| | DR4 | AADHRQLQLSISSCLQQL | 139-156 | 152 |
| | DR4 | LLEFYLAMPFATPMEAELARRSLAQ | 87-111 | 153 |
| | DR7 | PGVLLKEFTVSGNILTIRLTAADHR | 119-143 | 154 |
| | DR7 | LLEFYLAMPFATPMEAELARRSLAQ | 87-111 | 155 |
| | DR15 | AGATGGRGPRGAGA | 37-50 | 156 |
| SAGE | A24 | LYATVIHDI | 715-723 | 157 |
| Sp17 | A1 | ILDSSEEDK | 103-111 | 158 |
| SSX-2 | A2 | KASEKIFYV | 41-49 | 159 |
| | DP1 | EKIQKAFDDIAKYFSK | 19-34 | 160 |
| | DR3 | WEKMKASEKIFYVYMKRK | 37-54 | 161 |
| | DR4 | KIFYVYMKRKYEAMT | 45-59 | 162 |
| | DR11 | KIFYVYMKRKYEAM | 45-58 | 163 |
| SSX-4 | DP10 | INKTSGPKRGKHAWTHRLRE | 151-170 | 164 |
| | DR3 | YFSKKEWEKMKSSEKIVYVY | 31-50 | 165 |
| | DR8 | MKLNYEVMTKLGFKVTLPPF | 51-70 | 166 |
| | DR8 | KHAWTHRLRERKQLVVYEEI | 161-180 | 167 |
| | DR11 | LGFKVTLPPFMRSKRAADFH | 61-80 | 168 |
| | DR15 | KSSEKIVYVYMKLNYEVMTK | 41-60 | 169 |
| | DR52 | KHAWTHRLRERKQLVVYEEI | 161-180 | 170 |
| TAG-1 | A2 | SLGWLFLLL | 78-86 | 171 |
| | B8 | LSRLSNRLL | 42-50 | 172 |
| TAG-2 | B8 | LSRLSNRLL | 42-50 | 173 |
| TRAG-3 | DR1 | CEFHACWPAFTVLGE | 34-48 | 174 |
| | DR4 | CEFHACWPAFTVLGE | 34-48 | 175 |
| | DR7 | CEFHACWPAFTVLGE | 34-48 | 176 |
| TRP2-INT2[g] | A68 | EVISCKLIKR | intron 2 | 177 |
| XAGE-1b | DR9 | CATWKVICKSCISQTPG | 33-49 | 178 |

A second group of shared tumor antigens, named differentiation antigens, are also expressed in the normal tissue of origin of the malignancy. Antigens of this group are not tumor-specific, and their use as targets for cancer immunotherapy may result in autoimmunity towards the corresponding normal tissue. Autoimmune toxicity should not be an issue, however, in situations where the tissue expressing the antigen is dispensable or even resected by the surgeon in the course of cancer therapy, as would be the case for prostate specific antigen (PSA). These antigens are listed in Table 3.

TABLE 3

Differentiation antigens

| Gene/protein | HLA[a] | Peptide | Position | SEQ ID NO: |
|---|---|---|---|---|
| CEA | A2 | YLSGANLNL | 605-613 | 179 |
|  | A2 | IMIGVLVGV | 691-699 | 180 |
|  | A2 | GVLVGVALI | 694-702 | 181 |
|  | A3 | HLFGYSWYK | 61-69 | 182 |
|  | A24 | QYSWFVNGTF | 268-277 | 183 |
|  | A24 | TYACFVSNL | 652-660 | 184 |
|  | DR3 | AYVCGIQNSVSANRS | 568-582 | 185 |
|  | DR4 | DTGFYTLHVIKSDLVNEEATGQFRV | 116-140 | 186 |
|  | DR4 | YSWRINGIPQQHTQV | 625-639 | 187 |
|  | DR7 | TYYRPGVNLSLSC | 425-437 | 188 |
|  | DR7 | EIIYPNASLLIQN | 99-111 | 189 |
|  | DR9 | YACFVSNLATGRNNS | 653-667 | 190 |
|  | DR11 | LWWVNNQSLPVSP | 177-189 and 355-367 | 191 |
|  | DR13 | LWWVNNQSLPVSP | 177-189 and 355-367 | 192 |
|  | DR14 | LWWVNNQSLPVSP | 177-189 and 355-367 | 193 |
|  | DR14 | EIIYPNASLLIQN | 99-111 | 194 |
|  | DR14 | NSIVKSITVSASG | 666-678 | 195 |
| gp100/Pmel17 | A2 | KTWGQYWQV | 154-162 | 196 |
|  | A2 | (A)MLGTHTMEV | 177(8)-186 | 197 |
|  | A2 | ITDQVPFSV | 209-217 | 198 |
|  | A2 | YLEPGPVTA | 280-288 | 199 |
|  | A2 | LLDGTATLRL | 457-466 | 200 |
|  | A2 | VLYRYGSFSV | 476-485 | 201 |
|  | A2 | SLADTNSLAV | 570-579 | 202 |
|  | A2 | RLMKQDFSV | 619-627 | 203 |
|  | A2 | RLPRIFCSC | 639-647 | 204 |
|  | A3 | LIYRRRLMK | 614-622 | 205 |
|  | A3 | ALLAVGATK | 17-25 | 206 |
|  | A3 | IALNFPGSQK | 86-95 | 207 |
|  | A3 | ALNFPGSQK | 87-95 | 208 |
|  | A11 | ALNFPGSQK | 87-95 | 209 |
|  | A24 | VYFFLPDHL | intron 4 | 210 |
|  | A32 | RTKQLYPEW | 40-42 and 47-52 | 211 |
|  | A68 | HTMEVTVYHR | 182-191 | 212 |
|  | B7 | SSPGCQPPA | 529-537 | 213 |
|  | B35 | VPLDCVLYRY | 471-480 | 214 |
|  | B35 | LPHSSSHWL | 630-638 | 215 |
|  | Cw8 | SNDGPTLI | 71-78 | 216 |
|  | DQ6 | GRAMLGTHTMEVTVY | 175-189 | 217 |
|  | DR4 | WNRQLYPEWTEAQRLD | 44-59 | 218 |
|  | DR7 | TTEWVETTARELPIPEPE | 420-437 | 219 |
|  | DR7 | TGRAMLGTHTMEVTVYH | 174-190 | 220 |
|  | DR53 | GRAMLGTHTMEVTVY | 175-189 | 221 |
| Kallikrein 4 | DP4 | SVSESDTIRSISIAS | 125-139 | 222 |
|  | DR4 | LLANGRMPTVLQCVN | 155-169 | 223 |
|  | DR7 | RMPTVLQCVNVSVVS | 160-174 | 224 |
| mammaglobin-A | A3 | PLLENVISK | 23-31 | 225 |
| Melan-A/MART-1 | A2 | (E)AAGIGILTV | 26(27)-35 | 226 |
|  | A2 | ILTVILGVL | 32-40 | 227 |
|  | B35 | EAAGIGILTV | 26-35 | 228 |
|  | B45 | AEEAAGIGIL(T) | 24-33(34) | 229 |
|  | Cw7 | RNGYRALMDKS | 51-61 | 230 |
|  | DQ6 | EEAAGIGILTVI | 25-36 | 231 |
|  | DR1 | AAGIGILTVILGVL | 27-40 | 232 |
|  | DR3 | EEAAGIGILTVI | 25-36 | 233 |
|  | DR4 | RNGYRALMDKSLHVGTQCALTRR | 51-73 | 234 |
|  | DR11 | MPREDAHFIYGYPKKGHGHS | 1-20 | 235 |

TABLE 3-continued

Differentiation antigens

| Gene/protein | HLA$^a$ | Peptide | Position | SEQ ID NO: |
|---|---|---|---|---|
| | DR52 | KNCEPVVPNAPPAYEKLSAE | 91-110 | 236 |
| NY-BR-1 | A2 | SLSKILDTV | 904-912 | 237 |
| OA1 | A24 | LYSACFWWL | 126-134 | 238 |
| PSA | A2 | FLTPKKLQCV | 165-174 | 239 |
| | A2 | VISNDVCAQV | 178-187 | 240 |
| RAB38/NY-MEL-1 | A2 | VLHWDPETV | 50-58 | 241 |
| TRP-1/gp75 | A31 | MSLQRQFLR | alt. ORF | 242 |
| | DR4 | ISPNSVFSQWRVVCDSLEDYD | 277-297 | 243 |
| | DR15 | SLPYWNFATG | 245-254 | 244 |
| TRP-2 | A2 | SVYDFFVWL | 180-188 | 245 |
| | A2 | TLDSQVMSL | 360-368 | 246 |
| | A31 | LLGPGRPYR | 197-205 | 247 |
| | A33 | LLGPGRPYR | 197-205 | 248 |
| | Cw8 | ANDPIFVVL | 387-395 | 249 |
| | DR3 | QCTEVRADTRPWSGP | 60-74 | 250 |
| | DR15 | ALPYWNFATG | 241-250 | 251 |
| tyrosinase | A1 | KCDICTDEY | 243-251 | 252 |
| | A1 | SSDYVIPIGTY | 146-156 | 253 |
| | A2 | MLLAVLYCL | 1-9 | 254 |
| | A2 | CLLWSFQTSA | 8-17 | 255 |
| | A2 | YMDGTMSQV | 369-377 | 256 |
| | A24 | AFLPWHRLF | 206-214 | 257 |
| | A26 | QCSGNFMGF | 90-98 | 258 |
| | B35 | TPRLPSSADVEF | 309-320 | 259 |
| | B35 | LPSSADVEF | 312-320 | 260 |
| | B38 | LHHAFVDSIF | 388-397 | 261 |
| | B44 | SEIWRDIDF | 192-200 | 262 |
| | DR4 | QNILLSNAPLGPQFP | 56-70 | 263 |
| | DR4 | SYLQDSDPDSFQD | 450-462 | 264 |
| | DR15 | FLLHHAFVDSIFEQWLQRHRP | 386-406 | 265 |

Shared antigens of the third group are expressed in a wide variety of normal tissues and overexpressed in tumors. Because a minimal amount of peptide is required for CTL recognition, a low level of expression in normal tissues may mean that autoimmune damage is not incurred. However, this threshold is difficult to define, as is the normal level of expression of those genes for each cell type. A list of these is in Table 4.

TABLE 4

Overexpressed antigens

| Gene | HLA$^a$ | Peptide | Position | SEQ ID NO: |
|---|---|---|---|---|
| adipophilin | A2 | SVASTITGV | 129-137 | 266 |
| AIM-2 | A1 | RSDSGQQARY | intron | 267 |
| ALDH1A1 | A2 | LLYKLADLI | 88-96 | 268 |
| BCLX (L) | A2 | YLNDHLEPWI | 173-182 | 269 |
| BING-4 | A2 | CQWGRLWQL | ORF2 | 270 |
| CALCA | A2 | VLLQAGSLHA | 16-25 | 271 |
| CPSF | A2 | KVHPVIWSL | 250-258 | 272 |
| | A2 | LMLQNALTTM | 1360-1369 | 273 |
| cyclin D1 | A2 | LLGATCMFV | 101-109 | 274 |
| | DR4 | NPPSMVAAGSVVAAV | 198-212 | 275 |
| DKK1 | A2 | ALGGHPLLGV | 20-29 | 276 |
| ENAH (hMena) | A2 | TMNGSKSPV | 502-510 | 277 |
| Ep-CAM | A24 | RYQLDPKFI | 173-181 | 278 |

TABLE 4-continued

Overexpressed antigens

| Gene | HLA<sup>a</sup> | Peptide | Position | SEQ ID NO: |
|---|---|---|---|---|
| EphA3 | DR11 | DVTFNIICKKCG | 356-367 | 279 |
| EZH2 | A2 | FMVEDETVL | 120-128 | 280 |
| | A2 | FINDEIFVEL | 165-174 | 281 |
| | A24 | KYDCFLHPF | 291-299 | 282 |
| | A24 | KYVGIEREM | 735-743 | 283 |
| FGF5 | A3 | NTYASPRFK | 172-176 and 204-207 | 284 |
| G250/MN/CAIX | A2 | HLSTAFARV | 254-262 | 285 |
| HER-2/neu | A2 | KIFGSLAFL | 369-377 | 286 |
| | A2 | IISAVVGIL | 654-662 | 287 |
| | A2 | ALCRWGLLL | 5-13 | 288 |
| | A2 | ILHNGAYSL | 435-443 | 289 |
| | A2 | RLLQETELV | 689-697 | 290 |
| | A2 | VVLGVVFGI | 665-673 | 291 |
| | A2 | YMIMVKCWMI | 952-961 | 292 |
| | A2 | HLYQGCQVV | 48-56 | 293 |
| | A2 | YLVPQQGFFC | 1023-1032 | 294 |
| | A2 | PLQPEQLQV | 391-399 | 295 |
| | A2 | TLEEITGYL | 402-410 | 296 |
| | A2 | ALIHHNTHL | 466-474 | 297 |
| | A2 | PLTSIISAV | 650-658 | 298 |
| | A3 | VLRENTSPK | 754-762 | 299 |
| | A24 | TYLPTNASL | 63-71 | 300 |
| IL13Ralpha2 | A2 | WLPFGFILI | 345-353 | 301 |
| Intestinal carboxyl esterase | B7 | SPRWWPTCL | alt. ORF | 302 |
| alpha-fetoprotein | A2 | GVALQTMKQ | 542-550 | 303 |
| | A2 | FMNKFIYEI | 158-166 | 304 |
| | DR13 | QLAVSVILRV | 364-373 | 305 |
| M-CSF | B35 | LPAVVGLSPGEQEY | alt. ORF | 306 |
| MCSP | DR11 | VGQDVSVLFRVTGALQ | 693-708 | 307 |
| mdm-2 | A2 | VLFYLGQY | 53-60 | 308 |
| Meloe | A2 | TLNDECWPA | 36-44 | 309 |
| MMP-2 | A2 | GLPPDVQRV | 560-568 | 310 |
| MMP-7 | A3 | SLFPNSPKWTSK | 96-107 | 311 |
| MUC1 | A2 | STAPPVHNV | 950-958 | 312 |
| | A2 | LLLLTVLTV | 12-20 | 313 |
| | DR3 | PGSTAPPAHGVT | repeated region | 314 |
| p53 | A2 | LLGRNSFEV | 264-272 | 315 |
| | A2 | RMPEAAPPV | 65-73 | 316 |
| | B46 | SQKTYQGSY | 99-107 | 317 |
| | DP5 | PGTRVRAMAIYKQ | 153-165 | 318 |
| | DR14 | HLIRVEGNLRVE | 193-204 | 319 |
| PAX5 | A2 | TLPGYPPHV | 311-319 | 320 |
| PBF | B55 | CTACRWKKACQR | 499-510 | 321 |
| PRAME | A2 | VLDGLDVLL | 100-108 | 322 |
| | A2 | SLYSFPEPEA | 142-151 | 323 |
| | A2 | ALYVDSLFFL | 300-309 | 324 |
| | A2 | SLLQHLIGL | 425-433 | 325 |
| | A24 | LYVDSLFFL | 301-309 | 326 |
| PSMA | A24 | NYARTEDFF | 178-186 | 327 |
| RAGE-1 | A2 | LKLSGVVRL | 352-360 | 328 |
| | A2 | PLPPARNGGL | 32-40 | 329 |
| | B7 | SPSSNRIRNT | 11-20 | 330 |

TABLE 4-continued

Overexpressed antigens

| Gene | HLA[a] | Peptide | Position | SEQ ID NO: |
|---|---|---|---|---|
| RGS5 | A2 | LAALPHSCL | 5-13 | 331 |
| | A3 | GLASFKSFLK | 74-83 | 332 |
| RhoC | A3 | RAGLQVRKNK | 176-185 | 333 |
| RNF43 | A2 | ALWPWLLMA(T) | 11-19(20) | 334 |
| | A24 | NSQPVWLCL | 721-729 | 335 |
| RU2AS | B7 | LPRWPPPQL | antisense | 336 |
| secernin 1 | A2 | KMDAEHPEL | 196-204 | 337 |
| SOX10 | A2 | AWISKPPGV | 332-340 | 338 |
| | A2 | SAWISKPPGV | 331-340 | 339 |
| STEAP1 | A2 | MIAVFLPIV | 292-300 | 340 |
| | A2 | HQQYFYKIPILVINK | 102-116 | 341 |
| survivin | A2 | ELTLGEFLKL | 95-104 | 342 |
| Telomerase | A2 | ILAKFLHWL | 540-548 | 343 |
| | A2 | RLVDDFLLV | 865-873 | 344 |
| | DR7 | RPGLLGASVLGLDDI | 672-686 | 345 |
| | DR11 | LTDLQPYMRQFVAHL | 766-780 | 346 |
| VEGF | B27 | SRFGGAVVR | —[i] | 347 |
| WT1 | A1 | TSEKRPFMCAY | 317-327 | 348 |
| | A24 | CMTWNQMNL | 235-243 | 349 |
| | DP5 | LSHLQMHSRKH | 337-347 | 350 |
| | DR4 | KRYFKLSHLQMHSRKH | 332-347 | 351 |

Mutagenesis

After selecting the particular tumor specific epitope, random amino acid substitutions are introduced. Oligonucleotide sequences encoding the peptide epitope are designed and cloned in an appropriate vector. Mutagenesis can be done according to the skill of the ordinary worker at each amino acid position of the peptide. The mutant may have substitutions at 1, 2, 3, 4, 5, 6 or more positions, depending on the particular epitope.

The positional libraries are designed such that the codon of interest is totally randomized (NNN), resulting in a pool of oligonucleotides which contains every given codon sequence. This mutagenesis approach might be likened to a slot machine which contains three positions (a codon) and each position has the same 4 possibilities (A, C, G, or T). When pulled, there is a 1 in 64 chance of getting any combination of 3. If pulled 100 times there is a high probability that every sequence will be represented (80% certainty, according to a Poisson distribution). Here, the 100 pulls represent 100 bacterial colonies, each containing a different mutant agonist peptide-encoding oligonucleotide. When cloned and expressed, each amino acid should be represented in a library of 100, with 80% certainty, according to a Poisson distribution. A positional library can be generated for each position (amino acid) of the target peptide. The APL minigene constructs are fused to a 6×-histidine tag (SEQ ID NO: 415), and can easily be separated from bacterial proteins on $Co^{2+}$-coated paramagnetic beads.

The mutagenized epitopes are preferentially expressed in cells as part of an expression vector, more preferentially as a fusion protein. The preferred host for the expression vector is bacterial, e.g., a strain of E. coli. Most preferred is an inducible expression system.

A mutant library is generated using the expression vector in the host cell. Preferentially, the library is distributed in liquid culture, most preferentially in 96 well plates. The cells accumulate a recombinant protein comprising the sequence of the mutagenized epitopes.

The recombinant protein is released and separated from the host cells. This can be done by lysing the cells to release the recombinant protein. Preferentially, the mutagenized epitope is separated from other cellular proteins by adding protein binding magnetic beads (e.g. 6×-histidine (SEQ ID NO: 415) specific magnetic beads) to cell lysates.

Screening

Initial screens can be done by combining beads containing recombinant mutagenized epitopes with dendritic cells and epitope-specific T cells and assaying for the production appropriate cytokines, including, but not limited to, interferon γ, interleukin-4, interleukin-10, and granulocyte macrophage colony-stimulating factor. That is, APLs are screened for the ability to activate epitope-specific T cell clones following cross-presentation of the bead-bound ligand on class I or class II MHC molecules by dendritic cells (DC).

Attempts by others to measure the functional avidity of tumor epitope-specific CTL generated via unmodified peptide with CTL generated via the analogs, have been hampered by the inability to generate $CD8^+$/MART-$1_{26-35}$-tetramer positive T cell populations using a peptide having the natural amino acid sequence of the epitope. Using the methods described herein, the superagonist APLs elicit different antigen-specific CTL responses from patient to patient, and that the CTL populations generated by APL stimulation are capable of effectively killing tumors. Thus these agonist APLs might be considered "conditional" superagonist ligands. Using unique tumor epitope-specific CTL clones in the initial screen that other potential superagonist peptides can be identified. Panels of potential tumor-associated super-agonist peptides may be assembled, to ensure that one or more APLs are effective at generating potent anti-tumor CTL responses from a given patient.

Efficacy

To determine how well the identified agonist APLs could prospectively generate tumor epitope-specific CTL populations from peripheral blood mononuclear cell (PBMC) of tumor patients, the APLs were used to stimulate different patient PBMC samples under standard in vitro conditions. Preferentially, cultures of PBMC are treated with the mutagenized epitope and incubated for at least one week. CTLs can readily be measured using ordinary methods. For example, cells can be stained with FITC-labeled anti-CD8 antibodies and APC-labeled HLA-matched complexes and analyzed by flow cytometry.

The ability of an APL to generate CD4 T cells from PBMC of tumor patients is also a measure of the efficacy of the mutagenized epitope.

It may be necessary to probe a panel of APLs since the ability of a single APL to stimulate cells of every patient having the specific tumor cannot be assumed at the outset of measurements.

One aspect of the utility of the APLs lies in their ability to stimulate T cells of a cancer patient ex vivo or in vivo. The stimulated T cells are effector and regulator $CD4^+$ cells, including Th1, Th2, Th9 and/or Th17 cells. The stimulation can involve use of the APLs as purified peptides, or as intra-cellular products of APL minigenes. APL minigenes may also be expressed as a string of beads, i.e., multiple CTL genes within the same expression vector, or as part of a T helper protein as described in Fomsgaard et al., 1999 Vaccine 18:681-91; Ann et al., 1997 J Virol 1192-302; Toes et al., 1997 Proc Natl Acad Sci 94:14660-65; Gao et al., 2006 Vaccine 24:5491-97, hereby incorporated by reference in their entirety.

The potential use for these novel antigenic peptides includes their use in anti-tumor vaccine studies; use in adoptive immunotherapy to generate a wider array of anti-tumor $CD4^+$ T cell clonotypes; the ability to alter the phenotype of T regulatory cells in order to more effectively activate anti-tumor $CD4^+$ T cells.

EXAMPLES

Example 1

Oligonucleotides were designed to have a complimentary 5' KpnI site and a complimentary 3' PstI site. The sequences of the saturation mutagenesis sense strands of the $MART-1_{26-35}$ positional oligonucleotides are shown in Table 5 (each sense strand has a corresponding mutant antisense strand):

TABLE 5

| $MART-1_{26-35}$ Library | SEQ ID NO: | Sense strand of $MART-1_{26-35}$ positional Saturation Mutagenesis Oligonucleotides |
|---|---|---|
| P1 | 352 | CATCGAGGGAAGGNNNCTCGCCGGAATCGGCATTCTGACCGTTTAATGAATTCTGCA |
| P2 | 353 | CATCGAGGGAAGGGAGNNNGCCGGAATCGGCATTCTGACCGTTTAATGAATTCTGCA |
| P3 | 354 | CATCGAGGGAAGGCAGCTCNNNGGAATCGGCATTCTGACCGTTTAATGAATTCTGCA |
| P4 | 355 | CATCGAGGGAAGGCAGCTCGCCNNNATCGGCATTCTGACCGTTTAATGAATTCTGCA |
| P5 | 356 | CATCGAGGGAAGGCAGCTCGCCGGANNNGGCATTCTGACCGTTTAATGAATTCTGCA |
| P6 | 357 | CATCGAGGGAAGGCAGCTCGCCGGAATCNNNATTCTGACCGTTTAATGAATTCTGCA |
| P7 | 358 | CATCGAGGGAAGGCAGCTCGCCGGAATCGGCNNNCTGACCGTTTAATGAATTCTGCA |
| P8 | 359 | CATCGAGGGAAGGCAGCTCGCCGGAATCGGCATTNNNACCGTTTAATGAATTCTGCA |
| P9 | 360 | CATCGAGGGAAGGCAGCTCGCCGGAATCGGCATTCTGNNNGTTTAATGAATTCTGCA |

NNN represents totally randomized codons, any one of sixty-four codons. In a given positional library consisting of 100 mutant oligonucleotide pairings, each codon has high likelihood of being represented.

Variant polypeptide sequences are listed in Table 6.

TABLE 6

| Designation | Sequence | SEQ ID NO |
|---|---|---|
| Mart-1 | EAAGIGILTV | 228 |
| A27L | ELAGIGILTV | 362 |
| E26G | GLAGIGILTV | 363 |
| E26S | SLAGIGILTV | 364 |
| L33M | ELAGIGIMTV | 365 |

Similarly, nucleotides encoding variant sequences of $NY-ESO-1_{157-170}$ (SEQ ID NO:144) were synthesized that encoded the following sequences (Table 7).

TABLE 7

| Designation | Sequence | SEQ ID NO: |
|---|---|---|
| $NY-ESO-1_{157-165}$ WT | SLLMWITQC | 366 |
| $NY-ESO-1_{157-170}$ WT | SLLMWITQCFLPVF | 144 |
| W161I (NYII-51) | SLLMIITQCFLPVF | 368 |

TABLE 7-continued

| Designation | Sequence | SEQ ID NO: |
|---|---|---|
| W161F | SLLMFITQCFLPVF | 369 |
| I162R | SLLMWRTQCFLPVF | 370 |
| I162M | SLLMWMTQCFLPVF | 371 |
| I162Q (NYII-6Q) | SLLMWQTQCFLPVF | 372 |
| 1162V | SLLMWVTQCFLPVF | 373 |
| Q164S (NYII-8S) | SLLMWITSCFLPVF | 374 |
| F170W (NYII-14W) | SLLMWITQCFLPVW | 375 |
| NY-ESO-1 C165V | SLLMWITQVF | 376 |

Synthetic polypeptides having these sequences were suspended in DMSO.

Example 2

The saturation mutagenesis oligonucleotides were cloned into the expression vector pQE40 (Qiagen). The plasmids were transformed into *E. coli* (M15 pREP). Mini-gene products were expressed as fusion proteins containing 6×-histidine tags (SEQ ID NO: 415). Following recombinant protein induction, bacteria were lysed with 8M Urea, pH 8.0. Lysate was harvested and applied to $Mg^{2+}$ coated paramagnetic beads (Talon beads, Dynal), which bind specifically to 6×-histidine (SEQ ID NO: 415).

For saturation mutagenesis libraries, bacterial clones were cultured individually in wells of 96-well plates.

Melanoma cell lines A375 and Mel 526, CTL clones and the TAP-deficient cell line T2 were maintained in RPMI 1640, containing 25 mM HEPES, 2 mM L-glutamine, 50 U/ml penicillin, 50 mg/ml streptomycin and 10% human serum from normal donors. Dendritic cells were prepared from adherent monocytes, isolated from the PBMC of HLA-$A2^+$ healthy donors. IL-4 (500 U/mL; R&D Systems, Minneapolis, Minn.) and GM-CSF (800 U/mL; Amgen, Thousand Oaks, Calif.) were added to the monocytes to promote their differentiation into dendritic cells. MART-$1_{26-35}$-specific CTL clones were generated as described by Li et al., 2005. J Immunol 175:2261-69, hereby incorporated by reference in its entirety. PBMC used in this study were obtained from HLA-$A2^+$ melanoma patients.

Example 3

Saturation Mutagenesis APL Screen

Following the isolation of the recombinant mini-gene APL products on Talon beads, the bead-bound products were "fed" to 100,000 immature dendritic cells. Following a 4-hour incubation at 37° C., 100,000 MART-$1_{26-35}$-specific CTL clones were added to DC/bead preparations. Following a 12-hour incubation at 37° C., the supernatant was harvested and assayed for the concentration of IFN-γ induced by the APL clones. Anti-IFN-γ antibodies (Endogen) used in the sandwich ELISA were used at 1 µg/ml in PBS/0.1% BSA.

Variant MART-$1_{26-35}$ agonist peptides identified using mutagenesis APL screening and their corresponding DNA sequences are shown in Table 8.

TABLE 8

| Designation | Amino Acid Sequence | SEQ ID NO | DNA Sequence | SEQ ID NO |
|---|---|---|---|---|
| MART-$1_{26-35}$ | EAAGIGILTV | 228 | NA | |
| A27L | ELAGIGILTV | 362 | NA | |
| E26G | GLAGIGILTV | 363 | ggactcgccggaatcggcattctgacc | 377 |
| E26S | SLAGIGILTV | 364 | tcactcgccggaatcggcattctgacc | 378 |
| E26S | SLAGIGILTV | 364 | tcgctcgccggaatcggcattctgacc | 379 |
| E26S | SLAGIGILTV | 364 | agtctcgccggaatcggcattctgacc | 380 |
| L33M | ELAGIGIMTV | 365 | gagctcgccggaatcggcatgctgacc | 381 |

Example 4

In Vitro PBMC Stimulations with Analog Peptides and Tetramer Staining

On day 0, monocyte-derived dendritic cells were pulsed with 1 µM of each MART-$1_{26-35}$ analog peptide for 2 hours at 37° C. The DCs were washed and added to 500,000 HLA-$A2^+$ PBMC from melanoma patients at a 1:20 ratio in 24-well plates. On day 2, 12.5 U/ml of IL-2, 5 ng/ml IL-7, 1 ng/ml IL-15, and 10 ng/ml of IL-21 were added to each culture. Cytokines were replenished every 2-3 days for 1-week. Following the 1-week primary stimulation, cultures were re-stimulated with 1×10⁶ irradiated monocytes pulsed with 10 µM of the peptide used in the primary stimulation. IL-2, IL-7 and IL-15 were added to secondary stimulations on day 2. Cytokines were replenished every 2-3 days. 500,000 cells from each culture were stained with APC-labeled anti-CD8 antibody (Caltag Lab, Burlingame, Calif.) and PE-labeled MART-$1_{76-35}$ HLA-A2.1 tetramers. Stained cells were analyzed using FACScalibur flow cytometer and CellQuest (BD PharMingen) and analyzed using FlowJo software v8.5 (Tree Star, San Carlos, Calif.). Cells were stained with tetramers in 25 µl of 2% FCS/BSA for 1 hour at room temperature, followed by anti-CD8 antibody for 15 minutes at 4° C.

Example 5

Generation of MART-1$_{26-35}$ Polyclonal Cell Lines

Following in vitro peptide stimulation of HLA-A2$^+$ PBMC from melanoma patients MelPt-B, MelPt-C, MelPt-D, MelPt-F and a healthy donor (Healthy-1) MART-1$_{26-35}$ tetramer and CD8 positive cells were sorted and isolated on BD FACSaria. Isolated cells were replicated using 30 ng/ml anti-CD3 antibody (OKT3) and IL-2 at 50 U/ml in the presence of irradiated feeder PBMC and LCL for 2 weeks. IL-2 was replenished every 2-3 days. Following the stimulation, cultures were stained for the generation of MART-1$_{26-35}$ tetramer and CD8 positive cell populations. The polyclonal cell lines were tested for lytic activity and TCR Vβ usage (MelPt-C only), as described in Example 6.

Example 6

In Vitro Cytotoxicity Assay

Target cells were labeled with 100 μCi of $^{51}$Cr and co-cultured with effector cells for 4 hours at 37° C. plus 5% CO$_2$. Targets were melanoma cell lines A375 (HLA-A2$^+$/NY-ESO-1$^+$) and Mel 526 (HLA-A2$^+$/MART-1$^+$), and T2 cells pulsed with 1 μM of MART-1$_{26-35}$ (positive control) or NY-ESO-1$_{157-165}$ (negative control). Effector cells were MART-1$_{26-35}$-tetramer positive polyclonal cell lines generated with either A27L, E26S, or L33M peptides (SEQ ID NOS:362, 364, and 365, respectively). Assays were performed in triplicate at a 50:1, 25:1 or 12.5:1 effector to target ratio. Released $^{51}$Cr was measured with a gamma scintillation counter and percent specific lysis was determined by using the formula: percent specific release=(experimental release-spontaneous release)/(maximum release-spontaneous release).

Example 7

TCR Spectratype Analysis

TCR Vβ spectratype analysis was carried out by the Immune Monitoring Laboratory at Fred Hutchinson Cancer Research Center. Briefly, cDNA was generated from 1×10$^6$ MART-1$_{26-35}$ tetramer staining polyclonal cell lines. Multiplex Vβ PCR primers were then used to amplify the variable regions of the complementarity-determining region 3 (CDR3) of the TCR β chain. Sequence analysis to determine the Vβ usage of the TCRs was conducted with GenScan.

Example 8

Mart-1$_{26-35}$ Specific CTL Clones can Detect Enhanced CTL Epitopes as Reflected by IFN-γ Expression To identify superagonist APLs, a novel genetic system was discovered and developed. This system employs saturation mutagenesis of agonist peptide-encoding oligonucleotides, which when expressed in *E. coli* will contain position specific single amino acid substitutions. The positional libraries are designed such that the codon of interest is totally randomized (NNN), resulting in a pool of oligonucleotides which contains every given codon sequence. This mutagenesis approach might be likened to a slot machine which contains three positions (a codon) and each position has the same 4 possibilities (A, C, G or T). When pulled, there is a 1 in 64 chance of getting any combination of 3. If pulled 100 times there is a high probability that every sequence will be represented (80% certainty, according to a Poisson distribution). Here, the 100 pulls represent 100 bacterial colonies, each containing a different mutant agonist peptide-encoding oligonucleotide. When cloned and expressed, each amino acid should be represented in a library of 100, with 80% certainty, according to a Poisson distribution. A positional library can be generated for each position (amino acid) of the target peptide. The APL min-gene constructs are fused to a 6×-histidine tag (SEQ ID NO: 415), and can easily be separated from bacterial proteins on Co$^{2+}$-coated paramagnetic beads. APLs are screened for the ability to activate epitope-specific CTL clones following cross-presentation of the bead-bound ligand on class I MHC molecules by immature dendritic cells (DC).

To validate this system and to verify that it was sensitive enough to detect our model tumor-associated HLA-A2 restricted antigenic peptide, MART-1$_{26-35}$, as well as an APL superagonist epitope of MART-1$_{26-35}$, called MART-1$_{26-35}$A27L (henceforward referred to as A27L (SEQ ID NO:362)), oligonucleotides encoding the appropriate peptide sequences were cloned, expressed and assayed for the ability to activate antigen specific CTL clones as described in materials and methods. The CTL clone used in this assay, called M26-H1, is specific for MART-1$_{26-35}$, and expresses IFN-γ in response to HLA-A2/MART-1$_{26-35}$ complexes. Here, the IFN-γ response elicited by the recombinant unmodified MART-1$_{26-35}$ cross-presented construct is significantly higher than that elicited by the HLA-A2 restricted negative control, NYESO-1$_{157-165}$ (FIG. 1). Further, the IFN-γ response elicited by the recombinant superagonist APL, A27L, was more than 2-fold higher than that elicited by the recombinant wild type construct. Yet, the activation of M26-H1 by the unmodified MART-1$_{26-35}$ construct was clearly distinguishable from that elicited by the HLA-A2 restricted negative control construct, NYESO1$_{157-165}$. These results suggest that the HLA-A2 cross-presented recombinant ligands are sufficient to elicit detectable antigen-specific responses from CTL clones, and also that superagonist APLs can be distinguished based on an increase in IFN-γ expression, relative to the wild type CTL ligand.

Example 9

Figure 2:
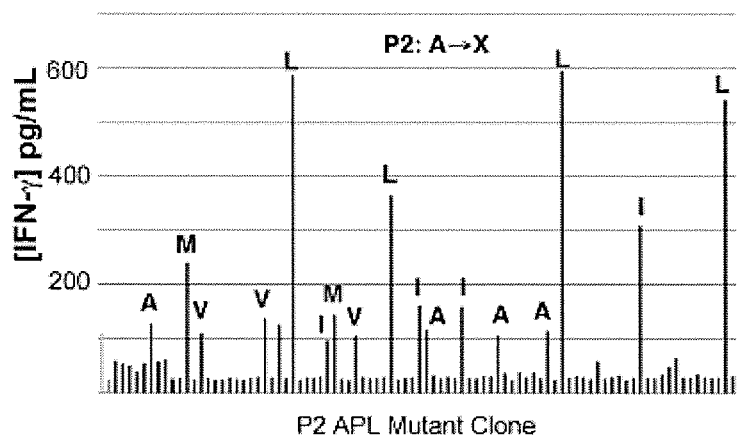
FIG. 2. Previously described superagonists identified in MART-1$_{26-35}$ Position 2 saturation mutagenesis APL screen. 88 P2 saturation mutagenesis clones were screened. MART-1$_{26-35}$ control construct is the first bar on left, and the NY-ESO-1$_{157-165}$ negative control construct is the second bar from left. APL clones eliciting comparable IFN-γ expression as the native construct were sequenced. The amino acid at position 27 is shown above for the most active polypeptide sequences.

Saturation Mutagenesis can Effectively Generate Random Amino Acids in the Parental Antigenic Peptide from which Enhanced Agonist APLS can be Identified The saturation mutagenesis APL library screen depends on 200 μl bacterial expression cultures in 96-well plates. FIG. 1 shows that cross-presented recombinant ligands can be detected by antigen-specific CTL. However, in that experiment recombinant proteins were produced at high concentrations in 5 ml cultures. To determine whether the recombinant protein produced in these significantly smaller cultures would be sufficient to reflect detectable and varying degrees of activation, a position 2 (P2) library of MART-1$_{26-35}$ (E XAGIGILTV (SEQ ID NO: 416)) was constructed. By screening this library, in addition to determining if 200 μl cultures produce sufficient concentrations of recombinant protein previously identified superagonist APLs, including A27L could be identified from among 88 unique mutant APL clones. The P2 library screen (FIG. 2), using the CTL clone M26-H1, clearly shows that the wild type recombinant ligand MART-1$_{26-35}$ elicits significantly more IFN-γ than the negative control. Furthermore, the APL clones from the library that contained leucine residues at P2 (A27L), elicited significantly more IFN-γ expression in comparison to the wild type ligand. Amino acid content was determined from replicated glycerol stock of the P2 bacterial library. Interestingly, APL clones containing methionine residues at P2 also elicited greater IFN-γ expression than wild type MART-$1_{26-35}$, although not as great as that elicited by the leucine containing APLs, A27L. Like A27L, A27M is a superagonist APL of MART-$1_{26-35}$. Thus, 200 μl bacterial cultures produce sufficient concentrations of the recombinant ligands to be detected in this screen. Also, superagonist APLs can be identified in a library of at least 88 unique APL clones.

Example 10

Putative Enhanced CTL Epitopes of Mart-$1_{26-35}$A27L are Identified in APL Library Screens On the basis of previous results demonstrating that superagonist APLs can be identified and defined using the saturation mutagenesis screen, remaining positional libraries of MART-$1_{26-35}$, were screened using similar methods. Because a potent superagonist APL of MART-$1_{26-35}$ has already been identified in A27L, A27L was used as the basis for a mutational strategy. That is, leucine in position 2 was constant, while other positions were mutated independently. This would allow superagonist APLs to be identified that are more effective than A27L.

Figure 3:
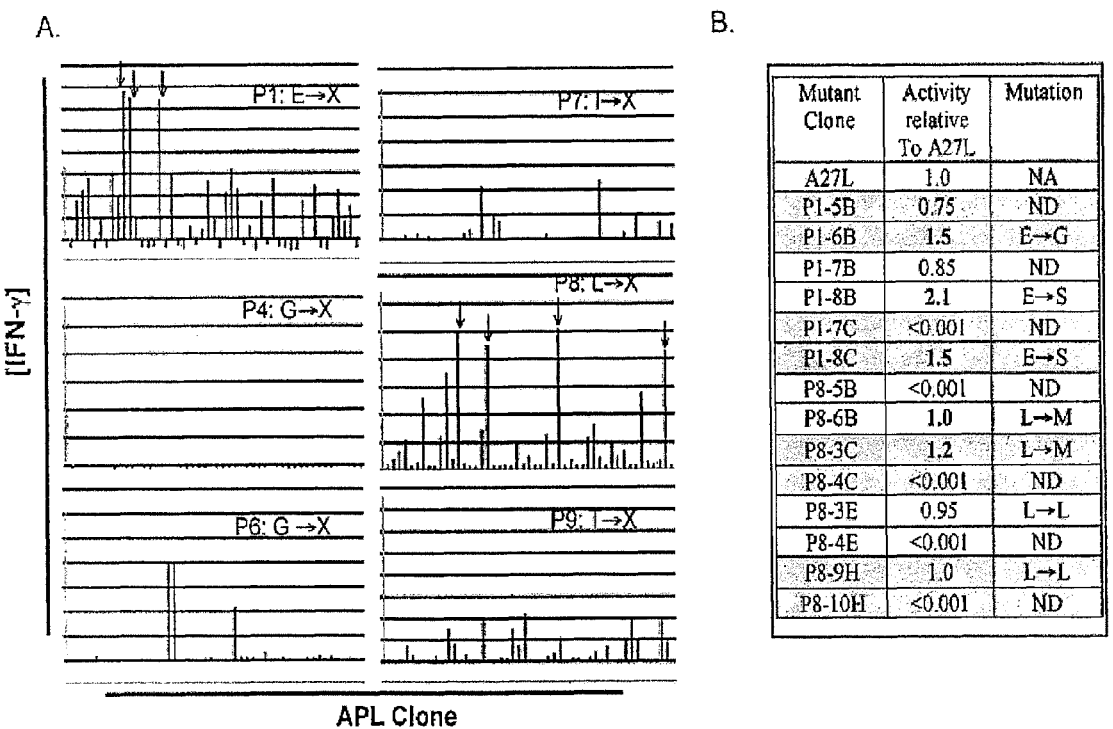
FIG. 3. Eight positional libraries of A27L were screened using the saturation mutagenesis technique. 88 mutant clones were screened for each of eight positional libraries of A27L-P1, P3, P4, P5, P6, P7, P8 and P9. (Fin. 3A) 2 clones are screened simultaneously for each library. Activation was assessed by IFN-γ expression. Positive control (A27L; SEQ ID NO:362) is the far left bar while the negative control (NYESO-1$_{157-165}$) is the second from left. APL clonal wells indicated with an arrow were de-convoluted and each mutant APL re-screened separately.

The APL libraries were screened with two different high avidity MART-$1_{26-35}$-specific CTL clones. A high avidity TCR is defined as having the ability to recognize tumor cells that express both MART-1 and HLA-A2 class I molecules. The vast majority of the MART-$1_{26-35}$ derivative mutant peptide clones screened from each of the positional libraries were not as effective as A27L at activating the MART-$1_{26-35}$-specific CTL clone (FIG. 3). However, several clones from the P1, P3 and P8 libraries appeared to work similarly as well as the A27L recombinant construct. The initial screen was conducted by screening two unique APL library clones simultaneously in a single well. While this approach allows twice as many APL clones to be screened, the potency of any agonist APL in the pool is potentially underestimated in the initial screen.

Agonist candidates were selected and re-screened based on their ability to elicit more or comparable levels of IFN-γ from M26-H1 in the initial screen (FIG. 3B). When tested independently, both of the clones from the P3 libraries elicited less IFN-γ expression from the MART-$1_{26-35}$-specific CTL clone, relative to A27L. When re-screened independently, it was apparent that only one of the two mutant peptide clones from the P1 and P8 wells was responsible for the increased IFN-γ expression. The DNA encoding these putative MART-$1_{26-35}$ agonist peptides was prepared from the duplicated bacterial glycerol stocks. The enhancing mutations for the P1 putative agonists contained either glycine (E26G) (SEQ ID NO:363) or serine (E26S) (SEQ ID NO:364) residues at P1 instead of the naturally occurring glutamate residue. The P8 putative agonist contained a methionine residue (L33M) (SEQ ID NO:365) at position 8 rather than the naturally occurring leucine residue. No additional putative agonists were identified from the library screens using the second CTL clone, M26-H2.

Example 11

Figure 4:
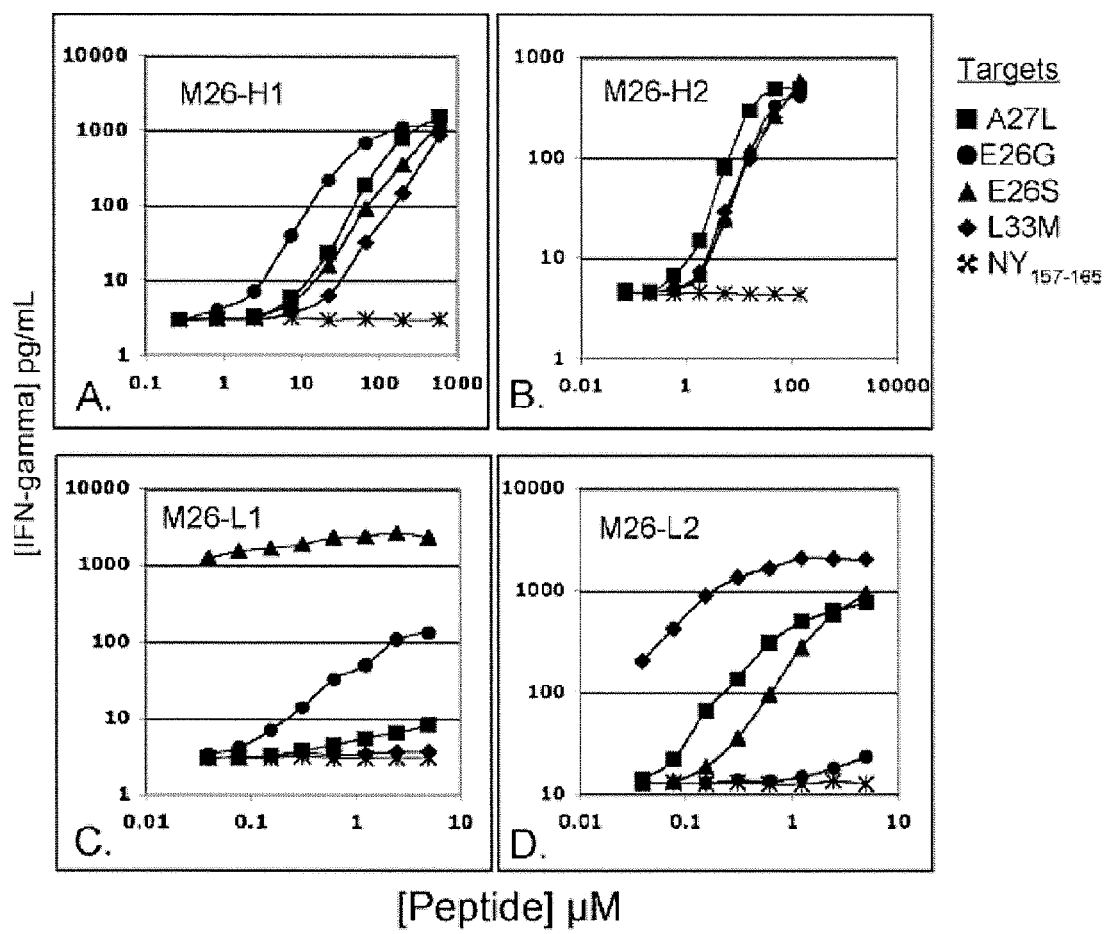
FIG. 4. APLs identified in saturation mutagenesis screen activate unique MART-1$_{26-35}$-specific CTL clones differently. Two unique high avidity MART-1$_{26-35}$-specific CTL clones, M26-H1 (A) and M26-H2 (B), and two unique low avidity MART-1$_{26-35}$-specific CTL clones, M26-L1(C) and M26-L2 (D), were assayed against the agonist peptides A27L (square), E26G (SEQ ID NO:363; circle), E26S (SEQ ID NO:364; triangle), L33M (SEQ ID NO:365; diamond) and NY-ESO-1$_{157-165}$ (x's). Peptides were titrated on T2 target cell. IFN-γ expression was measured by standard ELISA.

MART-$1_{26-35}$ Agonist Peptides Display a Differential Capacity to Activate Different MART-$1_{26-35}$-specific CTL Clones To analyze the putative superagonist APLs on a molar basis, individual peptides were synthesized at greater than 90% purity. To determine whether these APLs would be similarly recognized by unique MART-$1_{26-35}$-specific CTL clones, the APLs were tested against four clones bearing unique T cell receptors (TCR). These included two high avidity CTL clones (M26-H1 and M26-H2) and two low avidity CTL clones (M26-L1 and M26-L2) (FIG. 4). Low-avidity TCR is here defined as having the ability to respond HLA-A2 positive peptide-pulsed target cells but not to cells displaying naturally processed and presented determinants from HLA-A2/MART-1 positive tumors. Low-avidity T cells have the potential to mediate antigen-specific cell and tissue destruction.

FIG. 4 panel A shows that each of the newly identified agonist peptides is similarly effective in activating M26-H1—the high-avidity CTL clone used in the initial screen (as described in FIG. 3) as compared to MART-$1_{26-35}$ superagonist peptide, A27L. A similar pattern of activation was found when the identified agonist peptides are used to stimulate the CTL clone M26-H2. In contrast to the above results, the low-avidity MART-$1_{26-35}$-specific CTL clones yielded widely divergent results in response to different agonist peptides. For example, while the CTL clone M26-L1 recognizes the peptide E26S more than 100-fold better than A27L (based on half-maximal activation), the CTL clone M26-L2 recognizes A27L better than it does E26S. Similarly, while L33M is scarcely recognized by the CTL clone M26-L1, it is the most effective agonist for activating M26-L2. Thus, these analogs might be considered "conditional" agonists, as they do not elicit generalized patterns of activation among unique antigen-specific clonotypes.

Example 12

MART-$1_{26-35}$ APLs Demonstrate Patient-Specific Enhanced Generation of MART-$1_{26-35}$ CTL Populations from the PBMC of Melanoma Patient Donors To determine how well the identified agonist APLs could prospectively generate MART-$1_{26-35}$-specific CTL populations from melanoma patient peripheral blood mononuclear cell (PBMC) preparations, the APLs were used to stimulate eight different patient PBMC samples under standard in vitro conditions (Table 9).

TABLE 9

| Patient | A27L | E26G | E26S | L33M |
|---------|------|------|------|------|
| MelPt-A | 3.14 (1) | 1.68 (0.53) | 3.36 (1.07) | 0.98 (0.31) |
| MelPt-B | 2.97 (1) | 1.31 (0.44) | 4.3 (1.45) | 7.7 (2.6) |
| MelPt-C | 40.6 (1) | 45.6 (1.12) | 15.6 (0.38) | 41.1 (1.02) |
| MelPt-D | 0.65 (1) | 1.73 (2.66) | 3.43 (5.27) | 2.07 (3.1) |
| MelPt-E | 1.77 (1) | 8.42 (4.75) | 6.88 (3.88) | 24.2 (13.67) |
| MelPt-F | 5.45 (1) | 3.35 (0.61) | 3.72 (0.68) | 3.07 (0.56) |
| MelPt-G | 33.4 (1) | 1.89 (.06) | 1.75 (.05) | 2.37 (.07) |
| MelPt-H | 1.24 (1) | 2.03 (1.63) | 1.31 (1.06) | 2.77 (2.2) |

These results show that MART-$1_{26-35}$ APLs exhibit differential capacities to generate MART-$1_{26-35}$-specific CTL populations from the PBMC of different melanoma patient donors. APLs were used to stimulate PBMC cultures in vitro. Following a one-week secondary stimulation cells were stained with FITC-labeled anti-CD8 antibodies and APC-labeled HLA-A2/MART-$1_{26-35}$ tetramers and analyzed by flow cytometry. Values are given as percent tetramer positive relative to a negative control. The fold difference relative to A27L is indicated in parentheses. Differences of more than two-fold are indicated in bold.

Figure 5:
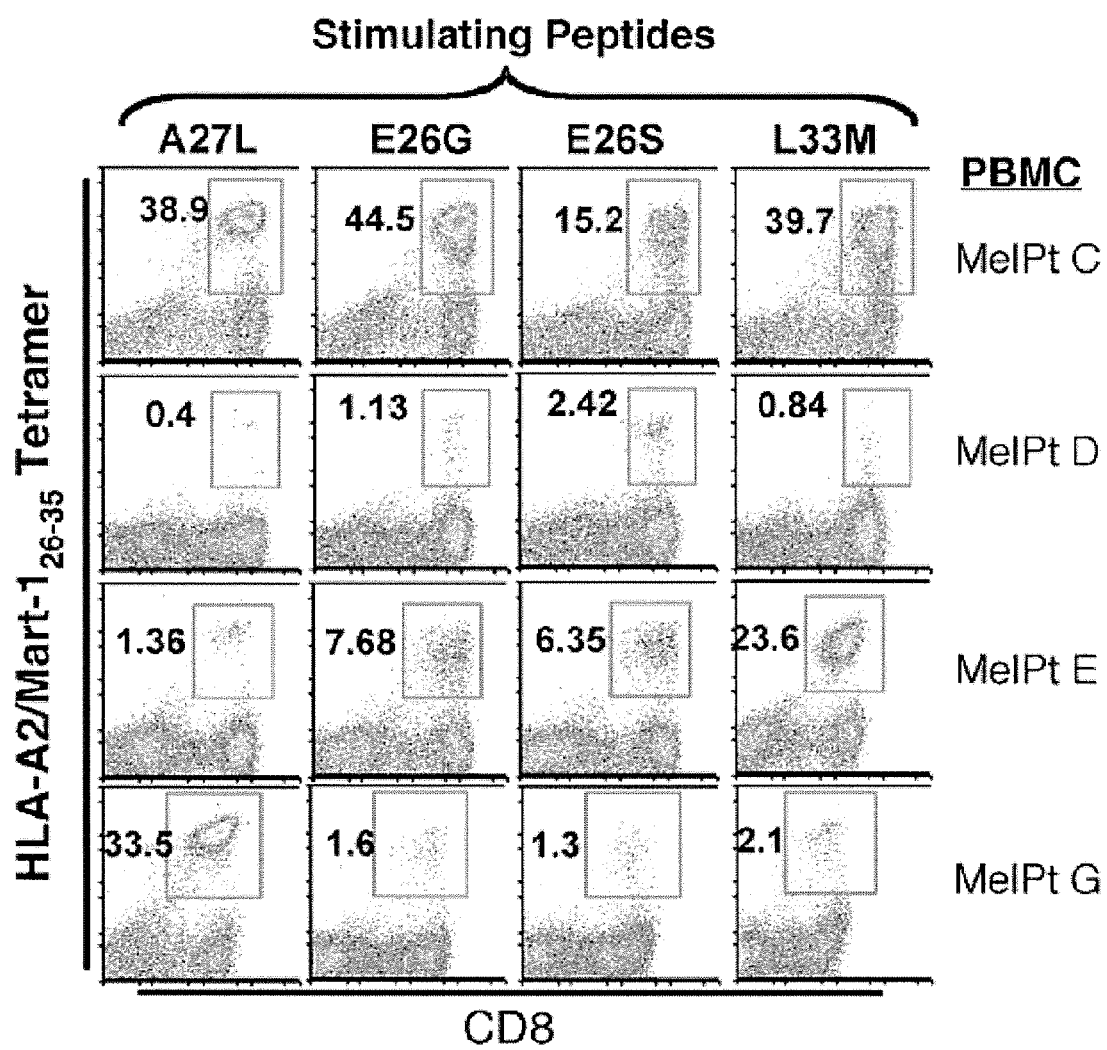
FIG. 5. APLs generate different CTL responses from the PBMC of different melanoma patients. Identified APLs were used to stimulate peripheral blood mononuclear cells (PBMC) of different melanoma patients in vitro. Following a one week primary and one week secondary peptide stimulation, cultures were stained with FITC-labeled anti-CD8 antibody and APC-labeled HLA-A2/MART-1$_{26-35}$ tetramer and analyzed by flow cytometry. Data is representative of at least three different experiments.

One week following the second in vitro stimulation, cultures were stained with the wild-type MART-1$_{26-35}$/HLA-A2 tetramer. Similar to the observations made using different MART-1$_{26-35}$-specific CTL clones, none of the peptide ligands were universally effective in generating MART-1$_{26-35}$-specific CTL populations from all patient PBMC samples (FIG. 5). Any given APL was more or less effective in generating antigen-specific CTL from any given patient PBMC sample. For example, while the agonist peptide E26S is the least effective at generating MART-1$_{26-35}$-specific CD8 positive populations from the PBMC of MelPt-C (3-fold<A27L), it is the most effective APL for generating such T cell populations from MelPt-D (5-fold>A27L) Similarly, whereas the agonist peptide L33M is 14-fold more effective than A27L in generating of MART-1$_{26-35}$-specific CD8 positive populations from the PBMC of MelPt-E, it is 14-fold less effective than A27L in generating MART-1$_{26-35}$-specific CD8 populations from the PBMC of MelPt-G. These findings demonstrate that any one CTL ligand may not be effective at generating antigen-specific CTL populations from the PBMC of any given patient; and show the importance of establishing a panel of potential superagonist APLs.

Example 13

CD8 Positive MART-1$_{26-35}$-Specific Polyclonal Cell Lines Generated with the Identified MART-1$_{26-35}$ Agonist APLS can Kill HLA-A2$^+$ Tumors Expressing Endogenous MART-1

The use of altered peptide ligands poses the risk of generating antigen-specific T cells which display relatively low anti-tumor functional avidity. To determine whether the MART-1$_{26-35}$-specific CTL that were generated with these novel MART-1$_{26-35}$ agonist peptides were of sufficient functional avidity to kill HLA-A2/MART-1 positive tumor targets, polyclonal lines of CD8 positive MART-1$_{26-35}$ tetramer-staining cells were established from the PBMC of MelPt-B, MelPt-C, MelPt-D, MelPt-F or a healthy donor (Healthy1), stimulated with either A27L, E26S or L33M agonist peptides (SEQ ID NOS:362, 364, and 365, respectively). These cell lines were screened for reactivity to unmodified MART-1$_{26-35}$ peptide pulsed HLA-A2 positive targets and to HLA-A2/MART-1 positive tumor targets at varying effector to target ratios in a standard chromium release assay (Table 10).

TABLE 10

Tumor specific lysis by CTL generated with MART$_{126-35}$ peptide analogs

Percentage Specific Lysis from polyclonal CTL lines generated with the indicated peptide

| | | MART-1$_{26-35}$A27L | | | | MART-1$_{26-35}$E26S | | | | MART-1$_{26-35}$L33M | | | |
|---|---|---|---|---|---|---|---|---|---|---|---|---|---|
| Patient | E/T | T2 | T2 + M26 | A375 | Mel526 | T2 | T2 + M26 | A375 | Mel526 | T2 | T2 + M26 | A375 | Mel526 |
| MelPt-B | 50 | ND | ND | ND | ND | 0$^c$ | 40 | 6 | 58 | 2 | 63 | 13 | 80 |
| | 25 | ND | ND | ND | ND | 0 | 31 | 4 | 45 | 2 | 52 | 12 | 70 |
| | 12.5 | ND | ND | ND | ND | 2 | 21 | 8 | 30 | 4 | 41 | 9 | 58 |
| MelPt-C | 50 | 9 | 73 | 3 | 35 | 2 | 87 | 8 | 41 | 9 | 91 | 0 | 58 |
| | 25 | 10 | 52 | 5 | 30 | 7 | 66 | 5 | 32 | 12 | 84 | 2 | 52 |
| | 12.5 | 9 | 42 | 2 | 25 | 1 | 54 | 2 | 25 | 11 | 76 | 5 | 45 |
| MelPt-D | 50 | 0 | 50 | 10 | 32 | 3 | 87 | 8 | 41 | 14 | 90 | 2 | 57 |
| | 25 | 2 | 42 | 10 | 30 | 8 | 65 | 7 | 32 | 11 | 84 | 4 | 54 |
| | 12.5 | 5 | 35 | 9 | 25 | 1 | 54 | 6 | 25 | 8 | 75 | 6 | 45 |
| MelPt-F | 50 | 6 | 92 | 5 | 65 | ND | ND | ND | ND | 23 | 70 | 2 | 44 |
| | 25 | 3 | 81 | 5 | 50 | ND | ND | ND | ND | 21 | 72 | 3 | 42 |
| | 12.5 | 2 | 73 | 5 | 43 | ND | ND | ND | ND | 22 | 65 | 5 | 38 |
| Healthy1 | 50 | 2 | 52 | 3 | 58 | 0 | 34 | 9 | 28 | 2 | 57 | 13 | 65 |
| | 25 | 4 | 42 | 7 | 42 | 0 | 26 | 5 | 15 | 6 | 49 | 13 | 57 |
| | 12.5 | 1 | 31 | 6 | 35 | 0 | 18 | 8 | 10 | 5 | 38 | 10 | 44 |

"ND" is not done. T2 is a TAP-deficient cell line that expresses peptide-unbound HLA-A2 molecules unless pulsed extracellularly. Here, T2 was pulsed with NY-ESO-1$_{157-165}$ unless indicated otherwise. M26 is an abbreviation for the unmodified MART-1$_{26-35}$ peptide. Numbers represent the percentage specific lysis obtained from each target. T375 is a HLA-A2 positive/MART-1 negative cell line.

The results illustrate that the CTL populations that were generated from each PBMC source with either of the altered peptide ligands can kill targets that display wild-type MART-1$_{25-35}$ in the context of HLA-A2, and recognize the epitope with sufficient affinity to kill tumors expressing MART-1.

To determine whether unique or shared MART-1$_{25-35}$-specific CTL clonotypes were generated with each of the peptide ligands (A27L, E26S and L33M), spectratype analysis was performed on CTL lines derived from MelPt-C PBMC to determine their Vβ TCR usage. Results showed that the agonist peptides A27L, E26S and L33M generated CTL populations that primarily (>90%) utilized TCR Vβ24, Vβ8 and Vβ3, respectively. This suggests that the different analog peptides preferentially generate specific TCR utilizing CTL subsets. Taken together, these results demonstrate the ability of the identified APLs to elicit MART-1$_{26-35}$-specific CTL responses that are capable of directly killing MART-1 expressing tumors, and suggest that unique MART-1$_{25-35}$-specific TCR subpopulations are being preferentially generated by the different MART-1$_{26-35}$ analog peptides.

Example 14

NY-ESO APLs

Figure 6:
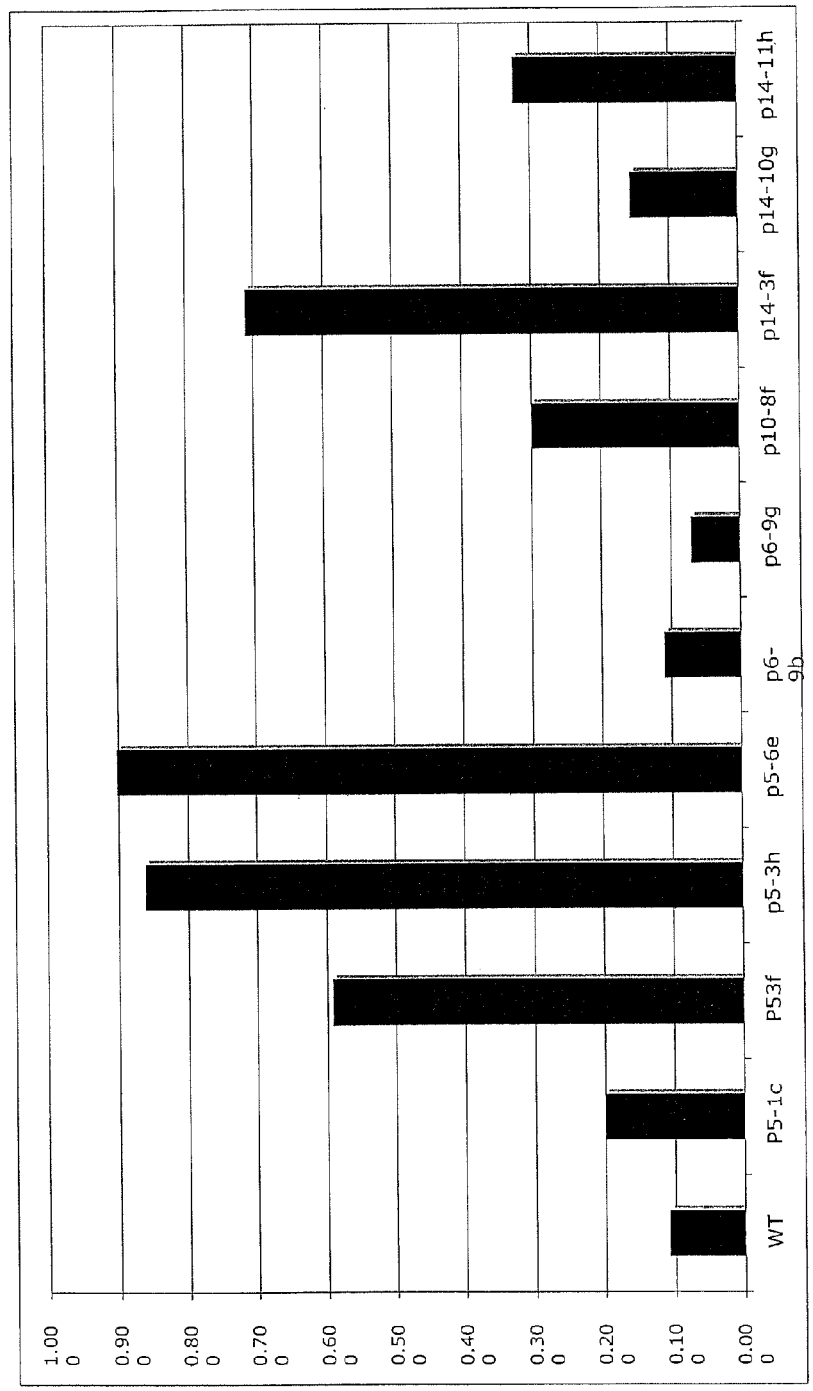
FIG. 6. Native and superagonist CTL determinants can be distinguished in bead-based cross-presentation assay. Oligonucleotides encoding NY-ESO-1$_{157-170}$ were cloned into and expressed by pQE40 expression vectors. The mini-gene products were isolated and "fed" to immature dendritic cells as described in Examples 2-8. NY-ESO-1$_{157-170}$-specific CTL clones were used to detect the presence of the cross-presented mini-gene products. Induced IFN-γ expression was determined by standard sandwich ELISA. Synthetic wild-type peptide was used a positive control.

The methods of Examples 2-8 were used to generate enhanced agonist APLs. Results of a library screen are shown in FIG. 6. Clones showing activity were sequenced. Variant sequences with the most activity correspond to amino acid sequences of SEQ ID NOS:368-376.

Using the methods of Example 11 to analyze the putative superagonist APLs on a molar basis, individual peptides were synthesized at greater than 90% purity. To determine whether these APLs would be similarly recognized by unique NY-ESO-1-specific CTL clones, the APLs were tested against ten clones bearing unique TCR. Each of the newly identified agonist peptides is similarly effective in activating CTL clones used in the initial screen in comparison to wild-type NY-ESO-1$_{157\text{-}170}$ superagonist peptide. Different patterns of stimulation are obtained with different CTL clones. Specific CTL clones yielded widely divergent results in response to different agonist peptides. Similar to results obtained with MART superagonist peptides, these NY-ESO-1 analogs might be considered "conditional" agonists, as they do not elicit generalized patterns of activation among unique antigen-specific clonotypes.

Figure 7:
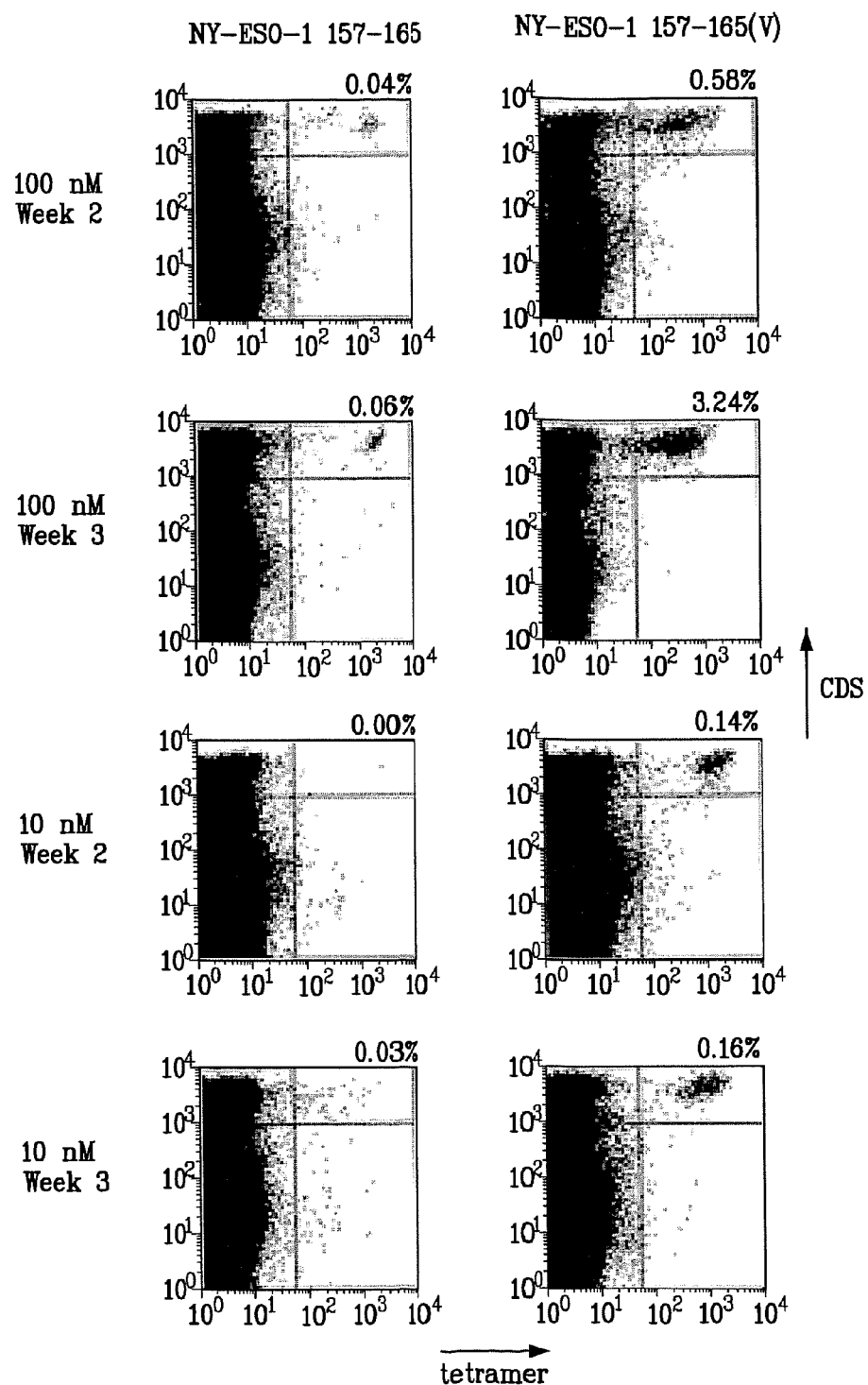
FIG. 7. NYESO-1$_{157-165}$ C165V generates Specific CTL better than the wild type peptide. Following a 1-week primary and 1-week secondary peptide stimulation (Week 2), and an additional week (Week 3), cultures were stained with FITC-labeled anti-CD8 antibody and APC-labeled HLA-A2/NY-ESO and analyzed by flow cytometry. Two peptides were tested, NY-ESO-I$_{157-165}$ (SEQ ID NO:366) wild-type, and NY-ESO-1$_{157-170}$-(V) (SEQ ID NO:376).

The NY-ESO-1$_{157\text{-}165}$ C165V APL SEQ ID NO:376 was compared to wild-type NY-ESO-1$_{157\text{-}165}$ SEQ ID NO:366 in effectively producing CTL from PBMC. FIG. 7 shows that the variant peptide had a higher avidity than the wild type sequence to a CD-8$^+$ population.

Figure 8A:
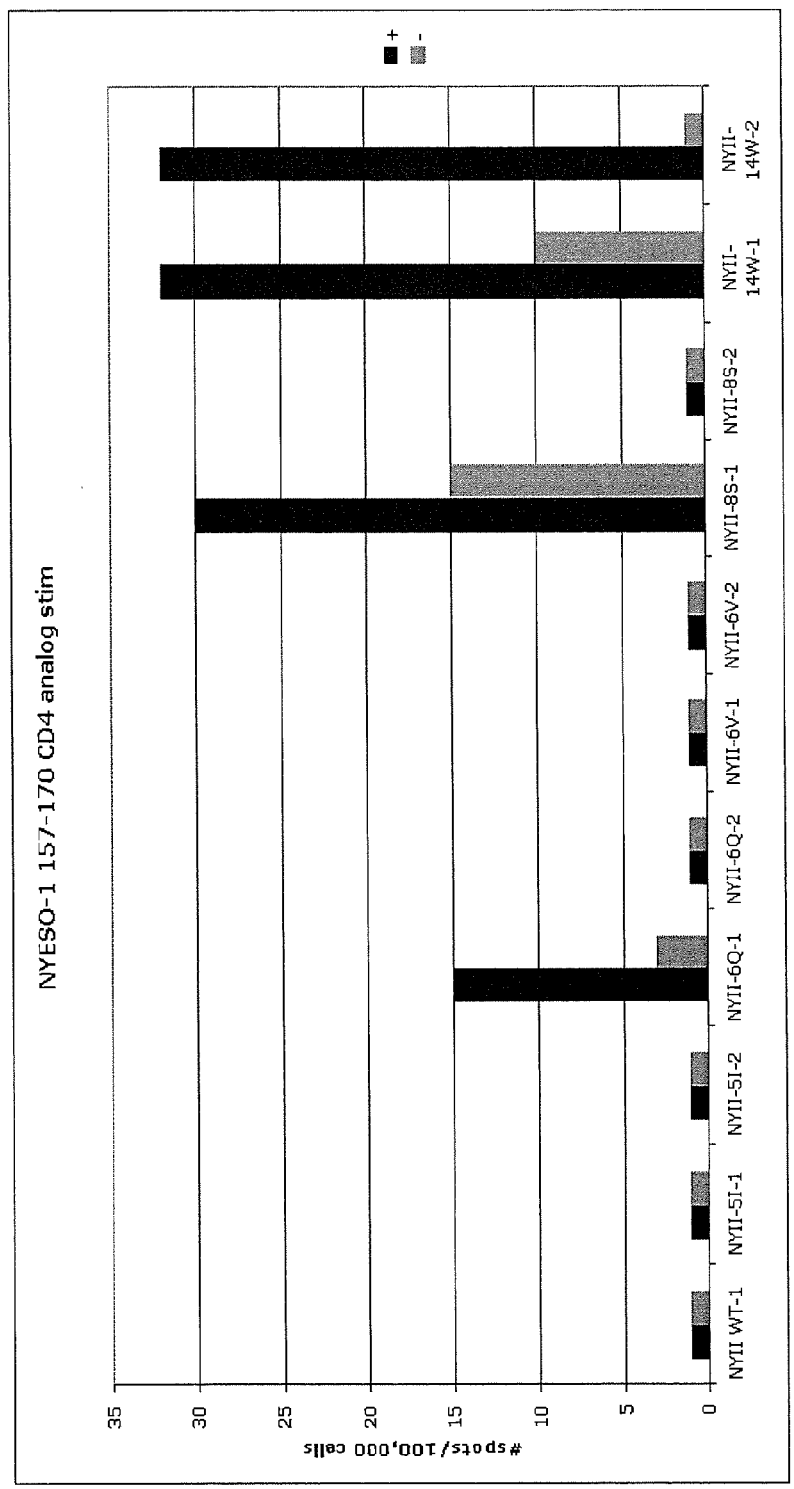
FIG. 8. Native and superagonist CTL determinants can be distinguished in bead-based cross-presentation assay. Oligonucleotides encoding NY-ESO-1$_{157-170}$ were cloned into and expressed by pQE40 expression vectors. The mini-gene products were isolated and "fed" to immature dendritic cells as described in the Examples. NY-ESO-1$_{157-170}$-specific CTL clones were used to detect the presence of the cross-presented mini-gene products (NY-ESO-1$_{157-170}$). PBMC (FIG. 8B) were compared to CD-4$^+$ cells (FIG. 8A). Induced IFN-γ expression was determined by standard sandwich ELISA. Synthetic wild-type peptide was used a positive control. The designations for the clones are as follows: NYII WT-1 is SEQ ID NO:362; NYII-5I-1 and -2 are W161I (SEQ ID NO:368); NYII-6Q-1 and -2 are I162Q (SEQ ID NO:372); NYII-6V-1 and -2 are I162V (SEQ ID NO:373); NYII-8S-1 and -2 are Q164S (SEQ ID NO: 374); NYII14W-1 and -2 are F170W (SEQ ID NO:375).
Figure 8B:
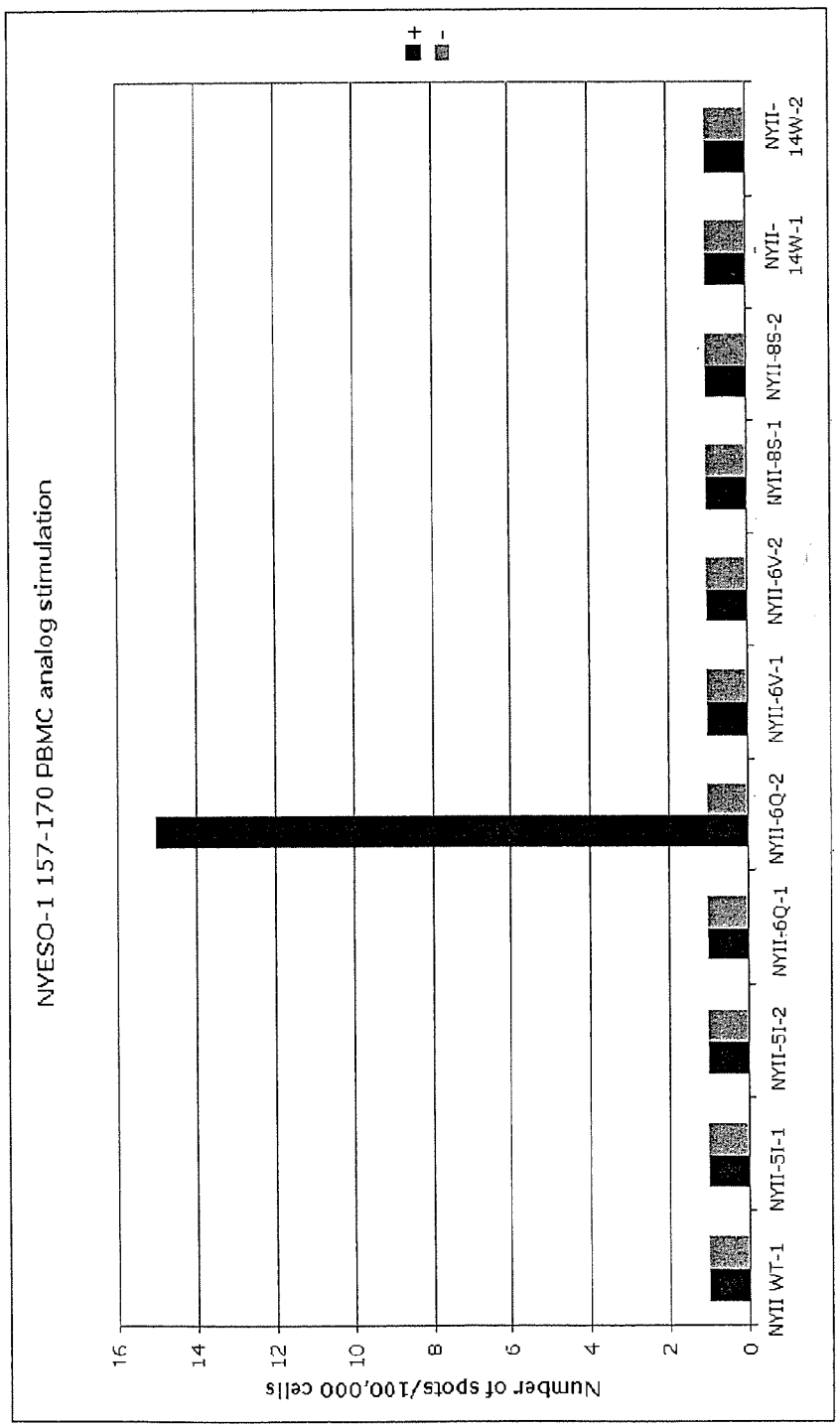

FIG. 8 show the ability of several NY-ESO-1APL to stimulate CD-4$^+$ fractions (FIG. 8A) and PBMC (FIG. 8B) and. Results showed that NY-ESO 1APLs I162Q, Q164S, and F170W (SEQ ID NOS:372, 374, and 375, respectively) were the most effective in stimulating CD-4$^+$ cells.

NY-ESO-1$_{157\text{-}170}$ agonist peptides identified using mutagenesis APL screen and their corresponding DNA sequences are shown in the following Table 11.

TABLE 11

| Designation | Amino Acid Sequence | SEQ ID NO | DNA Sequence | SEQ ID NO |
|---|---|---|---|---|
| NY-ESO-1$_{157\text{-}170}$ | SLLMWITQCFLPVF | 144 | NA | |
| W161I | SLLMIITQCFLPVF | 368 | agcctgctgatgatcattacccagtgctttctgccggtgttttaa | 382 |
| W161I | SLLMIITQCFLPVF | 368 | agcctgctgatgattattacccagtgctttctgccggtgttttaa | 383 |
| Q164S | SLLMWITSCFLPVF | 374 | agcctgctgatgtggattacctcatgctttctgccggtgttttaa | 384 |
| F170W | SLLMWITQCFLPVW | 375 | agcctgctgatgtggattacccagtgctttctgccggtgttttgg | 385 |
| W161F | SLLMFITQCFLPVF | 369 | agcctgctgatgtttattacccagtgctttctgccggtgttttaa | 386 |
| I162R | SLLMWRTQCFLPVF | 370 | agcctgctgatgtggaggacccagtgctttctgccggtgttttaa | 387 |
| I162M | SLLMWMTQCFLPVF | 371 | agcctgctgatgtggatgacccagtgctttctgccggtgttttaa | 388 |
| I162Q | SLLMWQTQCFLPVF | 372 | agcctgctgatgtggcaaacccagtgctttctgccggtgttttaa | 389 |
| I162V | SLLMWVTQCFLPVF | 373 | agcctgctgatgtgggtgacccagtgctttctgccggtgttttaa | 390 |
| Q164S | SLLMWITSCFLPVF | 374 | agcctgctgatgtggattacctctgctttctgccggtgttttaa | 391 |

What is claimed:

1. A compound for the treatment of a patient with a tumor, wherein the compound comprises a peptide comprising a tumor epitope, wherein the tumor epitope comprises an amino acid substitution in a tumor antigen, wherein the tumor antigen is SEQ ID NO: 144 or 228, and wherein the compound comprises a sequence selected from the group consisting of SEQ ID NOS: 362-365 and 368-376.

2. The compound of claim 1, wherein the peptide is produced by an expression vector in a host cell in vitro wherein the expression vector comprises a nucleotide sequence selected from the group consisting of SEQ ID NO: 377-391.

3. The compound of claim 2, where the nucleotide sequence is expressed in human cells.

4. The compound of claim 3, wherein the nucleotide sequence is expressed in cells obtained from a melanoma patient.

5. The compound of claim 1, wherein the tumor antigen is SEQ ID NO: 144, and wherein the compound comprises a sequence selected from the group consisting of SEQ ID NOS: 368-376.

6. The compound of claim 5, wherein the peptide is produced by an expression vector in a host cell in vitro wherein the expression vector comprises a nucleotide sequence selected from the group consisting of SEQ ID NO: 382-391.

7. The compound of claim 5, wherein the compound comprises a sequence consisting of SEQ ID NOS: 372, 374, or 375.

8. The compound of claim 1, wherein the tumor antigen is SEQ ID NO: 228, and the compound comprises a sequence selected from the group consisting of SEQ ID NOS: 362-365.

9. The compound of claim 8, wherein the peptide is produced by an expression vector in a host cell in vitro wherein the expression vector comprises a nucleotide sequence selected from the group consisting of SEQ ID NOS: 377-381.

10. The compound of claim 8, wherein the tumor antigen is SEQ ID NO: 228, and the compound comprises a sequence consisting of SEQ ID NOS: 362, 363 or 365.

11. The compound of claim 1, wherein the wherein the compound comprises a multiplicity of sequences selected from the group consisting of SEQ ID NOS: 362-365 and 368-376.

12. The compound of claim 11, wherein the wherein the compound comprises a multiplicity of sequences selected from the group consisting of SEQ ID NOS: 362-365.

13. The compound of claim 12, wherein the compound comprises a sequence consisting of SEQ ID NOS: 362, 363 or 365.

14. The compound of claim 11, wherein the wherein the compound comprises a multiplicity of sequences selected from the group consisting of SEQ ID NOS: 368-376.

15. The compound of claim 14, wherein the compound comprises a sequence consisting of SEQ ID NOS: 372, 374, or 375.

* * * * *

SEQUENCE LISTING

<160> NUMBER OF SEQ ID NOS: 416

<210> SEQ ID NO 1
<211> LENGTH: 10
<212> TYPE: PRT
<213> ORGANISM: Homo sapiens

<400> SEQUENCE: 1

Phe Ile Ala Ser Asn Gly Val Lys Leu Val
1               5                   10

<210> SEQ ID NO 2
<211> LENGTH: 15
<212> TYPE: PRT
<213> ORGANISM: Homo sapiens

<400> SEQUENCE: 2

Tyr Ser Val Tyr Phe Asn Leu Pro Ala Asp Thr Ile Tyr Thr Asn
1               5                   10                  15

<210> SEQ ID NO 3
<211> LENGTH: 9
<212> TYPE: PRT
<213> ORGANISM: Homo sapiens

<400> SEQUENCE: 3

```
Ser Ser Lys Ala Leu Gln Arg Pro Val
1               5

<210> SEQ ID NO 4
<211> LENGTH: 29
<212> TYPE: PRT
<213> ORGANISM: Homo sapiens

<400> SEQUENCE: 4

Glu Asp Leu Thr Val Lys Ile Gly Asp Phe Gly Leu Ala Thr Glu Lys
1               5                   10                  15

Ser Arg Trp Ser Gly Ser His Gln Phe Glu Gln Leu Ser
            20                  25

<210> SEQ ID NO 5
<211> LENGTH: 9
<212> TYPE: PRT
<213> ORGANISM: Homo sapiens

<400> SEQUENCE: 5

Phe Leu Ile Ile Trp Gln Asn Thr Met
1               5

<210> SEQ ID NO 6
<211> LENGTH: 9
<212> TYPE: PRT
<213> ORGANISM: Homo sapiens

<400> SEQUENCE: 6

Phe Pro Ser Asp Ser Trp Cys Tyr Phe
1               5

<210> SEQ ID NO 7
<211> LENGTH: 9
<212> TYPE: PRT
<213> ORGANISM: Homo sapiens

<400> SEQUENCE: 7

Ser Tyr Leu Asp Ser Gly Ile His Phe
1               5

<210> SEQ ID NO 8
<211> LENGTH: 12
<212> TYPE: PRT
<213> ORGANISM: Homo sapiens

<400> SEQUENCE: 8

Phe Ser Trp Ala Met Asp Leu Asp Pro Lys Gly Ala
1               5                   10

<210> SEQ ID NO 9
<211> LENGTH: 10
<212> TYPE: PRT
<213> ORGANISM: Homo sapiens

<400> SEQUENCE: 9

Ala Cys Asp Pro His Ser Gly His Phe Val
1               5                   10

<210> SEQ ID NO 10
<211> LENGTH: 9
<212> TYPE: PRT
<213> ORGANISM: Homo sapiens
```

```
<400> SEQUENCE: 10

Ala Val Cys Pro Trp Thr Trp Leu Arg
1               5

<210> SEQ ID NO 11
<211> LENGTH: 14
<212> TYPE: PRT
<213> ORGANISM: Homo sapiens

<400> SEQUENCE: 11

Thr Leu Tyr Gln Asp Asp Thr Leu Thr Leu Gln Ala Ala Gly
1               5                   10

<210> SEQ ID NO 12
<211> LENGTH: 16
<212> TYPE: PRT
<213> ORGANISM: Homo sapiens

<400> SEQUENCE: 12

Thr Met Lys Gln Ile Cys Lys Lys Glu Ile Arg Arg Leu His Gln Tyr
1               5                   10                  15

<210> SEQ ID NO 13
<211> LENGTH: 10
<212> TYPE: PRT
<213> ORGANISM: Homo sapiens

<400> SEQUENCE: 13

Lys Ile Leu Asp Ala Val Val Ala Gln Lys
1               5                   10

<210> SEQ ID NO 14
<211> LENGTH: 9
<212> TYPE: PRT
<213> ORGANISM: Homo sapiens

<400> SEQUENCE: 14

Glu Thr Val Ser Glu Gln Ser Asn Val
1               5

<210> SEQ ID NO 15
<211> LENGTH: 9
<212> TYPE: PRT
<213> ORGANISM: Homo sapiens

<400> SEQUENCE: 15

Arg Ile Ala Glu Cys Ile Leu Gly Met
1               5

<210> SEQ ID NO 16
<211> LENGTH: 15
<212> TYPE: PRT
<213> ORGANISM: Homo sapiens

<400> SEQUENCE: 16

Ile Gly Arg Ile Ala Glu Cys Ile Leu Gly Met Asn Pro Ser Arg
1               5                   10                  15

<210> SEQ ID NO 17
<211> LENGTH: 10
<212> TYPE: PRT
<213> ORGANISM: Homo sapiens

<400> SEQUENCE: 17
```

```
Tyr Val Asp Phe Arg Glu Tyr Glu Tyr Tyr
1               5                   10
```

<210> SEQ ID NO 18
<211> LENGTH: 14
<212> TYPE: PRT
<213> ORGANISM: Homo sapiens

<400> SEQUENCE: 18

```
Met Ile Phe Glu Lys His Gly Phe Arg Arg Thr Thr Pro Pro
1               5                   10
```

<210> SEQ ID NO 19
<211> LENGTH: 10
<212> TYPE: PRT
<213> ORGANISM: Homo sapiens

<400> SEQUENCE: 19

```
Thr Leu Asp Trp Leu Leu Gln Thr Pro Lys
1               5                   10
```

<210> SEQ ID NO 20
<211> LENGTH: 9
<212> TYPE: PRT
<213> ORGANISM: Homo sapiens

<400> SEQUENCE: 20

```
Trp Arg Arg Ala Pro Ala Pro Gly Ala
1               5
```

<210> SEQ ID NO 21
<211> LENGTH: 9
<212> TYPE: PRT
<213> ORGANISM: Homo sapiens

<400> SEQUENCE: 21

```
Pro Val Thr Trp Arg Arg Ala Pro Ala
1               5
```

<210> SEQ ID NO 22
<211> LENGTH: 10
<212> TYPE: PRT
<213> ORGANISM: Homo sapiens

<400> SEQUENCE: 22

```
Ser Leu Phe Glu Gly Ile Asp Ile Tyr Thr
1               5                   10
```

<210> SEQ ID NO 23
<211> LENGTH: 9
<212> TYPE: PRT
<213> ORGANISM: Homo sapiens

<400> SEQUENCE: 23

```
Ala Glu Pro Ile Asn Ile Gln Thr Trp
1               5
```

<210> SEQ ID NO 24
<211> LENGTH: 11
<212> TYPE: PRT
<213> ORGANISM: Homo sapiens

<400> SEQUENCE: 24

```
Phe Leu Glu Gly Asn Glu Val Gly Lys Thr Tyr
1               5                   10
```

<210> SEQ ID NO 25
<211> LENGTH: 9
<212> TYPE: PRT
<213> ORGANISM: Homo sapiens

<400> SEQUENCE: 25

Phe Leu Asp Glu Phe Met Glu Gly Val
1               5

<210> SEQ ID NO 26
<211> LENGTH: 9
<212> TYPE: PRT
<213> ORGANISM: Homo sapiens

<400> SEQUENCE: 26

Glu Glu Lys Leu Ile Val Val Leu Phe
1               5

<210> SEQ ID NO 27
<211> LENGTH: 11
<212> TYPE: PRT
<213> ORGANISM: Homo sapiens

<400> SEQUENCE: 27

Ser Glu Leu Phe Arg Ser Gly Leu Asp Ser Tyr
1               5                   10

<210> SEQ ID NO 28
<211> LENGTH: 9
<212> TYPE: PRT
<213> ORGANISM: Homo sapiens

<400> SEQUENCE: 28

Phe Arg Ser Gly Leu Asp Ser Tyr Val
1               5

<210> SEQ ID NO 29
<211> LENGTH: 9
<212> TYPE: PRT
<213> ORGANISM: Homo sapiens

<400> SEQUENCE: 29

Glu Ala Phe Ile Gln Pro Ile Thr Arg
1               5

<210> SEQ ID NO 30
<211> LENGTH: 11
<212> TYPE: PRT
<213> ORGANISM: Homo sapiens

<400> SEQUENCE: 30

Arg Val Ile Lys Asn Ser Ile Arg Leu Thr Leu
1               5                   10

<210> SEQ ID NO 31
<211> LENGTH: 9
<212> TYPE: PRT
<213> ORGANISM: Homo sapiens

<400> SEQUENCE: 31

Lys Ile Asn Lys Asn Pro Lys Tyr Lys
1               5

```
<210> SEQ ID NO 32
<211> LENGTH: 8
<212> TYPE: PRT
<213> ORGANISM: Homo sapiens

<400> SEQUENCE: 32

Gln Gln Ile Thr Lys Thr Glu Val
1               5

<210> SEQ ID NO 33
<211> LENGTH: 10
<212> TYPE: PRT
<213> ORGANISM: Homo sapiens

<400> SEQUENCE: 33

Ser Leu Tyr Lys Phe Ser Pro Phe Pro Leu
1               5                   10

<210> SEQ ID NO 34
<211> LENGTH: 9
<212> TYPE: PRT
<213> ORGANISM: Homo sapiens

<400> SEQUENCE: 34

Lys Glu Leu Glu Gly Ile Leu Leu Leu
1               5

<210> SEQ ID NO 35
<211> LENGTH: 9
<212> TYPE: PRT
<213> ORGANISM: Homo sapiens

<400> SEQUENCE: 35

Val Val Pro Cys Glu Pro Pro Glu Val
1               5

<210> SEQ ID NO 36
<211> LENGTH: 25
<212> TYPE: PRT
<213> ORGANISM: Homo sapiens

<400> SEQUENCE: 36

Asn Ser Asn His Val Ala Ser Gly Ala Gly Glu Ala Ala Ile Glu Thr
1               5                   10                  15

Gln Ser Ser Ser Ser Glu Glu Ile Val
            20                  25

<210> SEQ ID NO 37
<211> LENGTH: 10
<212> TYPE: PRT
<213> ORGANISM: Homo sapiens

<400> SEQUENCE: 37

Leu Leu Leu Asp Asp Leu Leu Val Ser Ile
1               5                   10

<210> SEQ ID NO 38
<211> LENGTH: 16
<212> TYPE: PRT
<213> ORGANISM: Homo sapiens

<400> SEQUENCE: 38

Pro Tyr Tyr Phe Ala Ala Glu Leu Pro Pro Arg Asn Leu Pro Glu Pro
1               5                   10                  15
```

```
<210> SEQ ID NO 39
<211> LENGTH: 9
<212> TYPE: PRT
<213> ORGANISM: Homo sapiens

<400> SEQUENCE: 39

Val Val Val Gly Ala Val Gly Val Gly
1               5

<210> SEQ ID NO 40
<211> LENGTH: 10
<212> TYPE: PRT
<213> ORGANISM: Homo sapiens

<400> SEQUENCE: 40

Ile Leu Asp Thr Ala Gly Arg Glu Glu Tyr
1               5                   10

<210> SEQ ID NO 41
<211> LENGTH: 9
<212> TYPE: PRT
<213> ORGANISM: Homo sapiens

<400> SEQUENCE: 41

Arg Pro His Val Pro Glu Ser Ala Phe
1               5

<210> SEQ ID NO 42
<211> LENGTH: 9
<212> TYPE: PRT
<213> ORGANISM: Homo sapiens

<400> SEQUENCE: 42

Lys Ile Phe Ser Glu Val Thr Leu Lys
1               5

<210> SEQ ID NO 43
<211> LENGTH: 9
<212> TYPE: PRT
<213> ORGANISM: Homo sapiens

<400> SEQUENCE: 43

Ser His Glu Thr Val Ile Ile Glu Leu
1               5

<210> SEQ ID NO 44
<211> LENGTH: 10
<212> TYPE: PRT
<213> ORGANISM: Homo sapiens

<400> SEQUENCE: 44

Gln Arg Pro Tyr Gly Tyr Asp Gln Ile Met
1               5                   10

<210> SEQ ID NO 45
<211> LENGTH: 9
<212> TYPE: PRT
<213> ORGANISM: Homo sapiens

<400> SEQUENCE: 45

Arg Leu Ser Ser Cys Val Pro Val Ala
1               5

<210> SEQ ID NO 46
```

-continued

```
<211> LENGTH: 15
<212> TYPE: PRT
<213> ORGANISM: Homo sapiens

<400> SEQUENCE: 46

Gly Glu Leu Ile Gly Ile Leu Asn Ala Ala Lys Val Pro Ala Asp
1               5                   10                  15

<210> SEQ ID NO 47
<211> LENGTH: 9
<212> TYPE: PRT
<213> ORGANISM: Homo sapiens

<400> SEQUENCE: 47

Ala Ala Arg Ala Val Phe Leu Ala Leu
1               5

<210> SEQ ID NO 48
<211> LENGTH: 8
<212> TYPE: PRT
<213> ORGANISM: Homo sapiens

<400> SEQUENCE: 48

Tyr Arg Pro Arg Pro Arg Arg Tyr
1               5

<210> SEQ ID NO 49
<211> LENGTH: 9
<212> TYPE: PRT
<213> ORGANISM: Homo sapiens

<400> SEQUENCE: 49

Tyr Tyr Trp Pro Arg Pro Arg Arg Tyr
1               5

<210> SEQ ID NO 50
<211> LENGTH: 10
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: May or may not be present

<400> SEQUENCE: 50

Val Leu Pro Asp Val Phe Ile Arg Cys Val
1               5                   10

<210> SEQ ID NO 51
<211> LENGTH: 9
<212> TYPE: PRT
<213> ORGANISM: Homo sapiens

<400> SEQUENCE: 51

Met Leu Ala Val Ile Ser Cys Ala Val
1               5

<210> SEQ ID NO 52
<211> LENGTH: 9
<212> TYPE: PRT
<213> ORGANISM: Homo sapiens

<400> SEQUENCE: 52

Arg Gln Lys Arg Ile Leu Val Asn Leu
1               5
```

<210> SEQ ID NO 53
<211> LENGTH: 9
<212> TYPE: PRT
<213> ORGANISM: Homo sapiens

<400> SEQUENCE: 53

Asn Tyr Asn Asn Phe Tyr Arg Phe Leu
1               5

<210> SEQ ID NO 54
<211> LENGTH: 10
<212> TYPE: PRT
<213> ORGANISM: Homo sapiens

<400> SEQUENCE: 54

Glu Tyr Ser Lys Glu Cys Leu Lys Glu Phe
1               5                   10

<210> SEQ ID NO 55
<211> LENGTH: 9
<212> TYPE: PRT
<213> ORGANISM: Homo sapiens

<400> SEQUENCE: 55

Glu Tyr Leu Ser Leu Ser Asp Lys Ile
1               5

<210> SEQ ID NO 56
<211> LENGTH: 11
<212> TYPE: PRT
<213> ORGANISM: Homo sapiens

<400> SEQUENCE: 56

Met Leu Met Ala Gln Glu Ala Leu Ala Phe Leu
1               5                   10

<210> SEQ ID NO 57
<211> LENGTH: 9
<212> TYPE: PRT
<213> ORGANISM: Homo sapiens

<400> SEQUENCE: 57

Ser Leu Leu Met Trp Ile Thr Gln Cys
1               5

<210> SEQ ID NO 58
<211> LENGTH: 10
<212> TYPE: PRT
<213> ORGANISM: Homo sapiens

<400> SEQUENCE: 58

Leu Ala Ala Gln Glu Arg Arg Val Pro Arg
1               5                   10

<210> SEQ ID NO 59
<211> LENGTH: 9
<212> TYPE: PRT
<213> ORGANISM: Homo sapiens

<400> SEQUENCE: 59

Glu Leu Val Arg Arg Ile Leu Ser Arg
1               5

<210> SEQ ID NO 60

```
<211> LENGTH: 9
<212> TYPE: PRT
<213> ORGANISM: Homo sapiens

<400> SEQUENCE: 60

Ala Pro Arg Gly Val Arg Met Ala Val
1               5

<210> SEQ ID NO 61
<211> LENGTH: 14
<212> TYPE: PRT
<213> ORGANISM: Homo sapiens

<400> SEQUENCE: 61

Ser Leu Leu Met Trp Ile Thr Gln Cys Phe Leu Pro Val Phe
1               5                   10

<210> SEQ ID NO 62
<211> LENGTH: 20
<212> TYPE: PRT
<213> ORGANISM: Homo sapiens

<400> SEQUENCE: 62

Gln Gly Ala Met Leu Ala Ala Gln Glu Arg Arg Val Pro Arg Ala Ala
1               5                   10                  15

Glu Val Pro Arg
            20

<210> SEQ ID NO 63
<211> LENGTH: 18
<212> TYPE: PRT
<213> ORGANISM: Homo sapiens

<400> SEQUENCE: 63

Ala Ala Asp His Arg Gln Leu Gln Leu Ser Ile Ser Ser Cys Leu Gln
1               5                   10                  15

Gln Leu

<210> SEQ ID NO 64
<211> LENGTH: 22
<212> TYPE: PRT
<213> ORGANISM: Homo sapiens

<400> SEQUENCE: 64

Cys Leu Ser Arg Arg Pro Trp Lys Arg Ser Trp Ser Ala Gly Ser Cys
1               5                   10                  15

Pro Gly Met Pro His Leu
            20

<210> SEQ ID NO 65
<211> LENGTH: 22
<212> TYPE: PRT
<213> ORGANISM: Homo sapiens

<400> SEQUENCE: 65

Cys Leu Ser Arg Arg Pro Trp Lys Arg Ser Trp Ser Ala Gly Ser Cys
1               5                   10                  15

Pro Gly Met Pro His Leu
            20

<210> SEQ ID NO 66
<211> LENGTH: 13
<212> TYPE: PRT
```

```
<213> ORGANISM: Homo sapiens

<400> SEQUENCE: 66

Ile Leu Ser Arg Asp Ala Ala Pro Leu Pro Arg Pro Gly
1               5                   10

<210> SEQ ID NO 67
<211> LENGTH: 14
<212> TYPE: PRT
<213> ORGANISM: Homo sapiens

<400> SEQUENCE: 67

Ala Gly Ala Thr Gly Gly Arg Gly Pro Arg Gly Ala Gly Ala
1               5                   10

<210> SEQ ID NO 68
<211> LENGTH: 9
<212> TYPE: PRT
<213> ORGANISM: Homo sapiens

<400> SEQUENCE: 68

Glu Ala Asp Pro Thr Gly His Ser Tyr
1               5

<210> SEQ ID NO 69
<211> LENGTH: 9
<212> TYPE: PRT
<213> ORGANISM: Homo sapiens

<400> SEQUENCE: 69

Lys Val Leu Glu Tyr Val Ile Lys Val
1               5

<210> SEQ ID NO 70
<211> LENGTH: 9
<212> TYPE: PRT
<213> ORGANISM: Homo sapiens

<400> SEQUENCE: 70

Ser Leu Phe Arg Ala Val Ile Thr Lys
1               5

<210> SEQ ID NO 71
<211> LENGTH: 10
<212> TYPE: PRT
<213> ORGANISM: Homo sapiens

<400> SEQUENCE: 71

Glu Val Tyr Asp Gly Arg Glu His Ser Ala
1               5                   10

<210> SEQ ID NO 72
<211> LENGTH: 9
<212> TYPE: PRT
<213> ORGANISM: Homo sapiens

<400> SEQUENCE: 72

Arg Val Arg Phe Phe Phe Pro Ser Leu
1               5

<210> SEQ ID NO 73
<211> LENGTH: 9
<212> TYPE: PRT
<213> ORGANISM: Homo sapiens
```

<400> SEQUENCE: 73

Glu Ala Asp Pro Thr Gly His Ser Tyr
1               5

<210> SEQ ID NO 74
<211> LENGTH: 10
<212> TYPE: PRT
<213> ORGANISM: Homo sapiens

<400> SEQUENCE: 74

Arg Glu Pro Val Thr Lys Ala Glu Met Leu
1               5                   10

<210> SEQ ID NO 75
<211> LENGTH: 9
<212> TYPE: PRT
<213> ORGANISM: Homo sapiens

<400> SEQUENCE: 75

Asp Pro Ala Arg Tyr Glu Phe Leu Trp
1               5

<210> SEQ ID NO 76
<211> LENGTH: 11
<212> TYPE: PRT
<213> ORGANISM: Homo sapiens

<400> SEQUENCE: 76

Ile Thr Lys Lys Val Ala Asp Leu Val Gly Phe
1               5                   10

<210> SEQ ID NO 77
<211> LENGTH: 9
<212> TYPE: PRT
<213> ORGANISM: Homo sapiens

<400> SEQUENCE: 77

Ser Ala Phe Pro Thr Thr Ile Asn Phe
1               5

<210> SEQ ID NO 78
<211> LENGTH: 9
<212> TYPE: PRT
<213> ORGANISM: Homo sapiens

<400> SEQUENCE: 78

Ser Ala Tyr Gly Glu Pro Arg Lys Leu
1               5

<210> SEQ ID NO 79
<211> LENGTH: 9
<212> TYPE: PRT
<213> ORGANISM: Homo sapiens

<400> SEQUENCE: 79

Ser Ala Tyr Gly Glu Pro Arg Lys Leu
1               5

<210> SEQ ID NO 80
<211> LENGTH: 15
<212> TYPE: PRT
<213> ORGANISM: Homo sapiens

<400> SEQUENCE: 80

Thr Ser Cys Ile Leu Glu Ser Leu Phe Arg Ala Val Ile Thr Lys
1               5                   10                  15

<210> SEQ ID NO 81
<211> LENGTH: 15
<212> TYPE: PRT
<213> ORGANISM: Homo sapiens

<400> SEQUENCE: 81

Pro Arg Ala Leu Ala Glu Thr Ser Tyr Val Lys Val Leu Glu Tyr
1               5                   10                  15

<210> SEQ ID NO 82
<211> LENGTH: 16
<212> TYPE: PRT
<213> ORGANISM: Homo sapiens

<400> SEQUENCE: 82

Phe Leu Leu Leu Lys Tyr Arg Ala Arg Glu Pro Val Thr Lys Ala Glu
1               5                   10                  15

<210> SEQ ID NO 83
<211> LENGTH: 12
<212> TYPE: PRT
<213> ORGANISM: Homo sapiens

<400> SEQUENCE: 83

Glu Tyr Val Ile Lys Val Ser Ala Arg Val Arg Phe
1               5                   10

<210> SEQ ID NO 84
<211> LENGTH: 10
<212> TYPE: PRT
<213> ORGANISM: Homo sapiens

<400> SEQUENCE: 84

Tyr Leu Gln Leu Val Phe Gly Ile Glu Val
1               5                   10

<210> SEQ ID NO 85
<211> LENGTH: 9
<212> TYPE: PRT
<213> ORGANISM: Homo sapiens

<400> SEQUENCE: 85

Glu Tyr Leu Gln Leu Val Phe Gly Ile
1               5

<210> SEQ ID NO 86
<211> LENGTH: 10
<212> TYPE: PRT
<213> ORGANISM: Homo sapiens

<400> SEQUENCE: 86

Arg Glu Pro Val Thr Lys Ala Glu Met Leu
1               5                   10

<210> SEQ ID NO 87
<211> LENGTH: 9
<212> TYPE: PRT
<213> ORGANISM: Homo sapiens

<400> SEQUENCE: 87

Glu Gly Asp Cys Ala Pro Glu Glu Lys
1               5

```
<210> SEQ ID NO 88
<211> LENGTH: 14
<212> TYPE: PRT
<213> ORGANISM: Homo sapiens

<400> SEQUENCE: 88

Leu Leu Lys Tyr Arg Ala Arg Glu Pro Val Thr Lys Ala Glu
1               5                   10

<210> SEQ ID NO 89
<211> LENGTH: 9
<212> TYPE: PRT
<213> ORGANISM: Homo sapiens

<400> SEQUENCE: 89

Glu Val Asp Pro Ile Gly His Leu Tyr
1               5

<210> SEQ ID NO 90
<211> LENGTH: 9
<212> TYPE: PRT
<213> ORGANISM: Homo sapiens

<400> SEQUENCE: 90

Phe Leu Trp Gly Pro Arg Ala Leu Val
1               5

<210> SEQ ID NO 91
<211> LENGTH: 9
<212> TYPE: PRT
<213> ORGANISM: Homo sapiens

<400> SEQUENCE: 91

Lys Val Ala Glu Leu Val His Phe Leu
1               5

<210> SEQ ID NO 92
<211> LENGTH: 9
<212> TYPE: PRT
<213> ORGANISM: Homo sapiens

<400> SEQUENCE: 92

Thr Phe Pro Asp Leu Glu Ser Glu Phe
1               5

<210> SEQ ID NO 93
<211> LENGTH: 9
<212> TYPE: PRT
<213> ORGANISM: Homo sapiens

<400> SEQUENCE: 93

Val Ala Glu Leu Val His Phe Leu Leu
1               5

<210> SEQ ID NO 94
<211> LENGTH: 10
<212> TYPE: PRT
<213> ORGANISM: Homo sapiens

<400> SEQUENCE: 94

Met Glu Val Asp Pro Ile Gly His Leu Tyr
1               5                   10
```

```
<210> SEQ ID NO 95
<211> LENGTH: 9
<212> TYPE: PRT
<213> ORGANISM: Homo sapiens

<400> SEQUENCE: 95

Glu Val Asp Pro Ile Gly His Leu Tyr
1               5

<210> SEQ ID NO 96
<211> LENGTH: 10
<212> TYPE: PRT
<213> ORGANISM: Homo sapiens

<400> SEQUENCE: 96

Arg Glu Pro Val Thr Lys Ala Glu Met Leu
1               5                   10

<210> SEQ ID NO 97
<211> LENGTH: 9
<212> TYPE: PRT
<213> ORGANISM: Homo sapiens

<400> SEQUENCE: 97

Ala Glu Leu Val His Phe Leu Leu Leu
1               5

<210> SEQ ID NO 98
<211> LENGTH: 10
<212> TYPE: PRT
<213> ORGANISM: Homo sapiens

<400> SEQUENCE: 98

Met Glu Val Asp Pro Ile Gly His Leu Tyr
1               5                   10

<210> SEQ ID NO 99
<211> LENGTH: 9
<212> TYPE: PRT
<213> ORGANISM: Homo sapiens

<400> SEQUENCE: 99

Trp Gln Tyr Phe Phe Pro Val Ile Phe
1               5

<210> SEQ ID NO 100
<211> LENGTH: 9
<212> TYPE: PRT
<213> ORGANISM: Homo sapiens

<400> SEQUENCE: 100

Glu Gly Asp Cys Ala Pro Glu Glu Lys
1               5

<210> SEQ ID NO 101
<211> LENGTH: 16
<212> TYPE: PRT
<213> ORGANISM: Homo sapiens

<400> SEQUENCE: 101

Lys Lys Leu Leu Thr Gln His Phe Val Gln Glu Asn Tyr Leu Glu Tyr
1               5                   10                  15

<210> SEQ ID NO 102
<211> LENGTH: 16
```

```
<212> TYPE: PRT
<213> ORGANISM: Homo sapiens

<400> SEQUENCE: 102

Lys Lys Leu Leu Thr Gln His Phe Val Gln Glu Asn Tyr Leu Glu Tyr
1               5                   10                  15

<210> SEQ ID NO 103
<211> LENGTH: 16
<212> TYPE: PRT
<213> ORGANISM: Homo sapiens

<400> SEQUENCE: 103

Ala Cys Tyr Glu Phe Leu Trp Gly Pro Arg Ala Leu Val Glu Thr Ser
1               5                   10                  15

<210> SEQ ID NO 104
<211> LENGTH: 12
<212> TYPE: PRT
<213> ORGANISM: Homo sapiens

<400> SEQUENCE: 104

Val Ile Phe Ser Lys Ala Ser Ser Ser Leu Gln Leu
1               5                   10

<210> SEQ ID NO 105
<211> LENGTH: 12
<212> TYPE: PRT
<213> ORGANISM: Homo sapiens

<400> SEQUENCE: 105

Val Ile Phe Ser Lys Ala Ser Ser Leu Gln Leu
1               5                   10

<210> SEQ ID NO 106
<211> LENGTH: 15
<212> TYPE: PRT
<213> ORGANISM: Homo sapiens

<400> SEQUENCE: 106

Gly Asp Asn Gln Ile Met Pro Lys Ala Gly Leu Leu Ile Ile Val
1               5                   10                  15

<210> SEQ ID NO 107
<211> LENGTH: 15
<212> TYPE: PRT
<213> ORGANISM: Homo sapiens

<400> SEQUENCE: 107

Thr Ser Tyr Val Lys Val Leu His His Met Val Lys Ile Ser Gly
1               5                   10                  15

<210> SEQ ID NO 108
<211> LENGTH: 16
<212> TYPE: PRT
<213> ORGANISM: Homo sapiens

<400> SEQUENCE: 108

Arg Lys Val Ala Glu Leu Val His Phe Leu Leu Leu Lys Tyr Arg Ala
1               5                   10                  15

<210> SEQ ID NO 109
<211> LENGTH: 16
<212> TYPE: PRT
<213> ORGANISM: Homo sapiens
```

<400> SEQUENCE: 109

Phe Leu Leu Leu Lys Tyr Arg Ala Arg Glu Pro Val Thr Lys Ala Glu
1               5                   10                  15

<210> SEQ ID NO 110
<211> LENGTH: 9
<212> TYPE: PRT
<213> ORGANISM: Homo sapiens

<400> SEQUENCE: 110

Glu Val Asp Pro Ala Ser Asn Thr Tyr
1               5

<210> SEQ ID NO 111
<211> LENGTH: 10
<212> TYPE: PRT
<213> ORGANISM: Homo sapiens

<400> SEQUENCE: 111

Gly Val Tyr Asp Gly Arg Glu His Thr Val
1               5                   10

<210> SEQ ID NO 112
<211> LENGTH: 9
<212> TYPE: PRT
<213> ORGANISM: Homo sapiens

<400> SEQUENCE: 112

Asn Tyr Lys Arg Cys Phe Pro Val Ile
1               5

<210> SEQ ID NO 113
<211> LENGTH: 8
<212> TYPE: PRT
<213> ORGANISM: Homo sapiens

<400> SEQUENCE: 113

Ser Glu Ser Leu Lys Met Ile Phe
1               5

<210> SEQ ID NO 114
<211> LENGTH: 9
<212> TYPE: PRT
<213> ORGANISM: Homo sapiens

<400> SEQUENCE: 114

Met Val Lys Ile Ser Gly Gly Pro Arg
1               5

<210> SEQ ID NO 115
<211> LENGTH: 9
<212> TYPE: PRT
<213> ORGANISM: Homo sapiens

<400> SEQUENCE: 115

Glu Val Asp Pro Ile Gly His Val Tyr
1               5

<210> SEQ ID NO 116
<211> LENGTH: 10
<212> TYPE: PRT
<213> ORGANISM: Homo sapiens

<400> SEQUENCE: 116

```
Arg Glu Pro Val Thr Lys Ala Glu Met Leu
1               5                   10

<210> SEQ ID NO 117
<211> LENGTH: 9
<212> TYPE: PRT
<213> ORGANISM: Homo sapiens

<400> SEQUENCE: 117

Glu Gly Asp Cys Ala Pro Glu Glu Lys
1               5

<210> SEQ ID NO 118
<211> LENGTH: 9
<212> TYPE: PRT
<213> ORGANISM: Homo sapiens

<400> SEQUENCE: 118

Ile Ser Gly Gly Pro Arg Ile Ser Tyr
1               5

<210> SEQ ID NO 119
<211> LENGTH: 14
<212> TYPE: PRT
<213> ORGANISM: Homo sapiens

<400> SEQUENCE: 119

Leu Leu Lys Tyr Arg Ala Arg Glu Pro Val Thr Lys Ala Glu
1               5                   10

<210> SEQ ID NO 120
<211> LENGTH: 9
<212> TYPE: PRT
<213> ORGANISM: Homo sapiens

<400> SEQUENCE: 120

Ala Leu Ser Val Met Gly Val Tyr Val
1               5

<210> SEQ ID NO 121
<211> LENGTH: 9
<212> TYPE: PRT
<213> ORGANISM: Homo sapiens

<400> SEQUENCE: 121

Gly Leu Tyr Asp Gly Met Glu His Leu
1               5

<210> SEQ ID NO 122
<211> LENGTH: 9
<212> TYPE: PRT
<213> ORGANISM: Homo sapiens

<400> SEQUENCE: 122

Asp Pro Ala Arg Tyr Glu Phe Leu Trp
1               5

<210> SEQ ID NO 123
<211> LENGTH: 9
<212> TYPE: PRT
<213> ORGANISM: Homo sapiens

<400> SEQUENCE: 123

Phe Leu Trp Gly Pro Arg Ala Leu Val
```

```
<210> SEQ ID NO 124
<211> LENGTH: 9
<212> TYPE: PRT
<213> ORGANISM: Homo sapiens

<400> SEQUENCE: 124

Val Arg Ile Gly His Leu Tyr Ile Leu
1               5

<210> SEQ ID NO 125
<211> LENGTH: 9
<212> TYPE: PRT
<213> ORGANISM: Homo sapiens

<400> SEQUENCE: 125

Glu Gly Asp Cys Ala Pro Glu Glu Lys
1               5

<210> SEQ ID NO 126
<211> LENGTH: 15
<212> TYPE: PRT
<213> ORGANISM: Homo sapiens

<400> SEQUENCE: 126

Arg Glu Pro Phe Thr Lys Ala Glu Met Leu Gly Ser Val Ile Arg
1               5                   10                  15

<210> SEQ ID NO 127
<211> LENGTH: 14
<212> TYPE: PRT
<213> ORGANISM: Homo sapiens

<400> SEQUENCE: 127

Ala Glu Leu Val His Phe Leu Leu Leu Lys Tyr Arg Ala Arg
1               5                   10

<210> SEQ ID NO 128
<211> LENGTH: 10
<212> TYPE: PRT
<213> ORGANISM: Homo sapiens

<400> SEQUENCE: 128

Leu Leu Phe Gly Leu Ala Leu Ile Glu Val
1               5                   10

<210> SEQ ID NO 129
<211> LENGTH: 9
<212> TYPE: PRT
<213> ORGANISM: Homo sapiens

<400> SEQUENCE: 129

Ala Leu Lys Asp Val Glu Glu Arg Val
1               5

<210> SEQ ID NO 130
<211> LENGTH: 9
<212> TYPE: PRT
<213> ORGANISM: Homo sapiens

<400> SEQUENCE: 130

Ser Glu Ser Ile Lys Lys Lys Val Leu
1               5
```

```
<210> SEQ ID NO 131
<211> LENGTH: 20
<212> TYPE: PRT
<213> ORGANISM: Homo sapiens

<400> SEQUENCE: 131

Pro Asp Thr Arg Pro Ala Pro Gly Ser Thr Ala Pro Pro Ala His Gly
1               5                   10                  15

Val Thr Ser Ala
            20

<210> SEQ ID NO 132
<211> LENGTH: 9
<212> TYPE: PRT
<213> ORGANISM: Homo sapiens

<400> SEQUENCE: 132

Gln Gly Gln His Phe Leu Gln Lys Val
1               5

<210> SEQ ID NO 133
<211> LENGTH: 9
<212> TYPE: PRT
<213> ORGANISM: Homo sapiens

<400> SEQUENCE: 133

Ser Leu Leu Met Trp Ile Thr Gln Cys
1               5

<210> SEQ ID NO 134
<211> LENGTH: 11
<212> TYPE: PRT
<213> ORGANISM: Homo sapiens

<400> SEQUENCE: 134

Met Leu Met Ala Gln Glu Ala Leu Ala Phe Leu
1               5                   10

<210> SEQ ID NO 135
<211> LENGTH: 10
<212> TYPE: PRT
<213> ORGANISM: Homo sapiens

<400> SEQUENCE: 135

Ala Ser Gly Pro Gly Gly Gly Ala Pro Arg
1               5                   10

<210> SEQ ID NO 136
<211> LENGTH: 10
<212> TYPE: PRT
<213> ORGANISM: Homo sapiens

<400> SEQUENCE: 136

Leu Ala Ala Gln Glu Arg Arg Val Pro Arg
1               5                   10

<210> SEQ ID NO 137
<211> LENGTH: 10
<212> TYPE: PRT
<213> ORGANISM: Homo sapiens

<400> SEQUENCE: 137

Thr Val Ser Gly Asn Ile Leu Thr Ile Arg
1               5                   10
```

<210> SEQ ID NO 138
<211> LENGTH: 13
<212> TYPE: PRT
<213> ORGANISM: Homo sapiens

<400> SEQUENCE: 138

Ala Pro Arg Gly Pro His Gly Gly Ala Ala Ser Gly Leu
1               5                   10

<210> SEQ ID NO 139
<211> LENGTH: 9
<212> TYPE: PRT
<213> ORGANISM: Homo sapiens

<400> SEQUENCE: 139

Met Pro Phe Ala Thr Pro Met Glu Ala
1               5

<210> SEQ ID NO 140
<211> LENGTH: 12
<212> TYPE: PRT
<213> ORGANISM: Homo sapiens

<400> SEQUENCE: 140

Lys Glu Phe Thr Val Ser Gly Asn Ile Leu Thr Ile
1               5                   10

<210> SEQ ID NO 141
<211> LENGTH: 9
<212> TYPE: PRT
<213> ORGANISM: Homo sapiens

<400> SEQUENCE: 141

Met Pro Phe Ala Thr Pro Met Glu Ala
1               5

<210> SEQ ID NO 142
<211> LENGTH: 9
<212> TYPE: PRT
<213> ORGANISM: Homo sapiens

<400> SEQUENCE: 142

Leu Ala Met Pro Phe Ala Thr Pro Met
1               5

<210> SEQ ID NO 143
<211> LENGTH: 9
<212> TYPE: PRT
<213> ORGANISM: Homo sapiens

<400> SEQUENCE: 143

Ala Arg Gly Pro Glu Ser Arg Leu Leu
1               5

<210> SEQ ID NO 144
<211> LENGTH: 14
<212> TYPE: PRT
<213> ORGANISM: Homo sapiens

<400> SEQUENCE: 144

Ser Leu Leu Met Trp Ile Thr Gln Cys Phe Leu Pro Val Phe
1               5                   10

```
<210> SEQ ID NO 145
<211> LENGTH: 25
<212> TYPE: PRT
<213> ORGANISM: Homo sapiens

<400> SEQUENCE: 145

Leu Leu Glu Phe Tyr Leu Ala Met Pro Phe Ala Thr Pro Met Glu Ala
1               5                   10                  15

Glu Leu Ala Arg Arg Ser Leu Ala Gln
            20                  25

<210> SEQ ID NO 146
<211> LENGTH: 25
<212> TYPE: PRT
<213> ORGANISM: Homo sapiens

<400> SEQUENCE: 146

Leu Leu Glu Phe Tyr Leu Ala Met Pro Phe Ala Thr Pro Met Glu Ala
1               5                   10                  15

Glu Leu Ala Arg Arg Ser Leu Ala Gln
            20                  25

<210> SEQ ID NO 147
<211> LENGTH: 12
<212> TYPE: PRT
<213> ORGANISM: Homo sapiens

<400> SEQUENCE: 147

Glu Phe Tyr Leu Ala Met Pro Phe Ala Thr Pro Met
1               5                   10

<210> SEQ ID NO 148
<211> LENGTH: 12
<212> TYPE: PRT
<213> ORGANISM: Homo sapiens

<400> SEQUENCE: 148

Arg Leu Leu Glu Phe Tyr Leu Ala Met Pro Phe Ala
1               5                   10

<210> SEQ ID NO 149
<211> LENGTH: 20
<212> TYPE: PRT
<213> ORGANISM: Homo sapiens

<400> SEQUENCE: 149

Gln Gly Ala Met Leu Ala Ala Gln Glu Arg Arg Val Pro Arg Ala Ala
1               5                   10                  15

Glu Val Pro Arg
            20

<210> SEQ ID NO 150
<211> LENGTH: 20
<212> TYPE: PRT
<213> ORGANISM: Homo sapiens

<400> SEQUENCE: 150

Pro Gly Val Leu Leu Lys Glu Phe Thr Val Ser Gly Asn Ile Leu Thr
1               5                   10                  15

Ile Arg Leu Thr
            20

<210> SEQ ID NO 151
```

<211> LENGTH: 10
<212> TYPE: PRT
<213> ORGANISM: Homo sapiens

<400> SEQUENCE: 151

Val Leu Leu Lys Glu Phe Thr Val Ser Gly
1               5                   10

<210> SEQ ID NO 152
<211> LENGTH: 18
<212> TYPE: PRT
<213> ORGANISM: Homo sapiens

<400> SEQUENCE: 152

Ala Ala Asp His Arg Gln Leu Gln Leu Ser Ile Ser Ser Cys Leu Gln
1               5                   10                  15

Gln Leu

<210> SEQ ID NO 153
<211> LENGTH: 25
<212> TYPE: PRT
<213> ORGANISM: Homo sapiens

<400> SEQUENCE: 153

Leu Leu Glu Phe Tyr Leu Ala Met Pro Phe Ala Thr Pro Met Glu Ala
1               5                   10                  15

Glu Leu Ala Arg Arg Ser Leu Ala Gln
            20                  25

<210> SEQ ID NO 154
<211> LENGTH: 25
<212> TYPE: PRT
<213> ORGANISM: Homo sapiens

<400> SEQUENCE: 154

Pro Gly Val Leu Leu Lys Glu Phe Thr Val Ser Gly Asn Ile Leu Thr
1               5                   10                  15

Ile Arg Leu Thr Ala Ala Asp His Arg
            20                  25

<210> SEQ ID NO 155
<211> LENGTH: 25
<212> TYPE: PRT
<213> ORGANISM: Homo sapiens

<400> SEQUENCE: 155

Leu Leu Glu Phe Tyr Leu Ala Met Pro Phe Ala Thr Pro Met Glu Ala
1               5                   10                  15

Glu Leu Ala Arg Arg Ser Leu Ala Gln
            20                  25

<210> SEQ ID NO 156
<211> LENGTH: 14
<212> TYPE: PRT
<213> ORGANISM: Homo sapiens

<400> SEQUENCE: 156

Ala Gly Ala Thr Gly Gly Arg Gly Pro Arg Gly Ala Gly Ala
1               5                   10

<210> SEQ ID NO 157
<211> LENGTH: 9
<212> TYPE: PRT

```
<213> ORGANISM: Homo sapiens

<400> SEQUENCE: 157

Leu Tyr Ala Thr Val Ile His Asp Ile
1               5

<210> SEQ ID NO 158
<211> LENGTH: 9
<212> TYPE: PRT
<213> ORGANISM: Homo sapiens

<400> SEQUENCE: 158

Ile Leu Asp Ser Ser Glu Glu Asp Lys
1               5

<210> SEQ ID NO 159
<211> LENGTH: 9
<212> TYPE: PRT
<213> ORGANISM: Homo sapiens

<400> SEQUENCE: 159

Lys Ala Ser Glu Lys Ile Phe Tyr Val
1               5

<210> SEQ ID NO 160
<211> LENGTH: 16
<212> TYPE: PRT
<213> ORGANISM: Homo sapiens

<400> SEQUENCE: 160

Glu Lys Ile Gln Lys Ala Phe Asp Asp Ile Ala Lys Tyr Phe Ser Lys
1               5                   10                  15

<210> SEQ ID NO 161
<211> LENGTH: 18
<212> TYPE: PRT
<213> ORGANISM: Homo sapiens

<400> SEQUENCE: 161

Trp Glu Lys Met Lys Ala Ser Glu Lys Ile Phe Tyr Val Tyr Met Lys
1               5                   10                  15

Arg Lys

<210> SEQ ID NO 162
<211> LENGTH: 15
<212> TYPE: PRT
<213> ORGANISM: Homo sapiens

<400> SEQUENCE: 162

Lys Ile Phe Tyr Val Tyr Met Lys Arg Lys Tyr Glu Ala Met Thr
1               5                   10                  15

<210> SEQ ID NO 163
<211> LENGTH: 14
<212> TYPE: PRT
<213> ORGANISM: Homo sapiens

<400> SEQUENCE: 163

Lys Ile Phe Tyr Val Tyr Met Lys Arg Lys Tyr Glu Ala Met
1               5                   10

<210> SEQ ID NO 164
<211> LENGTH: 20
<212> TYPE: PRT
```

```
<213> ORGANISM: Homo sapiens

<400> SEQUENCE: 164

Ile Asn Lys Thr Ser Gly Pro Lys Arg Gly Lys His Ala Trp Thr His
1               5                   10                  15

Arg Leu Arg Glu
            20

<210> SEQ ID NO 165
<211> LENGTH: 20
<212> TYPE: PRT
<213> ORGANISM: Homo sapiens

<400> SEQUENCE: 165

Tyr Phe Ser Lys Lys Glu Trp Glu Lys Met Lys Ser Ser Glu Lys Ile
1               5                   10                  15

Val Tyr Val Tyr
            20

<210> SEQ ID NO 166
<211> LENGTH: 20
<212> TYPE: PRT
<213> ORGANISM: Homo sapiens

<400> SEQUENCE: 166

Met Lys Leu Asn Tyr Glu Val Met Thr Lys Leu Gly Phe Lys Val Thr
1               5                   10                  15

Leu Pro Pro Phe
            20

<210> SEQ ID NO 167
<211> LENGTH: 20
<212> TYPE: PRT
<213> ORGANISM: Homo sapiens

<400> SEQUENCE: 167

Lys His Ala Trp Thr His Arg Leu Arg Glu Arg Lys Gln Leu Val Val
1               5                   10                  15

Tyr Glu Glu Ile
            20

<210> SEQ ID NO 168
<211> LENGTH: 20
<212> TYPE: PRT
<213> ORGANISM: Homo sapiens

<400> SEQUENCE: 168

Leu Gly Phe Lys Val Thr Leu Pro Pro Phe Met Arg Ser Lys Arg Ala
1               5                   10                  15

Ala Asp Phe His
            20

<210> SEQ ID NO 169
<211> LENGTH: 20
<212> TYPE: PRT
<213> ORGANISM: Homo sapiens

<400> SEQUENCE: 169

Lys Ser Ser Glu Lys Ile Val Tyr Val Tyr Met Lys Leu Asn Tyr Glu
1               5                   10                  15

Val Met Thr Lys
            20
```

<210> SEQ ID NO 170
<211> LENGTH: 20
<212> TYPE: PRT
<213> ORGANISM: Homo sapiens

<400> SEQUENCE: 170

Lys His Ala Trp Thr His Arg Leu Arg Glu Arg Lys Gln Leu Val Val
1               5                   10                  15

Tyr Glu Glu Ile
            20

<210> SEQ ID NO 171
<211> LENGTH: 9
<212> TYPE: PRT
<213> ORGANISM: Homo sapiens

<400> SEQUENCE: 171

Ser Leu Gly Trp Leu Phe Leu Leu Leu
1               5

<210> SEQ ID NO 172
<211> LENGTH: 9
<212> TYPE: PRT
<213> ORGANISM: Homo sapiens

<400> SEQUENCE: 172

Leu Ser Arg Leu Ser Asn Arg Leu Leu
1               5

<210> SEQ ID NO 173
<211> LENGTH: 9
<212> TYPE: PRT
<213> ORGANISM: Homo sapiens

<400> SEQUENCE: 173

Leu Ser Arg Leu Ser Asn Arg Leu Leu
1               5

<210> SEQ ID NO 174
<211> LENGTH: 15
<212> TYPE: PRT
<213> ORGANISM: Homo sapiens

<400> SEQUENCE: 174

Cys Glu Phe His Ala Cys Trp Pro Ala Phe Thr Val Leu Gly Glu
1               5                   10                  15

<210> SEQ ID NO 175
<211> LENGTH: 15
<212> TYPE: PRT
<213> ORGANISM: Homo sapiens

<400> SEQUENCE: 175

Cys Glu Phe His Ala Cys Trp Pro Ala Phe Thr Val Leu Gly Glu
1               5                   10                  15

<210> SEQ ID NO 176
<211> LENGTH: 15
<212> TYPE: PRT
<213> ORGANISM: Homo sapiens

<400> SEQUENCE: 176

Cys Glu Phe His Ala Cys Trp Pro Ala Phe Thr Val Leu Gly Glu

```
                1               5                  10                 15
```

<210> SEQ ID NO 177
<211> LENGTH: 10
<212> TYPE: PRT
<213> ORGANISM: Homo sapiens

<400> SEQUENCE: 177

```
Glu Val Ile Ser Cys Lys Leu Ile Lys Arg
1               5                  10
```

<210> SEQ ID NO 178
<211> LENGTH: 17
<212> TYPE: PRT
<213> ORGANISM: Homo sapiens

<400> SEQUENCE: 178

```
Cys Ala Thr Trp Lys Val Ile Cys Lys Ser Cys Ile Ser Gln Thr Pro
1               5                  10                  15
Gly
```

<210> SEQ ID NO 179
<211> LENGTH: 9
<212> TYPE: PRT
<213> ORGANISM: Homo sapiens

<400> SEQUENCE: 179

```
Tyr Leu Ser Gly Ala Asn Leu Asn Leu
1               5
```

<210> SEQ ID NO 180
<211> LENGTH: 9
<212> TYPE: PRT
<213> ORGANISM: Homo sapiens

<400> SEQUENCE: 180

```
Ile Met Ile Gly Val Leu Val Gly Val
1               5
```

<210> SEQ ID NO 181
<211> LENGTH: 9
<212> TYPE: PRT
<213> ORGANISM: Homo sapiens

<400> SEQUENCE: 181

```
Gly Val Leu Val Gly Val Ala Leu Ile
1               5
```

<210> SEQ ID NO 182
<211> LENGTH: 9
<212> TYPE: PRT
<213> ORGANISM: Homo sapiens

<400> SEQUENCE: 182

```
His Leu Phe Gly Tyr Ser Trp Tyr Lys
1               5
```

<210> SEQ ID NO 183
<211> LENGTH: 10
<212> TYPE: PRT
<213> ORGANISM: Homo sapiens

<400> SEQUENCE: 183

```
Gln Tyr Ser Trp Phe Val Asn Gly Thr Phe
```

```
<210> SEQ ID NO 184
<211> LENGTH: 9
<212> TYPE: PRT
<213> ORGANISM: Homo sapiens

<400> SEQUENCE: 184

Thr Tyr Ala Cys Phe Val Ser Asn Leu
1               5

<210> SEQ ID NO 185
<211> LENGTH: 15
<212> TYPE: PRT
<213> ORGANISM: Homo sapiens

<400> SEQUENCE: 185

Ala Tyr Val Cys Gly Ile Gln Asn Ser Val Ser Ala Asn Arg Ser
1               5                   10                  15

<210> SEQ ID NO 186
<211> LENGTH: 25
<212> TYPE: PRT
<213> ORGANISM: Homo sapiens

<400> SEQUENCE: 186

Asp Thr Gly Phe Tyr Thr Leu His Val Ile Lys Ser Asp Leu Val Asn
1               5                   10                  15

Glu Glu Ala Thr Gly Gln Phe Arg Val
            20                  25

<210> SEQ ID NO 187
<211> LENGTH: 15
<212> TYPE: PRT
<213> ORGANISM: Homo sapiens

<400> SEQUENCE: 187

Tyr Ser Trp Arg Ile Asn Gly Ile Pro Gln Gln His Thr Gln Val
1               5                   10                  15

<210> SEQ ID NO 188
<211> LENGTH: 13
<212> TYPE: PRT
<213> ORGANISM: Homo sapiens

<400> SEQUENCE: 188

Thr Tyr Tyr Arg Pro Gly Val Asn Leu Ser Leu Ser Cys
1               5                   10

<210> SEQ ID NO 189
<211> LENGTH: 13
<212> TYPE: PRT
<213> ORGANISM: Homo sapiens

<400> SEQUENCE: 189

Glu Ile Ile Tyr Pro Asn Ala Ser Leu Leu Ile Gln Asn
1               5                   10

<210> SEQ ID NO 190
<211> LENGTH: 15
<212> TYPE: PRT
<213> ORGANISM: Homo sapiens

<400> SEQUENCE: 190
```

```
Tyr Ala Cys Phe Val Ser Asn Leu Ala Thr Gly Arg Asn Asn Ser
1               5                   10                  15
```

<210> SEQ ID NO 191
<211> LENGTH: 13
<212> TYPE: PRT
<213> ORGANISM: Homo sapiens

<400> SEQUENCE: 191

```
Leu Trp Trp Val Asn Asn Gln Ser Leu Pro Val Ser Pro
1               5                   10
```

<210> SEQ ID NO 192
<211> LENGTH: 13
<212> TYPE: PRT
<213> ORGANISM: Homo sapiens

<400> SEQUENCE: 192

```
Leu Trp Trp Val Asn Asn Gln Ser Leu Pro Val Ser Pro
1               5                   10
```

<210> SEQ ID NO 193
<211> LENGTH: 13
<212> TYPE: PRT
<213> ORGANISM: Homo sapiens

<400> SEQUENCE: 193

```
Leu Trp Trp Val Asn Asn Gln Ser Leu Pro Val Ser Pro
1               5                   10
```

<210> SEQ ID NO 194
<211> LENGTH: 13
<212> TYPE: PRT
<213> ORGANISM: Homo sapiens

<400> SEQUENCE: 194

```
Glu Ile Ile Tyr Pro Asn Ala Ser Leu Leu Ile Gln Asn
1               5                   10
```

<210> SEQ ID NO 195
<211> LENGTH: 13
<212> TYPE: PRT
<213> ORGANISM: Homo sapiens

<400> SEQUENCE: 195

```
Asn Ser Ile Val Lys Ser Ile Thr Val Ser Ala Ser Gly
1               5                   10
```

<210> SEQ ID NO 196
<211> LENGTH: 9
<212> TYPE: PRT
<213> ORGANISM: Homo sapiens

<400> SEQUENCE: 196

```
Lys Thr Trp Gly Gln Tyr Trp Gln Val
1               5
```

<210> SEQ ID NO 197
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: May or may not be present

<400> SEQUENCE: 197

Ala Met Leu Gly Thr His Thr Met Glu Val
1               5                   10

<210> SEQ ID NO 198
<211> LENGTH: 9
<212> TYPE: PRT
<213> ORGANISM: Homo sapiens

<400> SEQUENCE: 198

Ile Thr Asp Gln Val Pro Phe Ser Val
1               5

<210> SEQ ID NO 199
<211> LENGTH: 9
<212> TYPE: PRT
<213> ORGANISM: Homo sapiens

<400> SEQUENCE: 199

Tyr Leu Glu Pro Gly Pro Val Thr Ala
1               5

<210> SEQ ID NO 200
<211> LENGTH: 10
<212> TYPE: PRT
<213> ORGANISM: Homo sapiens

<400> SEQUENCE: 200

Leu Leu Asp Gly Thr Ala Thr Leu Arg Leu
1               5                   10

<210> SEQ ID NO 201
<211> LENGTH: 10
<212> TYPE: PRT
<213> ORGANISM: Homo sapiens

<400> SEQUENCE: 201

Val Leu Tyr Arg Tyr Gly Ser Phe Ser Val
1               5                   10

<210> SEQ ID NO 202
<211> LENGTH: 10
<212> TYPE: PRT
<213> ORGANISM: Homo sapiens

<400> SEQUENCE: 202

Ser Leu Ala Asp Thr Asn Ser Leu Ala Val
1               5                   10

<210> SEQ ID NO 203
<211> LENGTH: 9
<212> TYPE: PRT
<213> ORGANISM: Homo sapiens

<400> SEQUENCE: 203

Arg Leu Met Lys Gln Asp Phe Ser Val
1               5

<210> SEQ ID NO 204
<211> LENGTH: 9
<212> TYPE: PRT
<213> ORGANISM: Homo sapiens

<400> SEQUENCE: 204

Arg Leu Pro Arg Ile Phe Cys Ser Cys
1               5

<210> SEQ ID NO 205
<211> LENGTH: 9
<212> TYPE: PRT
<213> ORGANISM: Homo sapiens

<400> SEQUENCE: 205

Leu Ile Tyr Arg Arg Arg Leu Met Lys
1               5

<210> SEQ ID NO 206
<211> LENGTH: 9
<212> TYPE: PRT
<213> ORGANISM: Homo sapiens

<400> SEQUENCE: 206

Ala Leu Leu Ala Val Gly Ala Thr Lys
1               5

<210> SEQ ID NO 207
<211> LENGTH: 10
<212> TYPE: PRT
<213> ORGANISM: Homo sapiens

<400> SEQUENCE: 207

Ile Ala Leu Asn Phe Pro Gly Ser Gln Lys
1               5                   10

<210> SEQ ID NO 208
<211> LENGTH: 9
<212> TYPE: PRT
<213> ORGANISM: Homo sapiens

<400> SEQUENCE: 208

Ala Leu Asn Phe Pro Gly Ser Gln Lys
1               5

<210> SEQ ID NO 209
<211> LENGTH: 9
<212> TYPE: PRT
<213> ORGANISM: Homo sapiens

<400> SEQUENCE: 209

Ala Leu Asn Phe Pro Gly Ser Gln Lys
1               5

<210> SEQ ID NO 210
<211> LENGTH: 9
<212> TYPE: PRT
<213> ORGANISM: Homo sapiens

<400> SEQUENCE: 210

Val Tyr Phe Phe Leu Pro Asp His Leu
1               5

<210> SEQ ID NO 211
<211> LENGTH: 9
<212> TYPE: PRT
<213> ORGANISM: Homo sapiens

<400> SEQUENCE: 211

Arg Thr Lys Gln Leu Tyr Pro Glu Trp
1               5

<210> SEQ ID NO 212
<211> LENGTH: 10
<212> TYPE: PRT
<213> ORGANISM: Homo sapiens

<400> SEQUENCE: 212

His Thr Met Glu Val Thr Val Tyr His Arg
1               5                   10

<210> SEQ ID NO 213
<211> LENGTH: 9
<212> TYPE: PRT
<213> ORGANISM: Homo sapiens

<400> SEQUENCE: 213

Ser Ser Pro Gly Cys Gln Pro Pro Ala
1               5

<210> SEQ ID NO 214
<211> LENGTH: 10
<212> TYPE: PRT
<213> ORGANISM: Homo sapiens

<400> SEQUENCE: 214

Val Pro Leu Asp Cys Val Leu Tyr Arg Tyr
1               5                   10

<210> SEQ ID NO 215
<211> LENGTH: 9
<212> TYPE: PRT
<213> ORGANISM: Homo sapiens

<400> SEQUENCE: 215

Leu Pro His Ser Ser Ser His Trp Leu
1               5

<210> SEQ ID NO 216
<211> LENGTH: 8
<212> TYPE: PRT
<213> ORGANISM: Homo sapiens

<400> SEQUENCE: 216

Ser Asn Asp Gly Pro Thr Leu Ile
1               5

<210> SEQ ID NO 217
<211> LENGTH: 15
<212> TYPE: PRT
<213> ORGANISM: Homo sapiens

<400> SEQUENCE: 217

Gly Arg Ala Met Leu Gly Thr His Thr Met Glu Val Thr Val Tyr
1               5                   10                  15

<210> SEQ ID NO 218
<211> LENGTH: 16
<212> TYPE: PRT
<213> ORGANISM: Homo sapiens

<400> SEQUENCE: 218

Trp Asn Arg Gln Leu Tyr Pro Glu Trp Thr Glu Ala Gln Arg Leu Asp
1               5                   10                  15

```
<210> SEQ ID NO 219
<211> LENGTH: 18
<212> TYPE: PRT
<213> ORGANISM: Homo sapiens

<400> SEQUENCE: 219

Thr Thr Glu Trp Val Glu Thr Thr Ala Arg Glu Leu Pro Ile Pro Glu
1               5                   10                  15

Pro Glu

<210> SEQ ID NO 220
<211> LENGTH: 17
<212> TYPE: PRT
<213> ORGANISM: Homo sapiens

<400> SEQUENCE: 220

Thr Gly Arg Ala Met Leu Gly Thr His Thr Met Glu Val Thr Val Tyr
1               5                   10                  15

His

<210> SEQ ID NO 221
<211> LENGTH: 15
<212> TYPE: PRT
<213> ORGANISM: Homo sapiens

<400> SEQUENCE: 221

Gly Arg Ala Met Leu Gly Thr His Thr Met Glu Val Thr Val Tyr
1               5                   10                  15

<210> SEQ ID NO 222
<211> LENGTH: 15
<212> TYPE: PRT
<213> ORGANISM: Homo sapiens

<400> SEQUENCE: 222

Ser Val Ser Glu Ser Asp Thr Ile Arg Ser Ile Ser Ile Ala Ser
1               5                   10                  15

<210> SEQ ID NO 223
<211> LENGTH: 15
<212> TYPE: PRT
<213> ORGANISM: Homo sapiens

<400> SEQUENCE: 223

Leu Leu Ala Asn Gly Arg Met Pro Thr Val Leu Gln Cys Val Asn
1               5                   10                  15

<210> SEQ ID NO 224
<211> LENGTH: 15
<212> TYPE: PRT
<213> ORGANISM: Homo sapiens

<400> SEQUENCE: 224

Arg Met Pro Thr Val Leu Gln Cys Val Asn Val Ser Val Val Ser
1               5                   10                  15

<210> SEQ ID NO 225
<211> LENGTH: 9
<212> TYPE: PRT
<213> ORGANISM: Homo sapiens

<400> SEQUENCE: 225

Pro Leu Leu Glu Asn Val Ile Ser Lys
1               5
```

```
<210> SEQ ID NO 226
<211> LENGTH: 10
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: May or may not be present

<400> SEQUENCE: 226

Glu Ala Ala Gly Ile Gly Ile Leu Thr Val
1               5                   10

<210> SEQ ID NO 227
<211> LENGTH: 9
<212> TYPE: PRT
<213> ORGANISM: Homo sapiens

<400> SEQUENCE: 227

Ile Leu Thr Val Ile Leu Gly Val Leu
1               5

<210> SEQ ID NO 228
<211> LENGTH: 10
<212> TYPE: PRT
<213> ORGANISM: Homo sapiens

<400> SEQUENCE: 228

Glu Ala Ala Gly Ile Gly Ile Leu Thr Val
1               5                   10

<210> SEQ ID NO 229
<211> LENGTH: 11
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: May or may not be present

<400> SEQUENCE: 229

Ala Glu Glu Ala Ala Gly Ile Gly Ile Leu Thr
1               5                   10

<210> SEQ ID NO 230
<211> LENGTH: 11
<212> TYPE: PRT
<213> ORGANISM: Homo sapiens

<400> SEQUENCE: 230

Arg Asn Gly Tyr Arg Ala Leu Met Asp Lys Ser
1               5                   10

<210> SEQ ID NO 231
<211> LENGTH: 12
<212> TYPE: PRT
<213> ORGANISM: Homo sapiens

<400> SEQUENCE: 231

Glu Glu Ala Ala Gly Ile Gly Ile Leu Thr Val Ile
1               5                   10

<210> SEQ ID NO 232
<211> LENGTH: 14
<212> TYPE: PRT
```

<213> ORGANISM: Homo sapiens

<400> SEQUENCE: 232

Ala Ala Gly Ile Gly Ile Leu Thr Val Ile Leu Gly Val Leu
1               5                   10

<210> SEQ ID NO 233
<211> LENGTH: 12
<212> TYPE: PRT
<213> ORGANISM: Homo sapiens

<400> SEQUENCE: 233

Glu Glu Ala Ala Gly Ile Gly Ile Leu Thr Val Ile
1               5                   10

<210> SEQ ID NO 234
<211> LENGTH: 23
<212> TYPE: PRT
<213> ORGANISM: Homo sapiens

<400> SEQUENCE: 234

Arg Asn Gly Tyr Arg Ala Leu Met Asp Lys Ser Leu His Val Gly Thr
1               5                   10                  15

Gln Cys Ala Leu Thr Arg Arg
            20

<210> SEQ ID NO 235
<211> LENGTH: 20
<212> TYPE: PRT
<213> ORGANISM: Homo sapiens

<400> SEQUENCE: 235

Met Pro Arg Glu Asp Ala His Phe Ile Tyr Gly Tyr Pro Lys Lys Gly
1               5                   10                  15

His Gly His Ser
            20

<210> SEQ ID NO 236
<211> LENGTH: 20
<212> TYPE: PRT
<213> ORGANISM: Homo sapiens

<400> SEQUENCE: 236

Lys Asn Cys Glu Pro Val Val Pro Asn Ala Pro Pro Ala Tyr Glu Lys
1               5                   10                  15

Leu Ser Ala Glu
            20

<210> SEQ ID NO 237
<211> LENGTH: 9
<212> TYPE: PRT
<213> ORGANISM: Homo sapiens

<400> SEQUENCE: 237

Ser Leu Ser Lys Ile Leu Asp Thr Val
1               5

<210> SEQ ID NO 238
<211> LENGTH: 9
<212> TYPE: PRT
<213> ORGANISM: Homo sapiens

<400> SEQUENCE: 238

```
Leu Tyr Ser Ala Cys Phe Trp Trp Leu
1               5
```

<210> SEQ ID NO 239
<211> LENGTH: 10
<212> TYPE: PRT
<213> ORGANISM: Homo sapiens

<400> SEQUENCE: 239

```
Phe Leu Thr Pro Lys Lys Leu Gln Cys Val
1               5                   10
```

<210> SEQ ID NO 240
<211> LENGTH: 10
<212> TYPE: PRT
<213> ORGANISM: Homo sapiens

<400> SEQUENCE: 240

```
Val Ile Ser Asn Asp Val Cys Ala Gln Val
1               5                   10
```

<210> SEQ ID NO 241
<211> LENGTH: 9
<212> TYPE: PRT
<213> ORGANISM: Homo sapiens

<400> SEQUENCE: 241

```
Val Leu His Trp Asp Pro Glu Thr Val
1               5
```

<210> SEQ ID NO 242
<211> LENGTH: 9
<212> TYPE: PRT
<213> ORGANISM: Homo sapiens

<400> SEQUENCE: 242

```
Met Ser Leu Gln Arg Gln Phe Leu Arg
1               5
```

<210> SEQ ID NO 243
<211> LENGTH: 21
<212> TYPE: PRT
<213> ORGANISM: Homo sapiens

<400> SEQUENCE: 243

```
Ile Ser Pro Asn Ser Val Phe Ser Gln Trp Arg Val Val Cys Asp Ser
1               5                   10                  15

Leu Glu Asp Tyr Asp
            20
```

<210> SEQ ID NO 244
<211> LENGTH: 10
<212> TYPE: PRT
<213> ORGANISM: Homo sapiens

<400> SEQUENCE: 244

```
Ser Leu Pro Tyr Trp Asn Phe Ala Thr Gly
1               5                   10
```

<210> SEQ ID NO 245
<211> LENGTH: 9
<212> TYPE: PRT
<213> ORGANISM: Homo sapiens

<400> SEQUENCE: 245

```
Ser Val Tyr Asp Phe Phe Val Trp Leu
1               5

<210> SEQ ID NO 246
<211> LENGTH: 9
<212> TYPE: PRT
<213> ORGANISM: Homo sapiens

<400> SEQUENCE: 246

Thr Leu Asp Ser Gln Val Met Ser Leu
1               5

<210> SEQ ID NO 247
<211> LENGTH: 9
<212> TYPE: PRT
<213> ORGANISM: Homo sapiens

<400> SEQUENCE: 247

Leu Leu Gly Pro Gly Arg Pro Tyr Arg
1               5

<210> SEQ ID NO 248
<211> LENGTH: 9
<212> TYPE: PRT
<213> ORGANISM: Homo sapiens

<400> SEQUENCE: 248

Leu Leu Gly Pro Gly Arg Pro Tyr Arg
1               5

<210> SEQ ID NO 249
<211> LENGTH: 9
<212> TYPE: PRT
<213> ORGANISM: Homo sapiens

<400> SEQUENCE: 249

Ala Asn Asp Pro Ile Phe Val Val Leu
1               5

<210> SEQ ID NO 250
<211> LENGTH: 15
<212> TYPE: PRT
<213> ORGANISM: Homo sapiens

<400> SEQUENCE: 250

Gln Cys Thr Glu Val Arg Ala Asp Thr Arg Pro Trp Ser Gly Pro
1               5                   10                  15

<210> SEQ ID NO 251
<211> LENGTH: 10
<212> TYPE: PRT
<213> ORGANISM: Homo sapiens

<400> SEQUENCE: 251

Ala Leu Pro Tyr Trp Asn Phe Ala Thr Gly
1               5                   10

<210> SEQ ID NO 252
<211> LENGTH: 9
<212> TYPE: PRT
<213> ORGANISM: Homo sapiens

<400> SEQUENCE: 252

Lys Cys Asp Ile Cys Thr Asp Glu Tyr
```

```
<210> SEQ ID NO 253
<211> LENGTH: 11
<212> TYPE: PRT
<213> ORGANISM: Homo sapiens

<400> SEQUENCE: 253

Ser Ser Asp Tyr Val Ile Pro Ile Gly Thr Tyr
1               5                   10

<210> SEQ ID NO 254
<211> LENGTH: 9
<212> TYPE: PRT
<213> ORGANISM: Homo sapiens

<400> SEQUENCE: 254

Met Leu Leu Ala Val Leu Tyr Cys Leu
1               5

<210> SEQ ID NO 255
<211> LENGTH: 10
<212> TYPE: PRT
<213> ORGANISM: Homo sapiens

<400> SEQUENCE: 255

Cys Leu Leu Trp Ser Phe Gln Thr Ser Ala
1               5                   10

<210> SEQ ID NO 256
<211> LENGTH: 9
<212> TYPE: PRT
<213> ORGANISM: Homo sapiens

<400> SEQUENCE: 256

Tyr Met Asp Gly Thr Met Ser Gln Val
1               5

<210> SEQ ID NO 257
<211> LENGTH: 9
<212> TYPE: PRT
<213> ORGANISM: Homo sapiens

<400> SEQUENCE: 257

Ala Phe Leu Pro Trp His Arg Leu Phe
1               5

<210> SEQ ID NO 258
<211> LENGTH: 9
<212> TYPE: PRT
<213> ORGANISM: Homo sapiens

<400> SEQUENCE: 258

Gln Cys Ser Gly Asn Phe Met Gly Phe
1               5

<210> SEQ ID NO 259
<211> LENGTH: 12
<212> TYPE: PRT
<213> ORGANISM: Homo sapiens

<400> SEQUENCE: 259

Thr Pro Arg Leu Pro Ser Ser Ala Asp Val Glu Phe
1               5                   10
```

<210> SEQ ID NO 260
<211> LENGTH: 9
<212> TYPE: PRT
<213> ORGANISM: Homo sapiens

<400> SEQUENCE: 260

Leu Pro Ser Ser Ala Asp Val Glu Phe
1               5

<210> SEQ ID NO 261
<211> LENGTH: 10
<212> TYPE: PRT
<213> ORGANISM: Homo sapiens

<400> SEQUENCE: 261

Leu His His Ala Phe Val Asp Ser Ile Phe
1               5                   10

<210> SEQ ID NO 262
<211> LENGTH: 9
<212> TYPE: PRT
<213> ORGANISM: Homo sapiens

<400> SEQUENCE: 262

Ser Glu Ile Trp Arg Asp Ile Asp Phe
1               5

<210> SEQ ID NO 263
<211> LENGTH: 15
<212> TYPE: PRT
<213> ORGANISM: Homo sapiens

<400> SEQUENCE: 263

Gln Asn Ile Leu Leu Ser Asn Ala Pro Leu Gly Pro Gln Phe Pro
1               5                   10                  15

<210> SEQ ID NO 264
<211> LENGTH: 13
<212> TYPE: PRT
<213> ORGANISM: Homo sapiens

<400> SEQUENCE: 264

Ser Tyr Leu Gln Asp Ser Asp Pro Asp Ser Phe Gln Asp
1               5                   10

<210> SEQ ID NO 265
<211> LENGTH: 21
<212> TYPE: PRT
<213> ORGANISM: Homo sapiens

<400> SEQUENCE: 265

Phe Leu Leu His His Ala Phe Val Asp Ser Ile Phe Glu Gln Trp Leu
1               5                   10                  15

Gln Arg His Arg Pro
            20

<210> SEQ ID NO 266
<211> LENGTH: 9
<212> TYPE: PRT
<213> ORGANISM: Homo sapiens

<400> SEQUENCE: 266

Ser Val Ala Ser Thr Ile Thr Gly Val
1               5

<210> SEQ ID NO 267
<211> LENGTH: 10
<212> TYPE: PRT
<213> ORGANISM: Homo sapiens

<400> SEQUENCE: 267

Arg Ser Asp Ser Gly Gln Gln Ala Arg Tyr
1               5                   10

<210> SEQ ID NO 268
<211> LENGTH: 9
<212> TYPE: PRT
<213> ORGANISM: Homo sapiens

<400> SEQUENCE: 268

Leu Leu Tyr Lys Leu Ala Asp Leu Ile
1               5

<210> SEQ ID NO 269
<211> LENGTH: 10
<212> TYPE: PRT
<213> ORGANISM: Homo sapiens

<400> SEQUENCE: 269

Tyr Leu Asn Asp His Leu Glu Pro Trp Ile
1               5                   10

<210> SEQ ID NO 270
<211> LENGTH: 9
<212> TYPE: PRT
<213> ORGANISM: Homo sapiens

<400> SEQUENCE: 270

Cys Gln Trp Gly Arg Leu Trp Gln Leu
1               5

<210> SEQ ID NO 271
<211> LENGTH: 10
<212> TYPE: PRT
<213> ORGANISM: Homo sapiens

<400> SEQUENCE: 271

Val Leu Leu Gln Ala Gly Ser Leu His Ala
1               5                   10

<210> SEQ ID NO 272
<211> LENGTH: 9
<212> TYPE: PRT
<213> ORGANISM: Homo sapiens

<400> SEQUENCE: 272

Lys Val His Pro Val Ile Trp Ser Leu
1               5

<210> SEQ ID NO 273
<211> LENGTH: 10
<212> TYPE: PRT
<213> ORGANISM: Homo sapiens

<400> SEQUENCE: 273

Leu Met Leu Gln Asn Ala Leu Thr Thr Met
1               5                   10

```
<210> SEQ ID NO 274
<211> LENGTH: 9
<212> TYPE: PRT
<213> ORGANISM: Homo sapiens

<400> SEQUENCE: 274

Leu Leu Gly Ala Thr Cys Met Phe Val
1               5

<210> SEQ ID NO 275
<211> LENGTH: 15
<212> TYPE: PRT
<213> ORGANISM: Homo sapiens

<400> SEQUENCE: 275

Asn Pro Pro Ser Met Val Ala Ala Gly Ser Val Val Ala Ala Val
1               5                   10                  15

<210> SEQ ID NO 276
<211> LENGTH: 10
<212> TYPE: PRT
<213> ORGANISM: Homo sapiens

<400> SEQUENCE: 276

Ala Leu Gly Gly His Pro Leu Leu Gly Val
1               5                   10

<210> SEQ ID NO 277
<211> LENGTH: 9
<212> TYPE: PRT
<213> ORGANISM: Homo sapiens

<400> SEQUENCE: 277

Thr Met Asn Gly Ser Lys Ser Pro Val
1               5

<210> SEQ ID NO 278
<211> LENGTH: 9
<212> TYPE: PRT
<213> ORGANISM: Homo sapiens

<400> SEQUENCE: 278

Arg Tyr Gln Leu Asp Pro Lys Phe Ile
1               5

<210> SEQ ID NO 279
<211> LENGTH: 12
<212> TYPE: PRT
<213> ORGANISM: Homo sapiens

<400> SEQUENCE: 279

Asp Val Thr Phe Asn Ile Ile Cys Lys Lys Cys Gly
1               5                   10

<210> SEQ ID NO 280
<211> LENGTH: 9
<212> TYPE: PRT
<213> ORGANISM: Homo sapiens

<400> SEQUENCE: 280

Phe Met Val Glu Asp Glu Thr Val Leu
1               5

<210> SEQ ID NO 281
<211> LENGTH: 10
```

```
<212> TYPE: PRT
<213> ORGANISM: Homo sapiens

<400> SEQUENCE: 281

Phe Ile Asn Asp Glu Ile Phe Val Glu Leu
1               5                   10

<210> SEQ ID NO 282
<211> LENGTH: 9
<212> TYPE: PRT
<213> ORGANISM: Homo sapiens

<400> SEQUENCE: 282

Lys Tyr Asp Cys Phe Leu His Pro Phe
1               5

<210> SEQ ID NO 283
<211> LENGTH: 9
<212> TYPE: PRT
<213> ORGANISM: Homo sapiens

<400> SEQUENCE: 283

Lys Tyr Val Gly Ile Glu Arg Glu Met
1               5

<210> SEQ ID NO 284
<211> LENGTH: 9
<212> TYPE: PRT
<213> ORGANISM: Homo sapiens

<400> SEQUENCE: 284

Asn Thr Tyr Ala Ser Pro Arg Phe Lys
1               5

<210> SEQ ID NO 285
<211> LENGTH: 9
<212> TYPE: PRT
<213> ORGANISM: Homo sapiens

<400> SEQUENCE: 285

His Leu Ser Thr Ala Phe Ala Arg Val
1               5

<210> SEQ ID NO 286
<211> LENGTH: 9
<212> TYPE: PRT
<213> ORGANISM: Homo sapiens

<400> SEQUENCE: 286

Lys Ile Phe Gly Ser Leu Ala Phe Leu
1               5

<210> SEQ ID NO 287
<211> LENGTH: 9
<212> TYPE: PRT
<213> ORGANISM: Homo sapiens

<400> SEQUENCE: 287

Ile Ile Ser Ala Val Val Gly Ile Leu
1               5

<210> SEQ ID NO 288
<211> LENGTH: 9
<212> TYPE: PRT
<213> ORGANISM: Homo sapiens
```

```
<400> SEQUENCE: 288

Ala Leu Cys Arg Trp Gly Leu Leu Leu
1               5

<210> SEQ ID NO 289
<211> LENGTH: 9
<212> TYPE: PRT
<213> ORGANISM: Homo sapiens

<400> SEQUENCE: 289

Ile Leu His Asn Gly Ala Tyr Ser Leu
1               5

<210> SEQ ID NO 290
<211> LENGTH: 9
<212> TYPE: PRT
<213> ORGANISM: Homo sapiens

<400> SEQUENCE: 290

Arg Leu Leu Gln Glu Thr Glu Leu Val
1               5

<210> SEQ ID NO 291
<211> LENGTH: 9
<212> TYPE: PRT
<213> ORGANISM: Homo sapiens

<400> SEQUENCE: 291

Val Val Leu Gly Val Val Phe Gly Ile
1               5

<210> SEQ ID NO 292
<211> LENGTH: 10
<212> TYPE: PRT
<213> ORGANISM: Homo sapiens

<400> SEQUENCE: 292

Tyr Met Ile Met Val Lys Cys Trp Met Ile
1               5                   10

<210> SEQ ID NO 293
<211> LENGTH: 9
<212> TYPE: PRT
<213> ORGANISM: Homo sapiens

<400> SEQUENCE: 293

His Leu Tyr Gln Gly Cys Gln Val Val
1               5

<210> SEQ ID NO 294
<211> LENGTH: 10
<212> TYPE: PRT
<213> ORGANISM: Homo sapiens

<400> SEQUENCE: 294

Tyr Leu Val Pro Gln Gln Gly Phe Phe Cys
1               5                   10

<210> SEQ ID NO 295
<211> LENGTH: 9
<212> TYPE: PRT
<213> ORGANISM: Homo sapiens

<400> SEQUENCE: 295
```

```
Pro Leu Gln Pro Glu Gln Leu Gln Val
1               5

<210> SEQ ID NO 296
<211> LENGTH: 9
<212> TYPE: PRT
<213> ORGANISM: Homo sapiens

<400> SEQUENCE: 296

Thr Leu Glu Glu Ile Thr Gly Tyr Leu
1               5

<210> SEQ ID NO 297
<211> LENGTH: 9
<212> TYPE: PRT
<213> ORGANISM: Homo sapiens

<400> SEQUENCE: 297

Ala Leu Ile His His Asn Thr His Leu
1               5

<210> SEQ ID NO 298
<211> LENGTH: 9
<212> TYPE: PRT
<213> ORGANISM: Homo sapiens

<400> SEQUENCE: 298

Pro Leu Thr Ser Ile Ile Ser Ala Val
1               5

<210> SEQ ID NO 299
<211> LENGTH: 9
<212> TYPE: PRT
<213> ORGANISM: Homo sapiens

<400> SEQUENCE: 299

Val Leu Arg Glu Asn Thr Ser Pro Lys
1               5

<210> SEQ ID NO 300
<211> LENGTH: 9
<212> TYPE: PRT
<213> ORGANISM: Homo sapiens

<400> SEQUENCE: 300

Thr Tyr Leu Pro Thr Asn Ala Ser Leu
1               5

<210> SEQ ID NO 301
<211> LENGTH: 9
<212> TYPE: PRT
<213> ORGANISM: Homo sapiens

<400> SEQUENCE: 301

Trp Leu Pro Phe Gly Phe Ile Leu Ile
1               5

<210> SEQ ID NO 302
<211> LENGTH: 9
<212> TYPE: PRT
<213> ORGANISM: Homo sapiens

<400> SEQUENCE: 302

Ser Pro Arg Trp Trp Pro Thr Cys Leu
```

```
<210> SEQ ID NO 303
<211> LENGTH: 9
<212> TYPE: PRT
<213> ORGANISM: Homo sapiens

<400> SEQUENCE: 303

Gly Val Ala Leu Gln Thr Met Lys Gln
1               5

<210> SEQ ID NO 304
<211> LENGTH: 9
<212> TYPE: PRT
<213> ORGANISM: Homo sapiens

<400> SEQUENCE: 304

Phe Met Asn Lys Phe Ile Tyr Glu Ile
1               5

<210> SEQ ID NO 305
<211> LENGTH: 10
<212> TYPE: PRT
<213> ORGANISM: Homo sapiens

<400> SEQUENCE: 305

Gln Leu Ala Val Ser Val Ile Leu Arg Val
1               5                   10

<210> SEQ ID NO 306
<211> LENGTH: 14
<212> TYPE: PRT
<213> ORGANISM: Homo sapiens

<400> SEQUENCE: 306

Leu Pro Ala Val Val Gly Leu Ser Pro Gly Glu Gln Glu Tyr
1               5                   10

<210> SEQ ID NO 307
<211> LENGTH: 16
<212> TYPE: PRT
<213> ORGANISM: Homo sapiens

<400> SEQUENCE: 307

Val Gly Gln Asp Val Ser Val Leu Phe Arg Val Thr Gly Ala Leu Gln
1               5                   10                  15

<210> SEQ ID NO 308
<211> LENGTH: 8
<212> TYPE: PRT
<213> ORGANISM: Homo sapiens

<400> SEQUENCE: 308

Val Leu Phe Tyr Leu Gly Gln Tyr
1               5

<210> SEQ ID NO 309
<211> LENGTH: 9
<212> TYPE: PRT
<213> ORGANISM: Homo sapiens

<400> SEQUENCE: 309

Thr Leu Asn Asp Glu Cys Trp Pro Ala
1               5
```

<210> SEQ ID NO 310
<211> LENGTH: 9
<212> TYPE: PRT
<213> ORGANISM: Homo sapiens

<400> SEQUENCE: 310

Gly Leu Pro Pro Asp Val Gln Arg Val
1               5

<210> SEQ ID NO 311
<211> LENGTH: 12
<212> TYPE: PRT
<213> ORGANISM: Homo sapiens

<400> SEQUENCE: 311

Ser Leu Phe Pro Asn Ser Pro Lys Trp Thr Ser Lys
1               5                   10

<210> SEQ ID NO 312
<211> LENGTH: 9
<212> TYPE: PRT
<213> ORGANISM: Homo sapiens

<400> SEQUENCE: 312

Ser Thr Ala Pro Pro Val His Asn Val
1               5

<210> SEQ ID NO 313
<211> LENGTH: 9
<212> TYPE: PRT
<213> ORGANISM: Homo sapiens

<400> SEQUENCE: 313

Leu Leu Leu Leu Thr Val Leu Thr Val
1               5

<210> SEQ ID NO 314
<211> LENGTH: 12
<212> TYPE: PRT
<213> ORGANISM: Homo sapiens

<400> SEQUENCE: 314

Pro Gly Ser Thr Ala Pro Pro Ala His Gly Val Thr
1               5                   10

<210> SEQ ID NO 315
<211> LENGTH: 9
<212> TYPE: PRT
<213> ORGANISM: Homo sapiens

<400> SEQUENCE: 315

Leu Leu Gly Arg Asn Ser Phe Glu Val
1               5

<210> SEQ ID NO 316
<211> LENGTH: 9
<212> TYPE: PRT
<213> ORGANISM: Homo sapiens

<400> SEQUENCE: 316

Arg Met Pro Glu Ala Ala Pro Pro Val
1               5

<210> SEQ ID NO 317

```
<210> SEQ ID NO 317
<211> LENGTH: 9
<212> TYPE: PRT
<213> ORGANISM: Homo sapiens

<400> SEQUENCE: 317

Ser Gln Lys Thr Tyr Gln Gly Ser Tyr
1               5

<210> SEQ ID NO 318
<211> LENGTH: 13
<212> TYPE: PRT
<213> ORGANISM: Homo sapiens

<400> SEQUENCE: 318

Pro Gly Thr Arg Val Arg Ala Met Ala Ile Tyr Lys Gln
1               5                   10

<210> SEQ ID NO 319
<211> LENGTH: 12
<212> TYPE: PRT
<213> ORGANISM: Homo sapiens

<400> SEQUENCE: 319

His Leu Ile Arg Val Glu Gly Asn Leu Arg Val Glu
1               5                   10

<210> SEQ ID NO 320
<211> LENGTH: 9
<212> TYPE: PRT
<213> ORGANISM: Homo sapiens

<400> SEQUENCE: 320

Thr Leu Pro Gly Tyr Pro Pro His Val
1               5

<210> SEQ ID NO 321
<211> LENGTH: 12
<212> TYPE: PRT
<213> ORGANISM: Homo sapiens

<400> SEQUENCE: 321

Cys Thr Ala Cys Arg Trp Lys Lys Ala Cys Gln Arg
1               5                   10

<210> SEQ ID NO 322
<211> LENGTH: 9
<212> TYPE: PRT
<213> ORGANISM: Homo sapiens

<400> SEQUENCE: 322

Val Leu Asp Gly Leu Asp Val Leu Leu
1               5

<210> SEQ ID NO 323
<211> LENGTH: 10
<212> TYPE: PRT
<213> ORGANISM: Homo sapiens

<400> SEQUENCE: 323

Ser Leu Tyr Ser Phe Pro Glu Pro Glu Ala
1               5                   10

<210> SEQ ID NO 324
<211> LENGTH: 10
<212> TYPE: PRT
```

```
<213> ORGANISM: Homo sapiens

<400> SEQUENCE: 324

Ala Leu Tyr Val Asp Ser Leu Phe Phe Leu
 1               5                  10

<210> SEQ ID NO 325
<211> LENGTH: 9
<212> TYPE: PRT
<213> ORGANISM: Homo sapiens

<400> SEQUENCE: 325

Ser Leu Leu Gln His Leu Ile Gly Leu
 1               5

<210> SEQ ID NO 326
<211> LENGTH: 9
<212> TYPE: PRT
<213> ORGANISM: Homo sapiens

<400> SEQUENCE: 326

Leu Tyr Val Asp Ser Leu Phe Phe Leu
 1               5

<210> SEQ ID NO 327
<211> LENGTH: 9
<212> TYPE: PRT
<213> ORGANISM: Homo sapiens

<400> SEQUENCE: 327

Asn Tyr Ala Arg Thr Glu Asp Phe Phe
 1               5

<210> SEQ ID NO 328
<211> LENGTH: 9
<212> TYPE: PRT
<213> ORGANISM: Homo sapiens

<400> SEQUENCE: 328

Leu Lys Leu Ser Gly Val Val Arg Leu
 1               5

<210> SEQ ID NO 329
<211> LENGTH: 10
<212> TYPE: PRT
<213> ORGANISM: Homo sapiens

<400> SEQUENCE: 329

Pro Leu Pro Pro Ala Arg Asn Gly Gly Leu
 1               5                  10

<210> SEQ ID NO 330
<211> LENGTH: 10
<212> TYPE: PRT
<213> ORGANISM: Homo sapiens

<400> SEQUENCE: 330

Ser Pro Ser Ser Asn Arg Ile Arg Asn Thr
 1               5                  10

<210> SEQ ID NO 331
<211> LENGTH: 9
<212> TYPE: PRT
<213> ORGANISM: Homo sapiens
```

```
<400> SEQUENCE: 331

Leu Ala Ala Leu Pro His Ser Cys Leu
1               5

<210> SEQ ID NO 332
<211> LENGTH: 10
<212> TYPE: PRT
<213> ORGANISM: Homo sapiens

<400> SEQUENCE: 332

Gly Leu Ala Ser Phe Lys Ser Phe Leu Lys
1               5                   10

<210> SEQ ID NO 333
<211> LENGTH: 10
<212> TYPE: PRT
<213> ORGANISM: Homo sapiens

<400> SEQUENCE: 333

Arg Ala Gly Leu Gln Val Arg Lys Asn Lys
1               5                   10

<210> SEQ ID NO 334
<211> LENGTH: 10
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: May or may not be present

<400> SEQUENCE: 334

Ala Leu Trp Pro Trp Leu Leu Met Ala Thr
1               5                   10

<210> SEQ ID NO 335
<211> LENGTH: 9
<212> TYPE: PRT
<213> ORGANISM: Homo sapiens

<400> SEQUENCE: 335

Asn Ser Gln Pro Val Trp Leu Cys Leu
1               5

<210> SEQ ID NO 336
<211> LENGTH: 9
<212> TYPE: PRT
<213> ORGANISM: Homo sapiens

<400> SEQUENCE: 336

Leu Pro Arg Trp Pro Pro Pro Gln Leu
1               5

<210> SEQ ID NO 337
<211> LENGTH: 9
<212> TYPE: PRT
<213> ORGANISM: Homo sapiens

<400> SEQUENCE: 337

Lys Met Asp Ala Glu His Pro Glu Leu
1               5

<210> SEQ ID NO 338
<211> LENGTH: 9
<212> TYPE: PRT
```

```
<213> ORGANISM: Homo sapiens

<400> SEQUENCE: 338

Ala Trp Ile Ser Lys Pro Pro Gly Val
1               5

<210> SEQ ID NO 339
<211> LENGTH: 10
<212> TYPE: PRT
<213> ORGANISM: Homo sapiens

<400> SEQUENCE: 339

Ser Ala Trp Ile Ser Lys Pro Pro Gly Val
1               5                   10

<210> SEQ ID NO 340
<211> LENGTH: 9
<212> TYPE: PRT
<213> ORGANISM: Homo sapiens

<400> SEQUENCE: 340

Met Ile Ala Val Phe Leu Pro Ile Val
1               5

<210> SEQ ID NO 341
<211> LENGTH: 15
<212> TYPE: PRT
<213> ORGANISM: Homo sapiens

<400> SEQUENCE: 341

His Gln Gln Tyr Phe Tyr Lys Ile Pro Ile Leu Val Ile Asn Lys
1               5                   10                  15

<210> SEQ ID NO 342
<211> LENGTH: 10
<212> TYPE: PRT
<213> ORGANISM: Homo sapiens

<400> SEQUENCE: 342

Glu Leu Thr Leu Gly Glu Phe Leu Lys Leu
1               5                   10

<210> SEQ ID NO 343
<211> LENGTH: 9
<212> TYPE: PRT
<213> ORGANISM: Homo sapiens

<400> SEQUENCE: 343

Ile Leu Ala Lys Phe Leu His Trp Leu
1               5

<210> SEQ ID NO 344
<211> LENGTH: 9
<212> TYPE: PRT
<213> ORGANISM: Homo sapiens

<400> SEQUENCE: 344

Arg Leu Val Asp Asp Phe Leu Leu Val
1               5

<210> SEQ ID NO 345
<211> LENGTH: 15
<212> TYPE: PRT
<213> ORGANISM: Homo sapiens
```

```
<400> SEQUENCE: 345

Arg Pro Gly Leu Leu Gly Ala Ser Val Leu Gly Leu Asp Asp Ile
1               5                   10                  15

<210> SEQ ID NO 346
<211> LENGTH: 15
<212> TYPE: PRT
<213> ORGANISM: Homo sapiens

<400> SEQUENCE: 346

Leu Thr Asp Leu Gln Pro Tyr Met Arg Gln Phe Val Ala His Leu
1               5                   10                  15

<210> SEQ ID NO 347
<211> LENGTH: 9
<212> TYPE: PRT
<213> ORGANISM: Homo sapiens

<400> SEQUENCE: 347

Ser Arg Phe Gly Gly Ala Val Val Arg
1               5

<210> SEQ ID NO 348
<211> LENGTH: 11
<212> TYPE: PRT
<213> ORGANISM: Homo sapiens

<400> SEQUENCE: 348

Thr Ser Glu Lys Arg Pro Phe Met Cys Ala Tyr
1               5                   10

<210> SEQ ID NO 349
<211> LENGTH: 9
<212> TYPE: PRT
<213> ORGANISM: Homo sapiens

<400> SEQUENCE: 349

Cys Met Thr Trp Asn Gln Met Asn Leu
1               5

<210> SEQ ID NO 350
<211> LENGTH: 11
<212> TYPE: PRT
<213> ORGANISM: Homo sapiens

<400> SEQUENCE: 350

Leu Ser His Leu Gln Met His Ser Arg Lys His
1               5                   10

<210> SEQ ID NO 351
<211> LENGTH: 16
<212> TYPE: PRT
<213> ORGANISM: Homo sapiens

<400> SEQUENCE: 351

Lys Arg Tyr Phe Lys Leu Ser His Leu Gln Met His Ser Arg Lys His
1               5                   10                  15

<210> SEQ ID NO 352
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: modified_base
<222> LOCATION: (14)..(16)
<223> OTHER INFORMATION: a, c, t, g, unknown or other

<400> SEQUENCE: 352
catcgaggga aggnnnctcg ccggaatcgg cattctgacc gtttaatgaa ttctgca         57

<210> SEQ ID NO 353
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(19)
<223> OTHER INFORMATION: a, c, t, g, unknown or other

<400> SEQUENCE: 353
catcgaggga agggagnnng ccggaatcgg cattctgacc gtttaatgaa ttctgca         57

<210> SEQ ID NO 354
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(22)
<223> OTHER INFORMATION: a, c, t, g, unknown or other

<400> SEQUENCE: 354
catcgaggga aggcagctcn nnggaatcgg cattctgacc gtttaatgaa ttctgca         57

<210> SEQ ID NO 355
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(25)
<223> OTHER INFORMATION: a, c, t, g, unknown or other

<400> SEQUENCE: 355
catcgaggga aggcagctcg ccnnnatcgg cattctgacc gtttaatgaa ttctgca         57

<210> SEQ ID NO 356
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(28)
<223> OTHER INFORMATION: a, c, t, g, unknown or other

<400> SEQUENCE: 356
catcgaggga aggcagctcg ccggannngg cattctgacc gtttaatgaa ttctgca         57

<210> SEQ ID NO 357
```

```
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(31)
<223> OTHER INFORMATION: a, c, t, g, unknown or other

<400> SEQUENCE: 357
catcgaggga aggcagctcg ccggaatcnn nattctgacc gtttaatgaa ttctgca       57

<210> SEQ ID NO 358
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(34)
<223> OTHER INFORMATION: a, c, t, g, unknown or other

<400> SEQUENCE: 358
catcgaggga aggcagctcg ccggaatcgg cnnnctgacc gtttaatgaa ttctgca       57

<210> SEQ ID NO 359
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (35)..(37)
<223> OTHER INFORMATION: a, c, t, g, unknown or other

<400> SEQUENCE: 359
catcgaggga aggcagctcg ccggaatcgg cattnnnacc gtttaatgaa ttctgca       57

<210> SEQ ID NO 360
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(40)
<223> OTHER INFORMATION: a, c, t, g, unknown or other

<400> SEQUENCE: 360
catcgaggga aggcagctcg ccggaatcgg cattctgnnn gtttaatgaa ttctgca       57

<210> SEQ ID NO 361

<400> SEQUENCE: 361

000

<210> SEQ ID NO 362
<211> LENGTH: 10
<212> TYPE: PRT
<213> ORGANISM: Homo sapiens
```

```
<400> SEQUENCE: 362

Glu Leu Ala Gly Ile Gly Ile Leu Thr Val
1               5                   10

<210> SEQ ID NO 363
<211> LENGTH: 10
<212> TYPE: PRT
<213> ORGANISM: Homo sapiens

<400> SEQUENCE: 363

Gly Leu Ala Gly Ile Gly Ile Leu Thr Val
1               5                   10

<210> SEQ ID NO 364
<211> LENGTH: 10
<212> TYPE: PRT
<213> ORGANISM: Homo sapiens

<400> SEQUENCE: 364

Ser Leu Ala Gly Ile Gly Ile Leu Thr Val
1               5                   10

<210> SEQ ID NO 365
<211> LENGTH: 10
<212> TYPE: PRT
<213> ORGANISM: Homo sapiens

<400> SEQUENCE: 365

Glu Leu Ala Gly Ile Gly Ile Met Thr Val
1               5                   10

<210> SEQ ID NO 366
<211> LENGTH: 9
<212> TYPE: PRT
<213> ORGANISM: Homo sapiens

<400> SEQUENCE: 366

Ser Leu Leu Met Trp Ile Thr Gln Cys
1               5

<210> SEQ ID NO 367

<400> SEQUENCE: 367

000

<210> SEQ ID NO 368
<211> LENGTH: 14
<212> TYPE: PRT
<213> ORGANISM: Homo sapiens

<400> SEQUENCE: 368

Ser Leu Leu Met Ile Ile Thr Gln Cys Phe Leu Pro Val Phe
1               5                   10

<210> SEQ ID NO 369
<211> LENGTH: 14
<212> TYPE: PRT
<213> ORGANISM: Homo sapiens

<400> SEQUENCE: 369

Ser Leu Leu Met Phe Ile Thr Gln Cys Phe Leu Pro Val Phe
1               5                   10
```

```
<210> SEQ ID NO 370
<211> LENGTH: 14
<212> TYPE: PRT
<213> ORGANISM: Homo sapiens

<400> SEQUENCE: 370

Ser Leu Leu Met Trp Arg Thr Gln Cys Phe Leu Pro Val Phe
1               5                   10

<210> SEQ ID NO 371
<211> LENGTH: 14
<212> TYPE: PRT
<213> ORGANISM: Homo sapiens

<400> SEQUENCE: 371

Ser Leu Leu Met Trp Met Thr Gln Cys Phe Leu Pro Val Phe
1               5                   10

<210> SEQ ID NO 372
<211> LENGTH: 14
<212> TYPE: PRT
<213> ORGANISM: Homo sapiens

<400> SEQUENCE: 372

Ser Leu Leu Met Trp Gln Thr Gln Cys Phe Leu Pro Val Phe
1               5                   10

<210> SEQ ID NO 373
<211> LENGTH: 14
<212> TYPE: PRT
<213> ORGANISM: Homo sapiens

<400> SEQUENCE: 373

Ser Leu Leu Met Trp Val Thr Gln Cys Phe Leu Pro Val Phe
1               5                   10

<210> SEQ ID NO 374
<211> LENGTH: 14
<212> TYPE: PRT
<213> ORGANISM: Homo sapiens

<400> SEQUENCE: 374

Ser Leu Leu Met Trp Ile Thr Ser Cys Phe Leu Pro Val Phe
1               5                   10

<210> SEQ ID NO 375
<211> LENGTH: 14
<212> TYPE: PRT
<213> ORGANISM: Homo sapiens

<400> SEQUENCE: 375

Ser Leu Leu Met Trp Ile Thr Gln Cys Phe Leu Pro Val Trp
1               5                   10

<210> SEQ ID NO 376
<211> LENGTH: 10
<212> TYPE: PRT
<213> ORGANISM: Homo sapiens

<400> SEQUENCE: 376

Ser Leu Leu Met Trp Ile Thr Gln Val Phe
1               5                   10

<210> SEQ ID NO 377
<211> LENGTH: 27
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
ggactcgccg gaatcggcat tctgacc                                          27

<210> SEQ ID NO 378
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
tcactcgccg gaatcggcat tctgacc                                          27

<210> SEQ ID NO 379
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
tcgctcgccg gaatcggcat tctgacc                                          27

<210> SEQ ID NO 380
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
agtctcgccg gaatcggcat tctgacc                                          27

<210> SEQ ID NO 381
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
gagctcgccg gaatcggcat gctgacc                                          27

<210> SEQ ID NO 382
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
agcctgctga tgatcattac ccagtgcttt ctgccggtgt tttaa                      45

<210> SEQ ID NO 383
<211> LENGTH: 45
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 383
agcctgctga tgattattac ccagtgcttt ctgccggtgt tttaa          45

<210> SEQ ID NO 384
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
agcctgctga tgtggattac ctcatgcttt ctgccggtgt tttaa          45

<210> SEQ ID NO 385
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
agcctgctga tgtggattac ccagtgcttt ctgccggtgt tttgg          45

<210> SEQ ID NO 386
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
agcctgctga tgtttattac ccagtgcttt ctgccggtgt tttaa          45

<210> SEQ ID NO 387
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
agcctgctga tgtggaggac ccagtgcttt ctgccggtgt tttaa          45

<210> SEQ ID NO 388
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
agcctgctga tgtggatgac ccagtgcttt ctgccggtgt tttaa          45

<210> SEQ ID NO 389
<211> LENGTH: 45
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 389
agcctgctga tgtggcaaac ccagtgcttt ctgccggtgt tttaa              45

<210> SEQ ID NO 390
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
agcctgctga tgtgggtgac ccagtgcttt ctgccggtgt tttaa              45

<210> SEQ ID NO 391
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
agcctgctga tgtggattac ctcttgcttt ctgccggtgt tttaa              45

<210> SEQ ID NO 392
<211> LENGTH: 9
<212> TYPE: PRT
<213> ORGANISM: Homo sapiens

<400> SEQUENCE: 392

Gly Phe Lys Gln Ser Ser Lys Ala Leu
1               5

<210> SEQ ID NO 393
<211> LENGTH: 17
<212> TYPE: PRT
<213> ORGANISM: Homo sapiens

<400> SEQUENCE: 393

Ala Thr Gly Phe Lys Gln Ser Ser Lys Ala Leu Gln Arg Pro Val Ala
1               5                   10                  15

Ser

<210> SEQ ID NO 394
<211> LENGTH: 17
<212> TYPE: PRT
<213> ORGANISM: Homo sapiens

<400> SEQUENCE: 394

Ala Thr Gly Phe Lys Gln Ser Ser Lys Ala Leu Gln Arg Pro Val Ala
1               5                   10                  15

Ser

<210> SEQ ID NO 395

<400> SEQUENCE: 395

000
```

<210> SEQ ID NO 396

<400> SEQUENCE: 396

000

<210> SEQ ID NO 397

<400> SEQUENCE: 397

000

<210> SEQ ID NO 398

<400> SEQUENCE: 398

000

<210> SEQ ID NO 399

<400> SEQUENCE: 399

000

<210> SEQ ID NO 400

<400> SEQUENCE: 400

000

<210> SEQ ID NO 401

<400> SEQUENCE: 401

000

<210> SEQ ID NO 402

<400> SEQUENCE: 402

000

<210> SEQ ID NO 403

<400> SEQUENCE: 403

000

<210> SEQ ID NO 404

<400> SEQUENCE: 404

000

<210> SEQ ID NO 405

<400> SEQUENCE: 405

000

<210> SEQ ID NO 406

<400> SEQUENCE: 406

000

<210> SEQ ID NO 407

```
<400> SEQUENCE: 407

000

<210> SEQ ID NO 408

<400> SEQUENCE: 408

000

<210> SEQ ID NO 409

<400> SEQUENCE: 409

000

<210> SEQ ID NO 410

<400> SEQUENCE: 410

000

<210> SEQ ID NO 411

<400> SEQUENCE: 411

000

<210> SEQ ID NO 412

<400> SEQUENCE: 412

000

<210> SEQ ID NO 413
<211> LENGTH: 14
<212> TYPE: PRT
<213> ORGANISM: Homo sapiens

<400> SEQUENCE: 413

Thr Leu Tyr Gln Asp Asp Thr Leu Thr Leu Gln Ala Ala Gly
1               5                   10

<210> SEQ ID NO 414
<211> LENGTH: 15
<212> TYPE: PRT
<213> ORGANISM: Homo sapiens

<400> SEQUENCE: 414

Ile Gly Arg Ile Ala Glu Cys Ile Leu Gly Met Asn Pro Ser Arg
1               5                   10                  15

<210> SEQ ID NO 415
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 415

His His His His His His
1               5

<210> SEQ ID NO 416
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid

<400> SEQUENCE: 416

Glu Xaa Ala Gly Ile Gly Ile Leu Thr Val
1               5                   10
```